(12) United States Patent
Matsumoto et al.

(10) Patent No.: US 8,204,568 B2
(45) Date of Patent: Jun. 19, 2012

(54) BLOOD INSPECTION DEVICE

(75) Inventors: Toshiki Matsumoto, Ehime (JP);
Masaki Fujiwara, Ehime (JP);
Toshihiro Akiyama, Ehime (JP);
Keisuke Matsumura, Ehime (JP)

(73) Assignee: Panasonic Corporation, Osaka (JP)

( * ) Notice: Subject to any disclaimer, the term of this patent is extended or adjusted under 35 U.S.C. 154(b) by 901 days.

(21) Appl. No.: 12/293,624

(22) PCT Filed: Mar. 22, 2007

(86) PCT No.: PCT/JP2007/055918
§ 371 (c)(1),
(2), (4) Date: Sep. 19, 2008

(87) PCT Pub. No.: WO2007/108517
PCT Pub. Date: Sep. 27, 2007

(65) Prior Publication Data
US 2010/0168534 A1    Jul. 1, 2010

(30) Foreign Application Priority Data

Mar. 22, 2006 (JP) ................................ 2006-078416
Mar. 22, 2006 (JP) ................................ 2006-078424

(51) Int. Cl.
*A61B 5/05* (2006.01)
*A61B 5/00* (2006.01)
*A61B 5/04* (2006.01)

(52) U.S. Cl. ......... 600/347; 600/345; 600/365; 600/573
(58) Field of Classification Search ........................ None
See application file for complete search history.

(56) References Cited

U.S. PATENT DOCUMENTS

| 5,643,252 A | 7/1997 | Waner et al. |
| 5,839,446 A | 11/1998 | Waner et al. |
| 5,947,957 A | 9/1999 | Morris |
| 6,349,229 B1 | 2/2002 | Watanabe et al. |
| 6,387,059 B1 | 5/2002 | Marchitto et al. |
| 6,426,628 B1 * | 7/2002 | Palm et al. ..................... 324/427 |
| 6,733,493 B2 | 5/2004 | Gruzdev et al. |
| 7,133,703 B2 * | 11/2006 | Aoshima et al. ............... 455/574 |
| 2002/0058953 A1 | 5/2002 | Gruzdev et al. |
| 2002/0130042 A1 | 9/2002 | Moerman et al. |
| 2002/0169394 A1 | 11/2002 | Eppstein et al. |
| 2002/0173732 A1 | 11/2002 | Hakky et al. |
| 2004/0185913 A1 | 9/2004 | Aoshima et al. |
| 2004/0210279 A1 | 10/2004 | Gruzdev et al. |
| 2005/0011759 A1 | 1/2005 | Moerman et al. |

FOREIGN PATENT DOCUMENTS

| JP | 10-501992 | 2/1998 |
| JP | 11-347018 | 12/1999 |
| JP | 2003-524496 | 8/2003 |
| JP | 2004-195245 | 7/2004 |
| JP | 2004-533866 | 11/2004 |
| WO | 01/64105 | 9/2001 |

OTHER PUBLICATIONS

English language Abstract of JP 2004-195245, Jul. 15, 2004.
U.S. Appl. No. 12/293,670 to Fujiwara et al., which was filed Sep. 19, 2008.
Search report from E.P.O., mail date is Feb. 10, 2012.

* cited by examiner

*Primary Examiner* — Tracy Vivlemore
(74) *Attorney, Agent, or Firm* — Greenblum & Bernstein, P.L.C.

(57) ABSTRACT

A blood inspection device using laser as puncture means. The blood inspection device has an electric power source control circuit for controlling electric power supply of an electric power source section including an electric power source for driving an electric circuit for measurement and also including an electric power source for driving a laser emission device. When a battery is used as the electric power source, the circuit measures the remaining level and voltage of the battery to control the power source so that electric power shortage does not disenable measurement.

19 Claims, 51 Drawing Sheets

BLOOD INSPECTION DEVICE

TECHNICAL FIELD

The present invention relates to a blood test apparatus for examining, for example, blood component.

BACKGROUND ART

Diabetes patients need to measure the blood sugar level regularly and administer insulin based on the blood sugar level to maintain a normal blood sugar level. To maintain this normal blood sugar level, diabetes patients need to measure the blood sugar level regularly, sample a small amount of blood from fingertips using a blood test apparatus, and measure the blood sugar level from this sampled blood.

The conventional blood test apparatus generally uses a needle as a means for puncturing skin (see Patent Document 1, for example). As shown in FIG. 1, conventional blood test apparatus 1 which uses a needle as a puncturing means, includes: housing 2 that forms a chassis; cylindrical body 3 having opening at one side included in housing 2; plunger 4 that moves back and forth inside cylindrical body 3; handle 5, one end of which is connected to plunger 4; latch part 6 that latches handle 5 at housing 2; spring 7 that urges handle 5 toward opening part 3a of cylindrical body 3; lancet 9 which has one end held by plunger 4 and the other end attached with blood collection needle (hereinafter "needle") 8; holding part 11 that holds blood sensor 10 on the side of opening part 3a; and electrical circuit section 12 to which the output of sensor 10 is connected.

In order to examine blood using conventional blood test apparatus 1, the following preparation works are necessary. Blood sensor 10 and needle 8 are replaced to eliminate the influence of blood which has already been examined. In order to remove blood sensor 10 after use and attach new blood sensor 10, holding part 11 is removed and then sensor 10 after use is removed. Next, new blood sensor 10 is attached to holding part 11. Then, holding part 11 is attached to opening part 3a again. If the neighborhood of holding part 11 is stained with, for example, blood, it is cleaned.

These preparation works are troublesome for diabetes patients with poor eyesight. In addition, these works must be performed several times a day and are burdensome.

After these preparation works are done, blood test apparatus 1 is abutted on the skin of the patient, and the latching of latch part 6 is released. Then, handle 5, urged by spring 7, is propelled in the direction of arrow 14. By this release of latching of handle 5, needle 8, connected to this handle 5 via plunger 4 and lancet 9, is propelled at the same time. Needle 8 breaks through sensor 10 and punctures skin 13.

A small amount of blood flows out from punctured skin 13. The outflowing blood is guided into inside blood sensor 10. The blood guided into blood sensor 10 causes chemical change in sensor 10 according to the blood sugar level of the patient. The current produced by the chemical change is led to electrical circuit section 12, and the blood sugar level is measured. The calculated blood sugar level is displayed on display section 15. Based on the calculated blood sugar level, for example, basic data showing the amount of insulin to administer to the patient is provided.

On the other hand, an apparatus for sampling blood using laser light for the puncturing means, is also proposed (see Patent Documents 2 and 3). Use of laser light provides an advantage of making unnecessary replacement of needle and possibly alleviating the pain of the patient upon puncturing.

Patent Document 1: Japanese Patent Application Publication No. 2003-524496
Patent Document 2: Japanese Patent Application Publication No. 2004-533866
Patent Document 3: Japanese Patent Application Laid-Open No. 2004-195245

DISCLOSURE OF INVENTION

Problems to be Solved by the Invention

A laser apparatus consumes a large amount of power, and, for example, when a battery is used for the power supply, the battery capacity may be used up after several times of puncturing. The battery for the power supply, which is used up, no longer enables puncturing, much less the operation of the measuring circuit for examining blood. The blood test apparatus is an apparatus that influences life of the patient (for example, diabetes patient) who is the user, and should be designed so that, even if the puncturing means does not operate, at least blood test (for example, measurement of blood sugar level) can be performed, because puncturing can be performed using a means other than laser light.

It is therefore an object of the present invention to provide a blood test apparatus that makes unnecessary replacement of a blood collection needle and uses laser light as the puncturing means, and that can perform blood test at least, even if laser puncturing is not possible due to shortage of the battery capacity.

Means for Solving the Problem

The first aspect of the present invention relates to the following blood test apparatus.

[1] The blood test apparatus includes: an apparatus body; a blood sensor that is attached to the apparatus body and that analyzes blood; a puncturing section that is provided inside the apparatus body and that punctures skin of a patient through the blood sensor; and an electrical circuit section that is connected to the blood sensor, and in the blood test apparatus, the puncturing section includes a laser emitting apparatus; and the blood test apparatus includes a power supply control circuit that controls a supply of power from a power supply section including a power supply for driving the electrical circuit section and a power supply for driving the laser emitting apparatus.

[2] In the blood test apparatus according to [1], the power supply section comprises one or more battery power supplies.

[3] The blood test apparatus according to [2], further includes: a battery level measuring circuit that measures a battery level of at least one of the one or more batteries; and a comparing section that compares a value of the measured battery level and a predetermined value of a battery level, and in the blood test apparatus, the power supply control circuit controls the supply of power based on an output result of the comparing section.

[4] The blood test apparatus according to [2], further includes: a battery voltage measuring circuit that measures a battery voltage of at least one of the one or more batteries; and a comparing section that compares a value of the measured battery voltage and a predetermined value of a battery voltage, and in the blood test apparatus, the power supply control circuit controls the supply of power based on an output result of the comparing section.

The blood test apparatus of [3] and [4] may further include a display section that displays a test result of the blood test.

The second aspect of the present invention relates to the following method of controlling the blood test apparatus.

[5] A control method for controlling the blood test apparatus according to [3], comprising the steps of: a pre-operation battery level measuring step of measuring a battery level of the battery after a power supply of the apparatus body is started; a post-operation battery level measuring step of measuring a battery level of the battery after the pre-operation battery level measuring step is performed and a laser light is emitted from the laser emitting apparatus; and a step of measuring battery consumption level from a difference between the battery level measured in the pre-operation battery level measuring step and the battery level measured in the post-operation battery level measuring step.

[6] A control method for controlling the blood test apparatus according to [4], comprising the steps of: a battery level measuring step of measuring a battery level of the battery; a step of comparing the measured battery level and a battery threshold which is a predetermined battery level; and a display step of displaying a message to encourage a change of the battery on the display section when the measured battery level is equal to or less than the battery level threshold.

Advantageous Effect of the Invention

The blood test apparatus of the present invention can prevent a situation wherein test cannot be performed due to power shortage of the power supply although laser light is used as the puncturing means. Particularly, even if the battery with a limited capacity is used for the power supply, the user can perform a test stably. Therefore, the present invention is particularly applicable to a portable blood test apparatus.

BRIEF DESCRIPTION OF DRAWINGS

FIG. 15 shows exploded plan views of the blood sensor of FIG. 8, where

FIG. 42 shows examples of a cube that can be used in the laser branch control in FIG. 39, where

FIG. 48 shows still another examples of the laser output control in the blood test apparatus of the present invention, where

FIG. 49 shows still another examples of the laser output control in the blood test apparatus of the present invention, where

FIG. 63 shows another examples of the laser branch control in the blood test apparatus with the laser perforation apparatus of the present invention, where

BEST MODE FOR CARRYING OUT THE INVENTION

Figure 1:
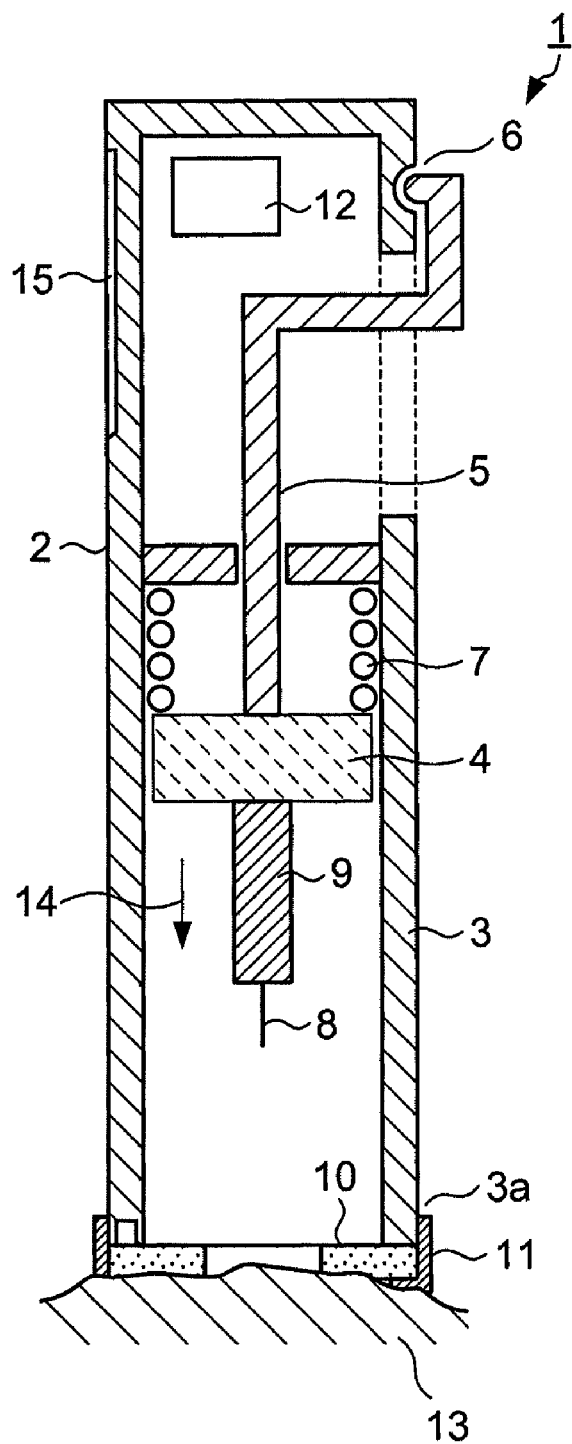
FIG. 1 is a cross-sectional view showing an example of a conventional blood test apparatus.

The present invention provides a blood test apparatus using laser light as a means for puncturing skin and can bring skin in a predetermined position by sucking force. The focal point of laser light is set correctly with respect to the skin brought in the predetermined position. In addition, the skin is placed in close contact with the blood sensor by sucking force, so that the blood flowing out from the skin punctured with laser light can be led inside the blood sensor (detecting section) in a reliable manner. The blood test apparatus of the present invent ion will be described below with reference to the drawings. Common parts in the figures will be assigned the same reference numerals without further explanations.

Overall View 1 of the Apparatus

Figure 2:
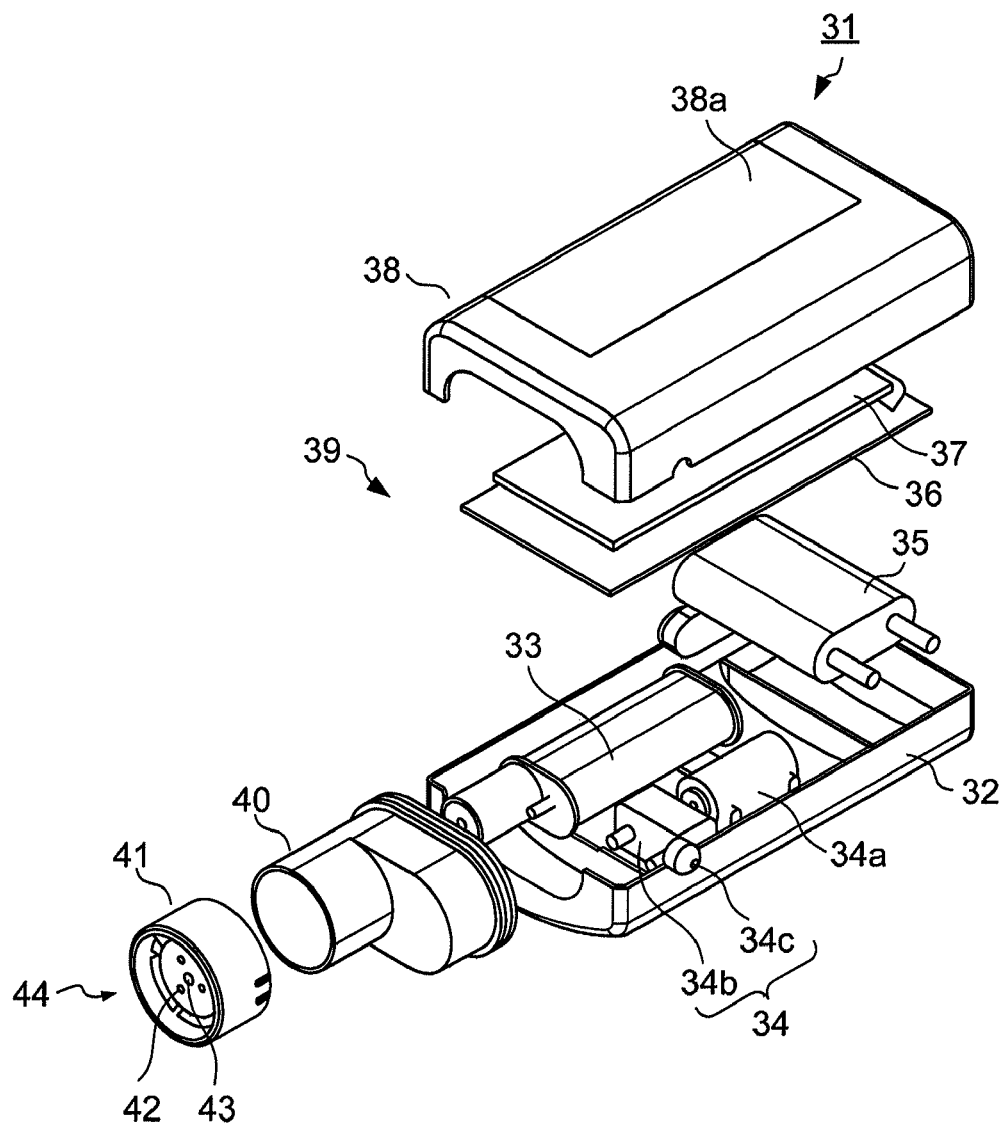
FIG. 2 is an exploded assembly perspective view showing a first example of the blood test apparatus of the present invention.

FIG. 2 is an exploded assembly perspective view showing the overall configuration of a first example of the blood test apparatus of the present invention. The interior of lower case 32 of blood test apparatus 31 shown in FIG. 2 accommodates components including: laser emitting apparatus 33; negative pressure means 34 which is configured with suction pump (negative pressure pump) 34a, pump valve unit 34b and vent switch 34c; battery which supplies power to electrical components; electrical circuit section 36 which is mounted on these components; and display section 37 which is mounted on electrical circuit section 36, and, for example, made of liquid crystal. Apparatus body 39 is configured so that upper case 38 covers lower case 32 that accommodates the components. Transparent display window 38a is provided in upper case 38 in the position corresponding to display section 37.

Apparatus body 39 is connected to blood sensor unit 44 via adapter 40. One end of adapter 40 is a cylinder-shaped body, and blood sensor unit 44 is inserted removably into adapter 40. Blood sensor unit 44 is configured with holder 41 and blood sensor 42 attached inside holder 41. Window 43 provided in the center of blood sensor unit 44 is a part for allowing laser light from the laser emitting hole of laser emitting apparatus 33 to pass through. Window 43 may be a hole or a member formed with a material that allows laser light to pass through.

Overall View 2 of the Apparatus

Figure 3:
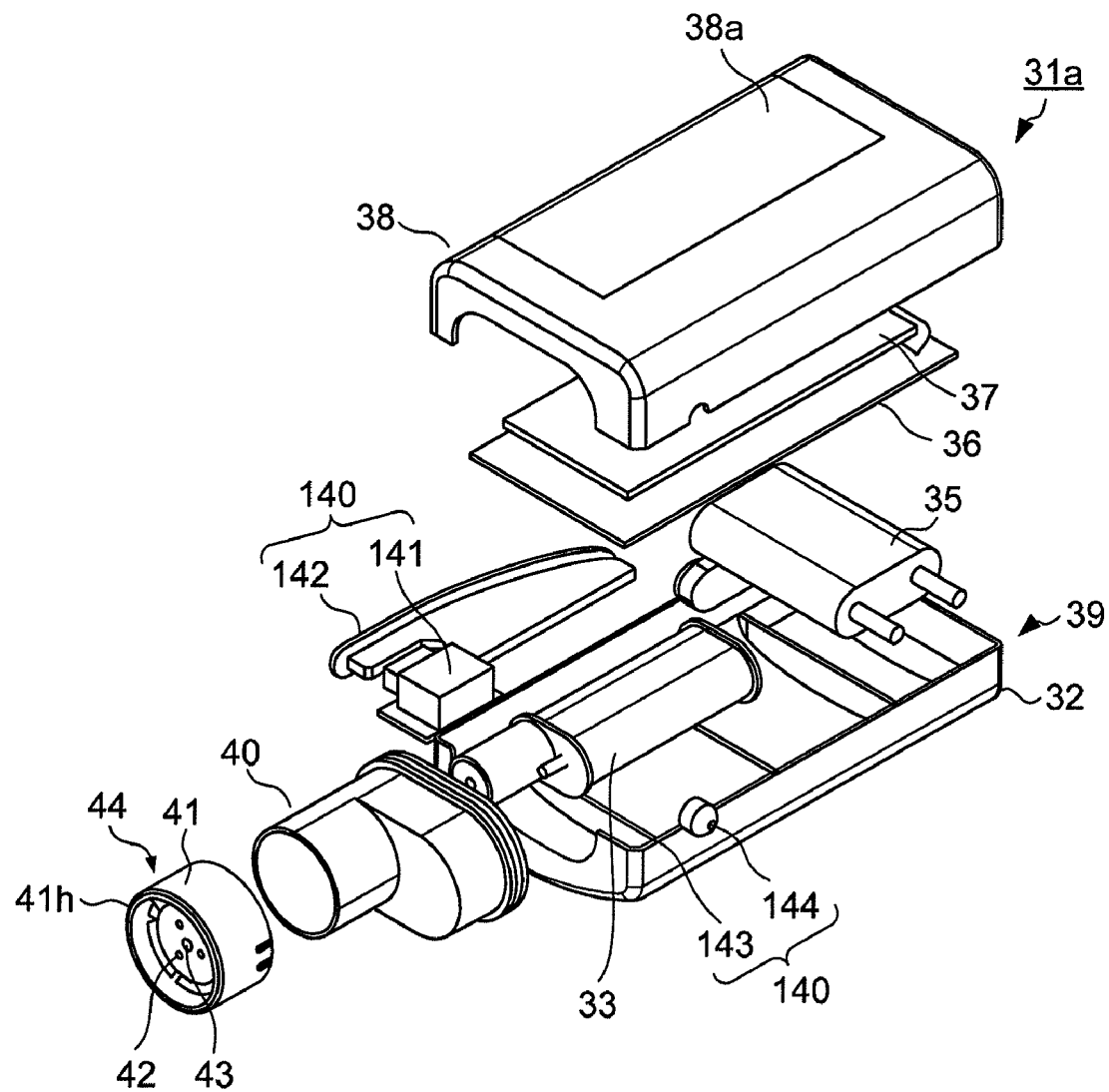
FIG. 3 is an exploded assembly perspective view showing a second example of the blood test apparatus of the present invention.
Figure 4:
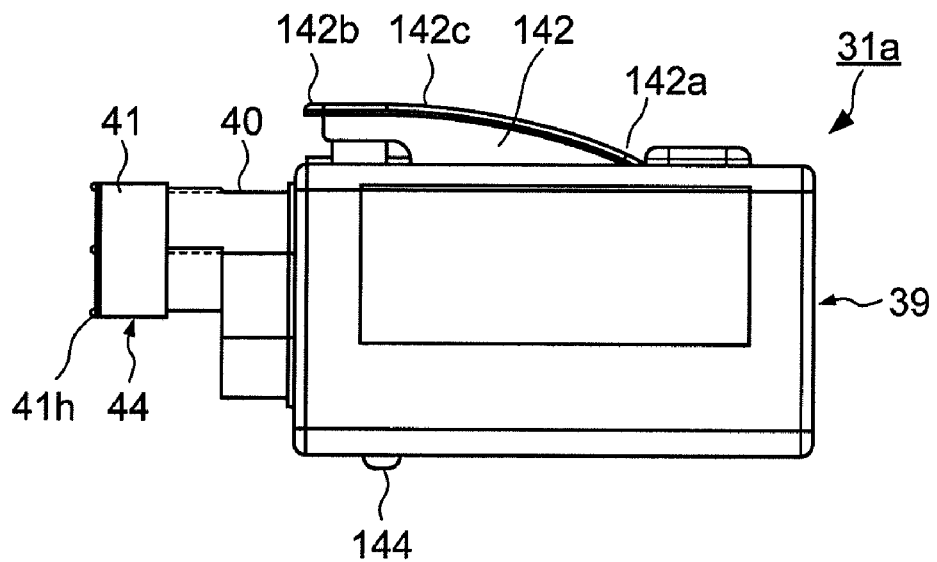
FIG. 4 is a side view of the blood test apparatus of FIG. 3.

FIG. 3 is an exploded assembly perspective view showing the overall configuration of a second example of the blood test apparatus of the present invention. FIG. 4 is its side view. Blood test apparatus 31*a* shown in FIG. 3 and FIG. 4 is different from blood test apparatus 31 shown in FIG. 2 in that the apparatus has a manual pump that enables manual suction as a negative pressure pump constituting negative pressure means 140. The difference will be described below.

Blood test apparatus 31*a* has negative pressure means 140 including manual pump (negative pressure pump) 141 and manual pump knob 142 that drives manual pump 141 manually. Vent switch 144 releases the negative pressure created in pump valve unit 143 to the atmosphere.

Manual pump knob 142 has the shape of an arch, and its one end is made spindle 142*a* and the other end is made operating part 142*b* (see FIG. 4). Manual pump knob 142 can rotate about spindle 142*a*. Operating part 142*b* transmits power to manual pump 141. The patient holds manual pump knob 142 with apparatus body 39 and can move operating part 142*b* up and down. By this up-and-down motion manual pump 141 starts to create a negative pressure.

To create an adequate negative pressure by the up-and-down motion of operating part 142*b* while checking lift of the skin, the exterior of blood sensor unit 44 is preferably formed with a transparent material so that the interior of negative pressure chamber 60 (see FIG. 16, for example) can be seen. The whole of the exterior of blood sensor unit 44 may be formed with a transparent material or only the tip 41*h* side (the negative pressure chamber 60 side) of blood sensor unit 44 may be formed with a transparent material. Grip part 142*c* of manual pump knob 142 may have finger-shaped pattern with indentations and projections to prevent the fingers from slipping.

By driving negative pressure means 140 manually, it is not necessary to supply power for driving negative pressure means 140, which extends the life of battery 35 and makes the apparatus suitable for a portable blood test apparatus.

The First Aspect of the Laser Emitting Apparatus (Including a Lens)

The blood test apparatus of the present invention uses laser light as a means for puncturing skin. When the skin is irradiated with laser light, the laser light is absorbed by the OH group of water of the skin, which increases heat instantaneously and evaporates the water. The surrounding cells also evaporate at this time, to form a hole in the skin.

Figure 5:
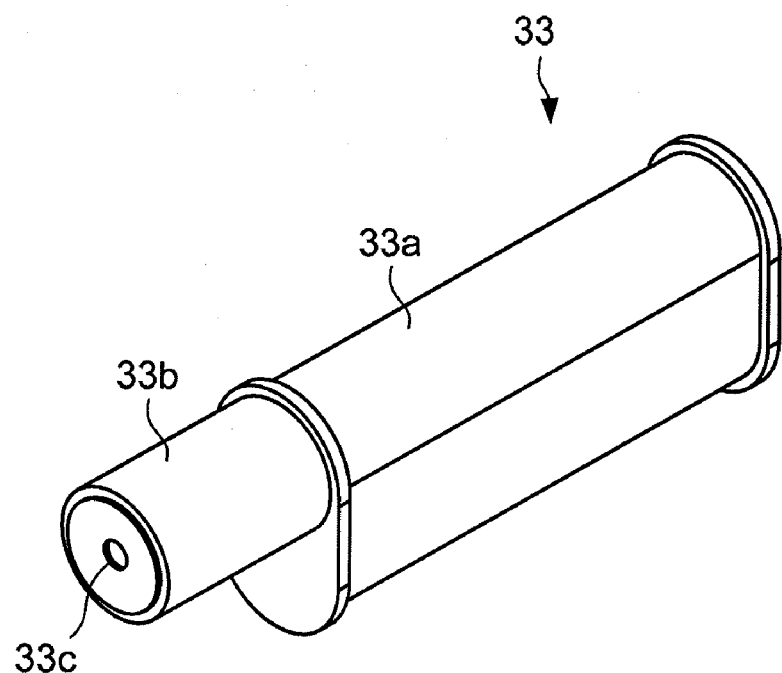
FIG. 5 is an exterior perspective view showing an example of a laser emitting apparatus in the blood test apparatus of the present invention.
Figure 6A:
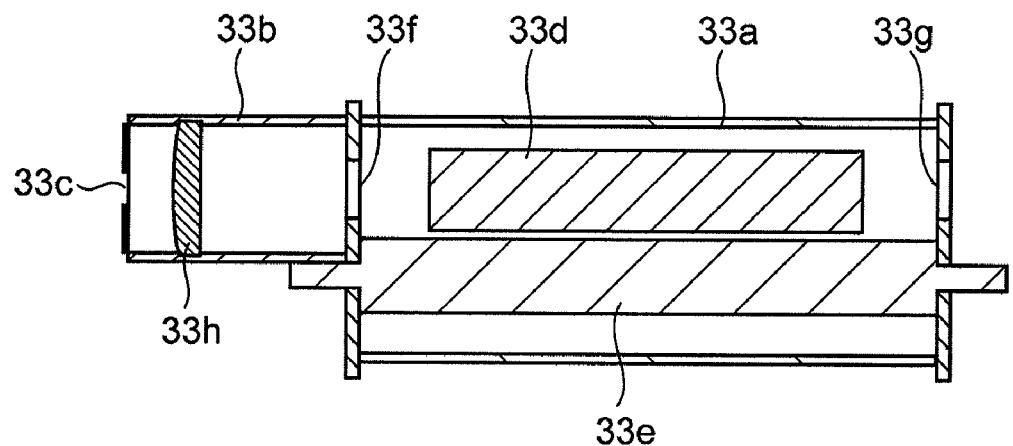
FIG. 6A is a cross-sectional view showing a configuration example of the laser emitting apparatus of FIG. 5.
Figure 6B:
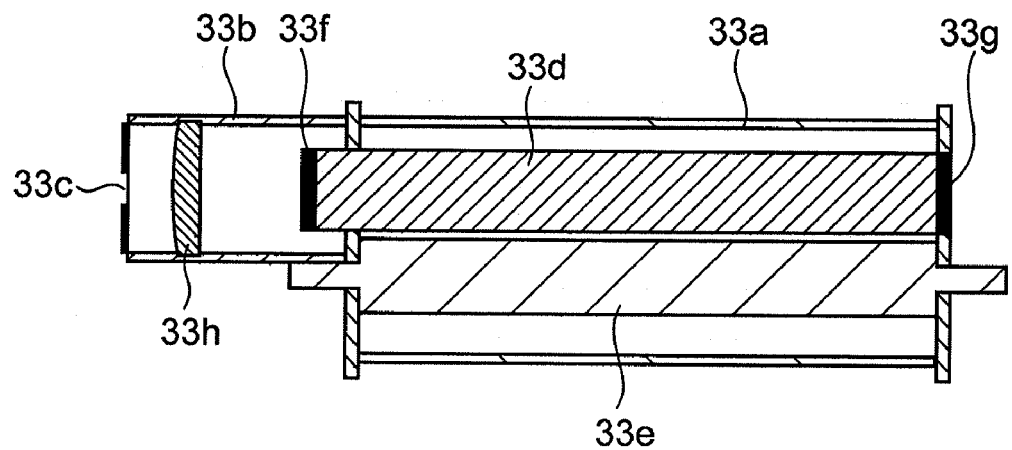
FIG. 6B is a cross-sectional view showing another configuration example of the laser emitting apparatus of FIG. 5.

The blood test apparatus accommodates a laser emitting apparatus. FIG. 5 is an exterior perspective view of laser emitting apparatus 33 accommodated in the blood test apparatus. Further, FIG. 6A and FIG. 6B are cross-sectional views of laser emitting apparatus 33. In FIG. 6A, laser crystal 33*d* is arranged in the internal part surrounded by the walls where partially reflecting mirror 33*f* and total reflection mirror 33*g* are provided. In FIG. 6B, laser crystal 33*d* has partially reflecting mirror 33*f* and total reflection mirror 33*g* on both sides and is attached on the outer wall and the inner wall (partition) of cylindrical body 33*b*. That is, in FIG. 6B, laser crystal (laser rod) 33*d* is long and extends beyond the inner wall (partition). Laser emitting apparatus 33 is configured with oscillation tube 33*a* and cylindrical body 33*b* connected to front side of oscillation tube 33*a*. Laser emitting port 33*c* is provided in the center of the front side of cylindrical body 33*b*.

Oscillation tube 33*a* accommodates Er:YAG (yttrium aluminum garnet) doped with erbium, or Ho:YAG laser crystal 33*d* doped with Holmium, and excitation light source 33*e* which includes a xenon flashlamp. Partially reflecting mirror 33*f* is attached at one end of oscillation tube 33*a* (particularly, see FIG. 6A). The transmittance of partially reflecting mirror 33*f* may be approximately 1 to 10%. Total reflection mirror 33*g* with a transmittance of 99 to 100% is attached to the other end of oscillation tube 33*a* (see FIG. 6A and FIG. 6B). Further, instead of using partially reflecting mirror 33*f* and total reflection mirror 33*g*, films having the same properties may be placed on the end face of the laser crystal by sputtering. Convex lens (focus lens) 33*h* is mounted inside cylindrical body 33*b*. Convex lens 33*h* focuses laser light near the surface of blood sensor 42 (described in detail later). Total reflection mirror 33*g*, YAG laser crystal 33*d*, partially reflecting mirror 33*f*, lens 33*h* and laser emitting hole 33*c* are arranged in this order.

The process of emitting laser light from laser emitting apparatus 33 will be described. For example, the excitation light emitted from excitation light source 33*e* penetrates to Er:YAG laser crystal 33*d* and creates a high energy state by exciting Er (erbium) ion. By this means, Er:YAG laser crystal 33*d* becomes a reverse distribution state, and laser light resonates and is amplified in YAG laser crystal 33*d* while reflecting between total reflection mirror 33*g* and partially reflecting mirror 33*f*. The same applies to the case of Ho (Holmium). Part of the amplified laser light passes through partially reflecting mirror 33*f* by stimulated emission. The laser light passing through partially reflecting mirror 33*f* passes through lens 33*h* and is emitted from laser emitting port 33*c*. As described later, the laser light emitted from laser emitting port 33*c* punctures (irradiates) the skin.

A Second Aspect of the Laser Emitting Apparatus

Figure 7:
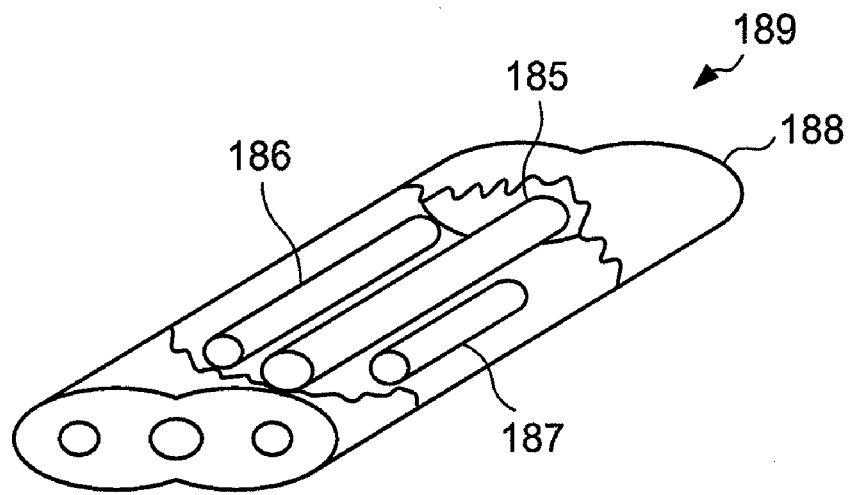
FIG. 7 is a partially broken perspective view showing another example of the laser emitting apparatus in the blood test apparatus of the present invention.

FIG. 7 shows another example of the laser emitting apparatus. Laser emitting apparatus 189 shown in FIG. 7 irradiates two kinds of laser crystals with excitation light using one flashlamp 185 as an excitation light source. At this time, laser light is outputted from each laser crystal. Use of two kinds of crystals enables output of laser lights of different intensities and wavelengths.

As shown in FIG. 7, laser emitting apparatus 189 includes: chassis 188 which has a shape of two overlapping cylindrical bodies having an elliptical cross section; flashlamp 185 for exciting laser light, which is arranged in the central position of chassis 188; and first crystal 186 and second crystal 187 for oscillating laser light, which are arranged at the both sides of flashlamp 185. There are three focal points in elliptical chassis 188. Chassis 188 has a shape of two overlapping ellipses. Each ellipse has two focal points and shares one focal point with the other ellipse, so that there are three focal points. Out of the three focal points, first crystal 186 is arranged in one of the focal points, and second crystal 187 is arranged in another focal point. Flashlamp 185 is arranged in the center part where two focal points overlap. Laser lights can be generated from two crystals 186 and 187 using one flashlamp 185, so that it is possible to realize a smaller and lower-cost laser emitting apparatus.

The intensity of laser light output is proportional to the light emitting intensity of flashlamp 185 and is also proportional to the volumes of crystal 186 and crystal 187. Therefore, by arranging two crystals of the same diameter and different lengths, it is possible to obtain two laser lights of different intensities using one flashlamp 185.

Further, by using crystals of the same volume, it is possible to output two laser lights with the same intensity at the same time. Therefore, even if a laser light is not divided into branches (see FIG. 39 and FIG. 40), skin can be punctured with two laser lights of the same intensity. In this case, energy loss due to branching by a splitter and mirror is prevented.

By arranging two crystals with different compositions (for example, an Er:YAG laser crystal with a wavelength of 2.94 µm and an Nd:YAG crystal with a wavelength of 1.06 µm), it is possible to obtain laser lights with different wavelengths. By irradiating the same position with laser lights having different wavelengths, it is possible to make pricks of different depths in skin. For example, Er:YAG and Nd:YAG have different absorption rates by OH group. Therefore, it is possible to make a shallower prick using Er:YAG with a high absorption rate and make a deeper prick using Nd:YAG with a lower absorption rate than Er:YAG. By emitting two laser lights at the same time utilizing these properties, it is possible to make a prick on the skin more efficiently. When the two laser lights are emitted, Er:YAG and Nd:YAG are preferably emitted in this order with a little time lag.

By using laser emitting apparatus 189, it is possible to use the wavelength of the laser light selectively. Further, by irradiating the same position with two types of laser lights using an optical system, it is possible to improve output intensity.

The blood test apparatus of the present invention uses a laser emitting apparatus as a means for puncturing the skin of the patient that can perform puncturing without contact with the skin, so that the puncturing needle required in the conventional blood test apparatus, is no longer required. Further, the blood test apparatus uses a puncturing means that does not contact with the skin of the patient, and so is sanitary. Still further, although it is necessary to replace the puncturing needle every test by the conventional blood test apparatus, the test by the blood test apparatus of the present invention does not require this replacement. Further, the blood test apparatus of the present invention does not require moving component for moving a needle required for puncturing with a needle, which reduces troubles. Further, the number of components required in the blood test apparatus of the present invention is reduced, so that components control becomes simple. Further, by providing a transparent waterproof wall on the front face of laser emitting port 33c, it is possible to wash the whole of the blood test apparatus.

The Blood Sensor

The blood test apparatus of the present invention has a blood sensor for taking in the blood flowing out from the punctured skin and examining the blood components.

The First Example of the Blood Sensor

Figure 8:
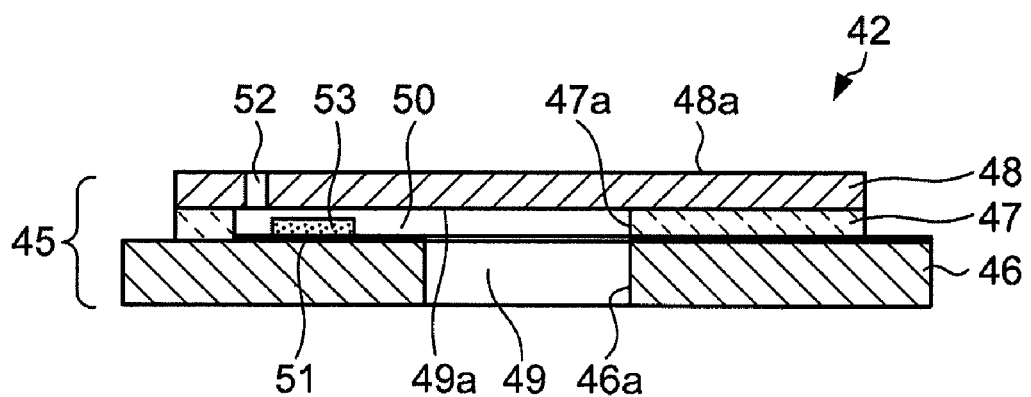
FIG. 8 is a cross-sectional view showing an example of a blood sensor in the blood test apparatus of the present invention.

FIG. 8 is a cross-sectional view of the first example of the blood sensor. Blood sensor 42 shown in FIG. 8 has an outer shape of a round or polygon. Base plate 45 constituting blood sensor 42 has: substrate 46; spacer 47 stacked on the upper face of substrate 46; and cover 48 stacked on the upper face of spacer 47.

Blood storing part 49 is provided near the center of base plate 45. Storing part 49 is formed so as to communicate with hole 46a provided in substrate 46 and hole 47a provided in spacer 47. Storing part 49 opens downward to collect blood from the skin. The volume of storing part 49 is, for example, 0.904 µL, but is by no means particularly limited. One end of supply channel 50 is connected to storing part 49. The volume of supply channel 50 is, for example, 0.144 µL, but is by no means particularly limited. Detecting section 51 is arranged inside supply channel 50. Blood stored in storing part 49 flows into supply channel 50 by capillary action and is led to detecting section 51. The other end of supply channel 50 is connected to air hole 52. The diameter of air hole 52 may be approximately 50 µm to 250 µm. By making the diameter of air hole 52 small, blood is prevented from flowing out through air hole 52 excessively. Further, in a state where storing part 49 is in close contact with the skin, air hole 52 operates as a negative pressure path through which a negative pressure is created in storing part 49.

Reagent 53 mounted on detecting section 51 may be prepared as appropriate according to a test target. For example, reagent 53 is prepared by dropping a reagent solution on detecting section 51 arranged on substrate 46, and drying the reagent solution, wherein the reagent is prepared by adding and dissolving an enzyme (PQQ-GDH) of 0.1 to 5.0 U/sensor, potassium ferricyanide (10 to 200 mM), maltitol (1 to 50 mM) and taurine (20 to 200 mM) to a 0.01 to 2.0 wt % aqueous solution of CMC.

Storing part 49 of blood sensor 42 is sealed with face 49a (hereinafter "ceiling face"). The emitted laser light preferably transmits through ceiling face 49a, so that blood flowing out from the skin punctured with laser light does not flow out from ceiling face 49a. To allow the laser light to transmit through ceiling face 49a, cover 48 may be formed with the material that allows laser light to transmit (for example, glass or plastic such as polyimide).

Further, if the emitted laser light cannot transmit through ceiling face 49a, the laser light may perforate ceiling face 49a. In the case where the laser light perforates ceiling face 49a, substrate 46, spacer 47 and cover 48 may be formed with the same material.

The hole formed in ceiling face 49a can serve as air hole 52, as well as a negative pressure path through which the negative pressure means creates a negative pressure in storing part 49.

A Second Example of the Blood Sensor

Figure 9:
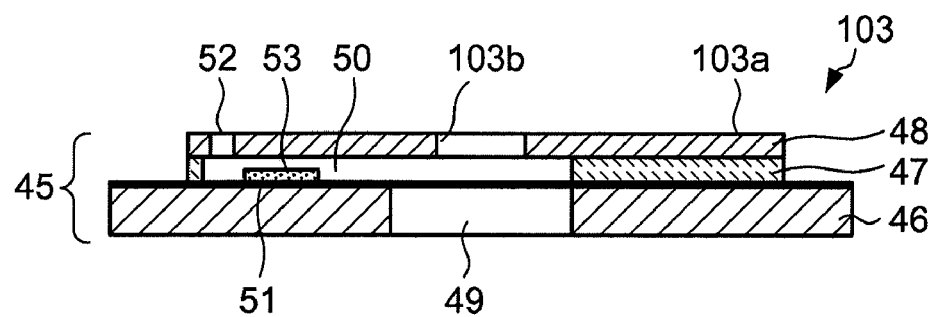
FIG. 9 is a cross-sectional view showing another example of the blood sensor in the blood test apparatus of the present invention.

FIG. 9 is a cross-sectional view of the second example of the blood sensor. While ceiling face 49a of storing part 49 of blood sensor 42 shown in FIG. 8 is sealed, the ceiling face of storing part 49 of blood sensor 103 shown in FIG. 9 is open.

Hole 103b is formed in cover 48 of blood sensor 103. Preferably, the diameter of hole 103b (for example, 1.0 mm) is smaller than the diameter of storing part 49 (for example, 2.0 mm), and is greater than the diameter of air hole 52 (50 µm to 250 µm). Hole 103b is preferably located in the center of the ceiling face of storing part 49. Laser light passes through hole 103b and punctures the skin. By providing hole 103b, it is possible to prevent laser light from declining. It is thereby possible to reduce the energy of laser light to be emitted.

Hole 103b and air hole 52 can serve as a negative pressure path through which negative pressure means 34 and 140 create a negative pressure in storing part 49.

Figure 10:
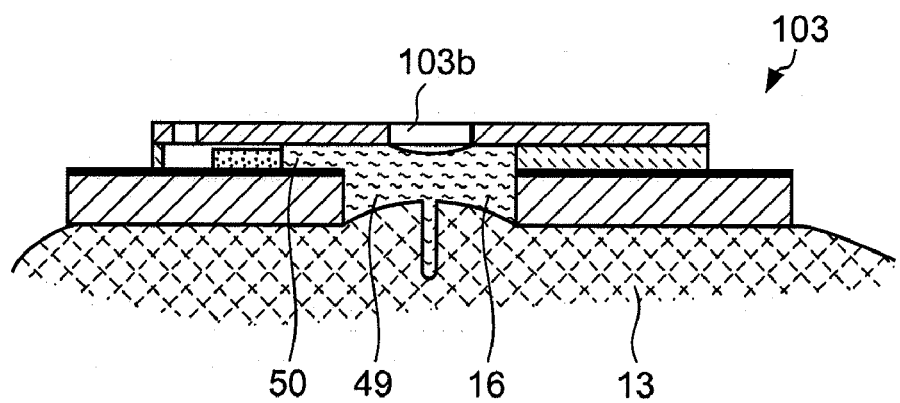
FIG. 10 is a cross-sectional view of the blood sensor of FIG. 9 upon puncturing.

As shown in FIG. 10, the surface tension of blood 16 generated inside hole 103b prevents blood 16 collected by puncturing the skin from overflowing out from the upper face of the cover. Blood 16 spreads through inside storing part 49. Therefore, it is possible to collect an adequate amount of blood 16. Blood 16 that fills storing part 49 flows into supply channel 50 by capillary action.

By making hole 103b is water-repellent, blood 16 is less likely to overflow through hole 103b. Therefore, the interior of the blood test apparatus is not contaminated with blood.

Polyethylene terephthalate (PET) can be used as the material of cover 48 of blood sensor 103, and the same material can be used as substrate 46 and spacer 47. Therefore, material control is simple.

Laser light passes through hole 103*b* of storing part 49, and laser light may pass through the center of hole 103*b* or pass through a position out of the center of hole 103*b*. For example, by making laser light pass through a position farther from supply channel 50 than the center of hole 103*b*, blood 16 flowing out from skin 13 fills the interior of storing part 49 completely, and then flows into supply channel 50, so that it is possible to realize accurate measurement.

Hole 103*b* is formed in advance in the ceiling face of storing part 49 of blood sensor 103. In this way, hole 103*b* is formed in advance, so that it is not necessary to adjust the axis of the laser light to the part to be perforated. Therefore, blood sensor 103 is easily attached to blood sensor unit 44. Hole 103*b* may be made small, approximately 0.05 to 0.25 mm, and preferably prevents blood 16 from flowing out through the puncturing hole.

As shown in FIG. 8 and FIG. 9, the blood sensors in the blood test apparatus of the present invention preferably has storing part 49 and supply channel 50. The inner wall surface of supply channel 50 is preferably hydrophilic so that blood is transferred smoothly to supply channel 50 where detecting section 51 is arranged. Further, the inner wall surface of supply channel 50 is preferably more hydrophilic than the inner wall surface of storing part 49 so that blood stored in storing part 49 is supplied to supply channel 50 smoothly.

Further, as shown in FIG. 8 and FIG. 9, the blood sensor in the blood test apparatus of the present invention has cover 48, and cover 48 forms the ceiling face of storing part 49. Upper faces 48*a* and 103*a* (faces irradiated with laser light) of cover 48 are preferably water-repellent. More particularly, upper faces 48*a* and 103*a* of cover 48 are preferably more water-repellent than the inner wall surface of storing part 49, so that blood stored in storing part 49 is prevented from flowing out through the hole (the hole perforated with laser light or hole 103*b*) formed on cover 48.

The Third Example of the Blood Sensor

The wetness of skin 13 of the patient varies depending on the environment. On the other hand, skin 13 to be punctured with laser light preferably has a certain level of moisture content. Therefore, in order to perform measurement in a stable, a certain level of wetness is preferably maintained by giving a certain level of moisture content to skin 13 by moistening the neighborhood of skin 13 before puncturing with laser light.

Figure 11:
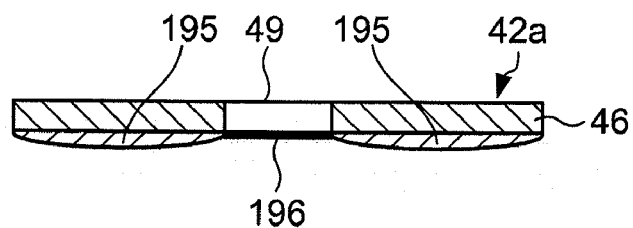
FIG. 11 is a cross-sectional view showing still another example of the blood sensor in the blood test apparatus of the present invention.

FIG. 11 shows blood sensor 42*a* provided with water storing part 195 that stores water, on the lower face side that comes into contact with on skin 13, of blood sensor 42 (see FIG. 8 in detail). On or before emitting laser light, water storing part 195 of blood sensor 42*a* shown in FIG. 11 breaks to splash a certain amount of water on skin 13 and moisten the skin which is lifted by negative pressure means 34 and 140 before laser light is emitted. Water storing part 195 may be, for example, a container which contains water and which is made of a plastic material such as PET, or a soft bag, a sponge or a spongy member that is soaked with water. Water storing part 195 is preferably not arranged in transmission part 196 through which laser light passes, because the intensity of the laser light is reduced by water.

Transparent Plan View 1 of the Blood Sensor

Figure 12:
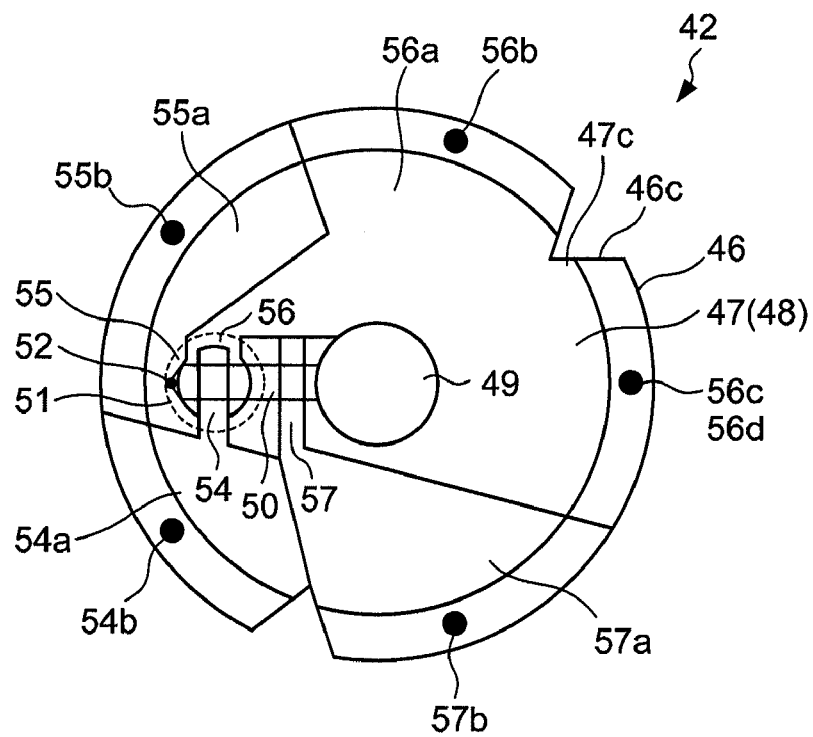
FIG. 12 is a transparent plan view of the blood sensor of FIG. 8.

FIG. 12 is a perspective plan view of blood sensor 42. In blood sensor 42, detection electrodes 54 to 57 are arranged, and in order from storing part 49 toward air hole 52, detection electrode 57 (Hct (hematocrit) electrode), detection electrode 56 (counter electrode), detection electrode 54 (active electrode), detection electrode 56 (counter electrode) and detection electrode (sensing electrode) are arranged. Detection electrodes 54 to 56 are arranged in detecting section 51.

Detection electrodes 54 to 57 are connected to connection electrodes 54*a* to 57*a*, respectively. Connection electrodes 54*a* to 57*a* extend up to the outer periphery of substrate 46. Contact parts 54*b* to 57*b* are provided in connection electrodes 54*a* to 57*a*. Further, in connection electrode 56*a*, contact part 56*c* is also provided in addition to contact part 56*b*, so that two contact parts are provided. Reference electrode 56*d* may be provided in connection electrode (54*a*, 55*a* and 57*a*) other than connection electrode 56*a*. Contact parts 54*b* to 57*b* and contact part 56*c* are arranged near the outer periphery of sensor 42 at virtually regular intervals.

Among contact parts 54*b* to 57*b* and 56*c*, contact part 56*b* and contact part 56*c* electrically conduct with each other, and the other contact parts are insulated from each other. The connection electrodes can be specified using contact part 56*c* as a reference contact part, that is, reference electrode 56*d*. That is, the insulation resistance between the neighboring contact parts is measured by electrical circuit section 36 (see FIG. 2), and a contact part where the insulation resistance is zero is identified as reference electrode 56*d*. Based on reference electrode 56*d*, connection electrodes 56*a*, 57*a*, 54*a* and 55*a* are specified clockwise.

In this way, blood sensor 42 has reference electrode 56*d*, so that it is possible to specify the connection electrodes. Therefore, even if the contact parts (54*b* to 57*b* and 56*c*) are connected casually to the five connectors arranged in apparatus body 39, it is possible to specify the connection electrodes and perform measurement. Accordingly, blood sensor 42 (or blood sensor unit 44 including blood sensor 42) can be made in a symmetrical shape so that blood sensor 42 can be attached to apparatus body 39 casually in a very simple manner.

Aligning concave part 46*c* may be provided on the outer periphery of substrate 46. On the outer peripheries of spacer 47 and cover 48, aligning concave parts 47*c* and 48*c* are provided so as to correspond to aligning concave part 46*c*. By using aligning concave parts 46*c* to 48*c*, blood sensor 42 can be attached to blood sensor unit 44 so as to meet a predetermined alignment of blood sensor unit 44.

Transparent Plan View 2 of the Blood Sensor

Figure 13:
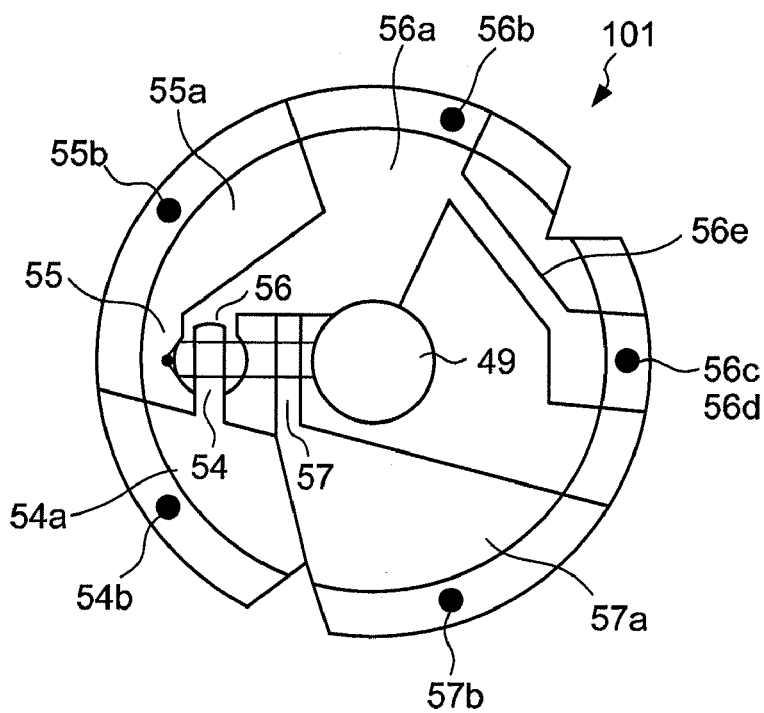
FIG. 13 is a transparent plan view showing still another example of the blood sensor in the blood test apparatus of the present invention.

FIG. 13 is a transparent plan view of a round blood sensor. Blood sensor 101 shown in FIG. 13 is different from blood sensor 42 (see FIG. 12) in that reference electrode 56*d* is formed via a predetermined pattern from connection electrode 56*a*. The difference will be mainly described below.

Reference contact part 56*c* is provided in reference electrode 56*d*. Reference contact part 56*c* and contact parts 54*b* to 57*b* are arranged near the outer periphery at regular intervals. That is, contact parts 54*b*, 55*b*, 56*b*, 56*c* and 57*b* are arranged at apexes of a regular pentagon.

Connection electrode 56*a* and reference electrode 56*d* are connected via laser-machined pattern 56*e*. By changing the width of pattern 56*e*, the resistance value between contact part 56*b* and reference contact part 56*c* can be changed. Reference electrode 56*d* serves as a reference for specifying the positions of connection electrodes 54*a* to 57*a*.

Reference electrode 56*d* can be utilized to identify the product specifications of blood sensor 101. For example, the blood test apparatus is set so that calibration curve 1 is used when the resistance value of pattern 56*e* is 200 to 1000 ohms, calibration curve 2 is used when the resistance value is 1000 to 2000 ohms, and calibration curve 3 is used when the resistance value is 2000 to 3000 ohms, the calibration curve of the sensor is recognized automatically, and the blood sugar level is measured using an appropriate calibration curve. The reference electrode can be used to identify various product specifications, in addition to use in automatic recognition of the calibration curve. For example, the reference electrode can be used to identify the users the product is shipped to, for example, to identify whether the product has the specifications for company A or the specifications for company B.

By forming pattern 56e with an inductance having arbitrary property, connecting the inductance to a resonator constituting an oscillator and changing the oscillation frequency according to this inductance property, various information can be provided.

By providing reference electrode 56d, even when blood sensor unit 44 is attached to blood test apparatuses 31 or 31a at an arbitrary rotation angle with respect to the axis of the attaching direction, connection electrodes 54a to 57a can be specified. Therefore, when blood sensor unit 44 is attached, the attaching direction does not have to be adjusted visually, so that it is possible to attach blood sensor unit 44 in a simple manner.

Transparent Plan View 3 of the Blood Sensor

Figure 14:
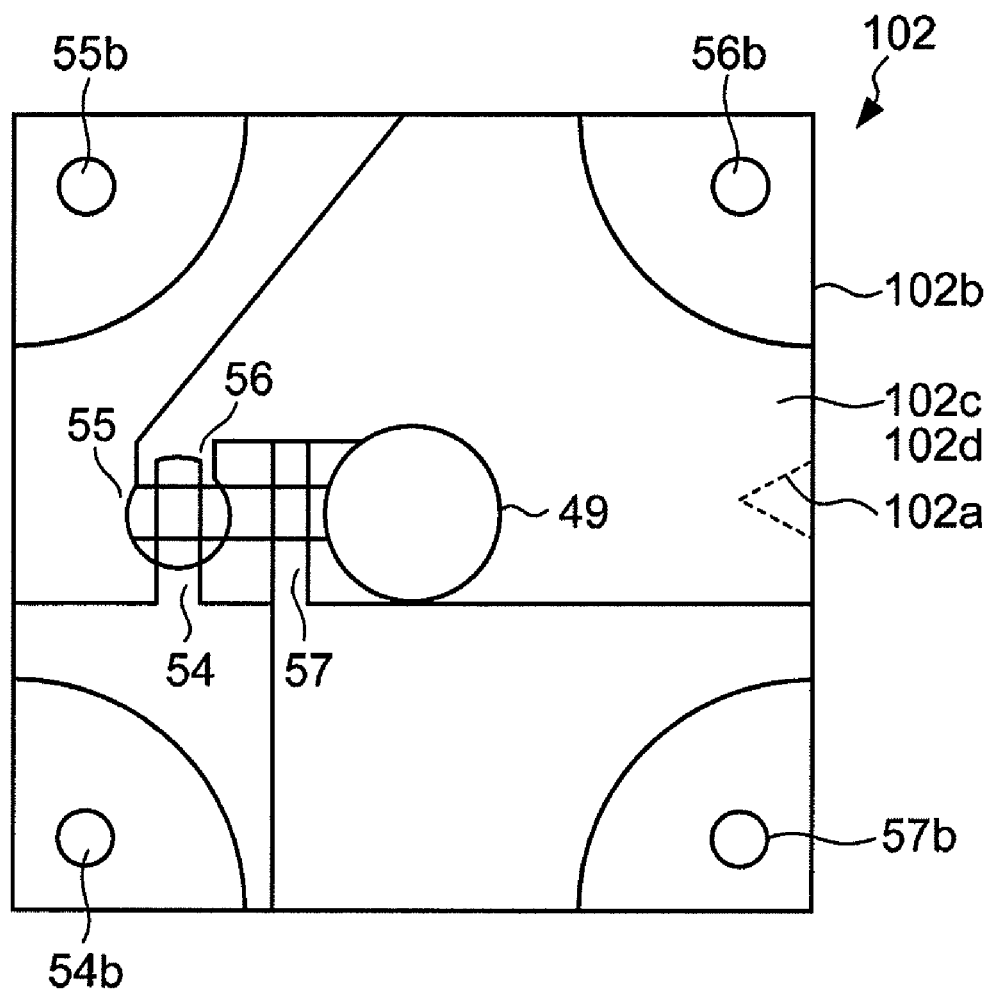
FIG. 14 is a transparent plan view showing still another example of the blood sensor in the blood test apparatus of the present invention.

FIG. 14 is a transparent plan view of a square-shaped blood sensor. Although the outer shape of blood sensor 102 shown in FIG. 14 is a square, the outer shape may be a polygonal such as a hexagon and octagon. By forming blood sensor 102 in a square or hexagonal shape, the yield rate of material preparation improves. Further, as shown in FIG. 14, aligning concave part 102a for aligning blood sensor unit 44 may be provided in one of the four sides of blood sensor 102, in such a case blood sensor 102 has an asymmetrical shape. Concave part 102a serves as the reference when blood sensor 102 is attached to blood sensor unit 44. Further, by alignment blood sensor unit 44 and adapter 40 by using convex part 130f (see FIG. 25) in the blood sensor unit 44 side that engages with concave part 102a as a reference, detection electrodes 54 to 57 can be specified even if reference electrode 56d is not provided.

Contact parts 54b to 57b are provided in the corners of square-shaped substrate 102b. Spacer 102c and cover 102d are stacked on substrate 102b. Substrate 102b corresponds to substrate 46, spacer 102c corresponds to spacer 47, and cover 102d corresponds to cover 48 (see FIG. 8).

An Exploded Plan View of the Blood Sensor

An assembly and material of blood sensor 42 (see FIG. 8) provided in the blood test apparatus of the present invention will be described.

Figure 15A:
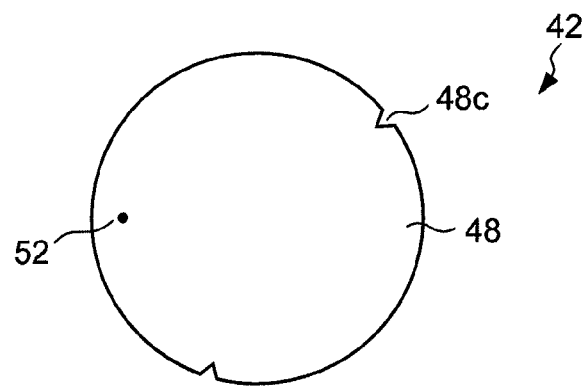
FIG. 15A shows a plan view of the cover.
Figure 15B:
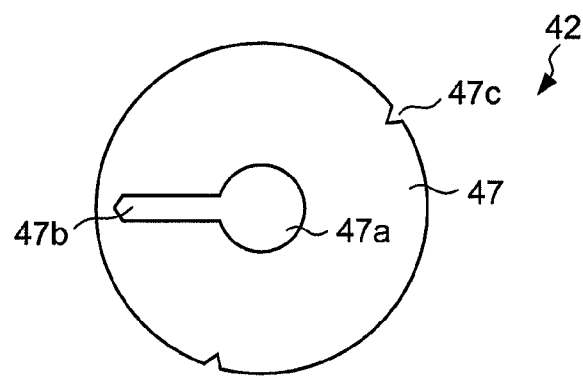
FIG. 15B shows a plan view of the spacer.
Figure 15C:
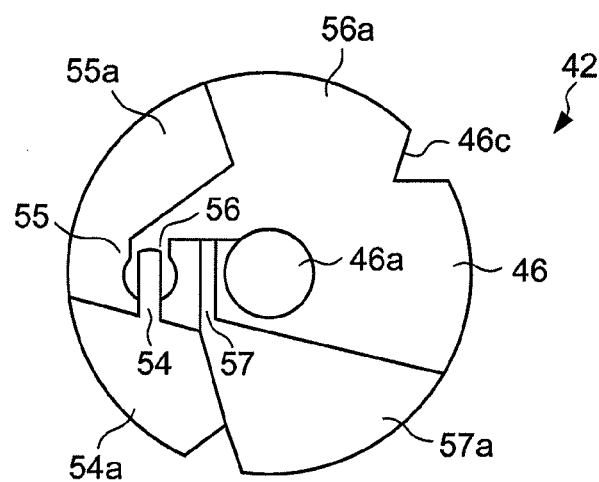
FIG. 15C shows a plan view of the substrate.

FIG. 15 is an exploded plan view of blood sensor 42. FIG. 15A is a plan view of cover 48, FIG. 15B is a plan view of spacer 47, and FIG. 15C is a plan view of substrate 46.

FIG. 15C is a plan view of round substrate 46 constituting blood sensor 42. The diameter of substrate 46 may be approximately 8.0 mm. The material of substrate 46 is resin such as polyethylene terephthalate (PET), and its thickness may be 0.075 to 0.250 mm (for example, 0.188 mm).

On the upper face of substrate 46, detection electrodes 54 to 57, and connection electrodes 54a to 57a derived from detection electrodes 54 to 57, respectively, are formed in an integrated manner. These detection electrodes and connection electrodes may be formed by applying laser processing to a conductive layer formed with the sputtering method or the vapor deposition method. The material of the conductive layer can be gold, platinum and palladium as materials.

The diameter of hole 46a provided near the center of substrate 46 may be approximately 2.0 mm. Preferably, the wall surface of hole 46a is less hydrophilic than supply channel 50 or is less water-repellent than upper face 48a of cover 48.

Hole 46a is preferably formed by punching press substrate 46 from the side of detection electrodes 54 to 57, using a convex mold, because it is less likely to damage detection electrodes 54 to 57. Further, even if a burr is produced in hole 46a by this punching, the burr is oriented downward (toward the skin). Therefore, blood 16 is prevented from flowing out from storing part 49. Concave part 46c for aligning provided on the outer periphery of substrate 46 engages with a aligning convex part formed in cylindrical body 41e of blood sensor unit 44 (see FIG. 16). The alignment where blood sensor 42 is attached to blood sensor unit 44 is thereby determined.

FIG. 15B is a plan view of spacer 47. The diameter of spacer 47 may be approximately 5.2 mm. The material of spacer 47 is resin such as polyethylene terephthalate, and its thickness may be 0.025 to 0.25 mm (for example, 0.1 mm).

The diameter of hole 47a provided near the center of spacer 47 is 2.0 mm, and hole 47a is provided in the position corresponding to hole 46a provided in substrate 46. Preferably, the wall surface of hole 47a is less hydrophilic than supply channel 50 or is less water-repellent than upper face 48a of cover 48. Storing part 49 is constituted with hole 46a and hole 47a.

Slit 47b is formed toward the outer periphery from hole 47a. Slit 47b serves as blood supply channel 50. The wall surface of slit 47b and the upper face of substrate 46 corresponding to the wall surface of slit 47b are subjected to hydrophilicity treatment. Further, the width of slit 47b may be approximately 0.6 mm, and the length may be approximately 2.4 mm. As a result, the volume of supply channel 50 is approximately 0.144 µL. Therefore, by making the volume of supply channel 50 small, test can be performed with a small amount of blood, so that the load on the patient becomes small and the patient does not feel fear.

Concave part 47c for aligning provided on the outer periphery of spacer 47 is formed in the position meeting concave part 46c for aligning provided in substrate 46.

FIG. 15A is a plan view of cover 48. The diameter of cover 48 may be approximately 5.2 mm. The thickness of cover 48 may be approximately 0.050 to 0.125 mm (for example, 0.075 mm).

Cover 48 can be made of a material that does not absorb laser light. Examples of the material of cover 48 include glass and plastic such as polyimide. When laser light is not absorbed in cover 48, the laser light can pass through ceiling face 49a of storing part 49 to puncture the skin. The laser light does not perforate ceiling face 49a, and so blood 16 does not flow out through the hole, and blood 16 does not flow into apparatus body 39.

Cover 48 may be made of a material that absorbs laser light. In this case, cover 48 may be perforated by the emitted laser light, or a hole through which laser light passes, may be formed in cover 48 before the laser light is emitted.

Air hole 52 is provided to meet the tip part of supply channel 50. The diameter of air hole 52 is 50 µm.

Upper face 48a (see FIG. 8) of cover 48 that forms the upper face of substrate 45 is preferably subjected to water-repellency treatment. The ceiling face of supply channel 50 is preferably subjected to hydrophilicity treatment. Further, preferably, ceiling face 49a of storing part 49 is subjected to weaker hydrophilicity treatment than supply channel 50 or is subjected to weaker water-repellency treatment than upper face 48a of cover 48.

Hydrophilicity may be reduced by, for example, removing the hydrophilic agent applied on a hydrophobic member to increase hydrophobicity. The hydrophilic agent is removed by, for example, decomposing the hydrophilic agent through UV (ultraviolet ray) irradiation. The hydrophobic material can be directly used as the material of ceiling face 49a of storing part 49.

The material may be made water-repellent by mixing a water-repellent agent in the material. Further, the material may be made water-repellent by applying an appropriate amount of water-repellent agent on the surface of the hydrophilic material. The level of water-repellency may be adjusted by adjusting the amount of the water-repellent agent to be mixed.

The hydrophilicity or water-repellency of the components of blood sensor 42 can be adjusted as follows. Upper face 48a of cover 48 is subjected to water-repellency treatment in advance. On the other hand, the overall lower face of cover 48 is subjected to hydrophilicity treatment. The lower face of cover 48 includes the ceiling face of supply channel 50. Next, substrate 46, spacer 47 and cover 48 are stacked. After substrate 46, spacer 47 and cover 48 are stacked, the hydrophilic material of ceiling face 49e may be dissolved and removed by radiating short-wavelength UV from the opening of storing part 49. By manufacturing blood sensor 42 as described above, it is possible to make upper face 48a of cover 48 water repellent and make the inner face of supply channel 50 hydrophilic. Further, the inner face of storing part 49 may be less hydrophilic than supply channel 50 and less water repellent than upper face 48a.

The ratio of the thickness of substrate 46 (0.188 mm), the thickness of spacer 47 (0.100 mm) and the thickness of cover 48 (0.075 mm) is approximately, 2.5:1.3:1. By this means, it is possible to form storing part 49 that can pool a sufficient amount of blood while making blood sensor 42 thinner. Further, by the thickness of spacer 47 (0.100 mm), the effect of capillary action in supply channel 50 can be obtained sufficiently.

In blood sensor 42, the ratio of the volume of storing part 49 (0.904 μL) and the volume of supply channel (0.144 μL) may be approximately 6:1, but the ratio is not particularly limited. By this means, test does not become incorrect, even when the amount of blood 16 is small. Further, the volume of storing part 49 is not too large with respect to the volume of supply channel 50 required, so that a large amount of blood 16 does not flow into supply channel 50 and does not wash away reagent 53 (see FIG. 8). Therefore, the rate of flow of blood 16 becomes constant, which does not generate variation in concentration of reagent 53, so that it is possible to examine blood 16 accurately.

Further, the amount of blood 16 collected is set a very small amount which is a sufficient amount required for a test of blood 16. Only blood 16 of approximately six times the volume of supply channel 50 is collected. Therefore, it is possible to reduce the load on the patient significantly. In view of the collection amount of blood 16 for accurate measurement and the collection amount of blood 16 for reducing the load on the patient, the volume of storing part 49 is preferably more than five times and less than seven times the volume of supply channel 50.

The Blood Sensor Unit

The blood sensor in the blood test apparatus of the present invention may be included in the blood sensor unit. The blood sensor unit can be attached to and removed from the apparatus body and is a replaceable member.

Figure 16:
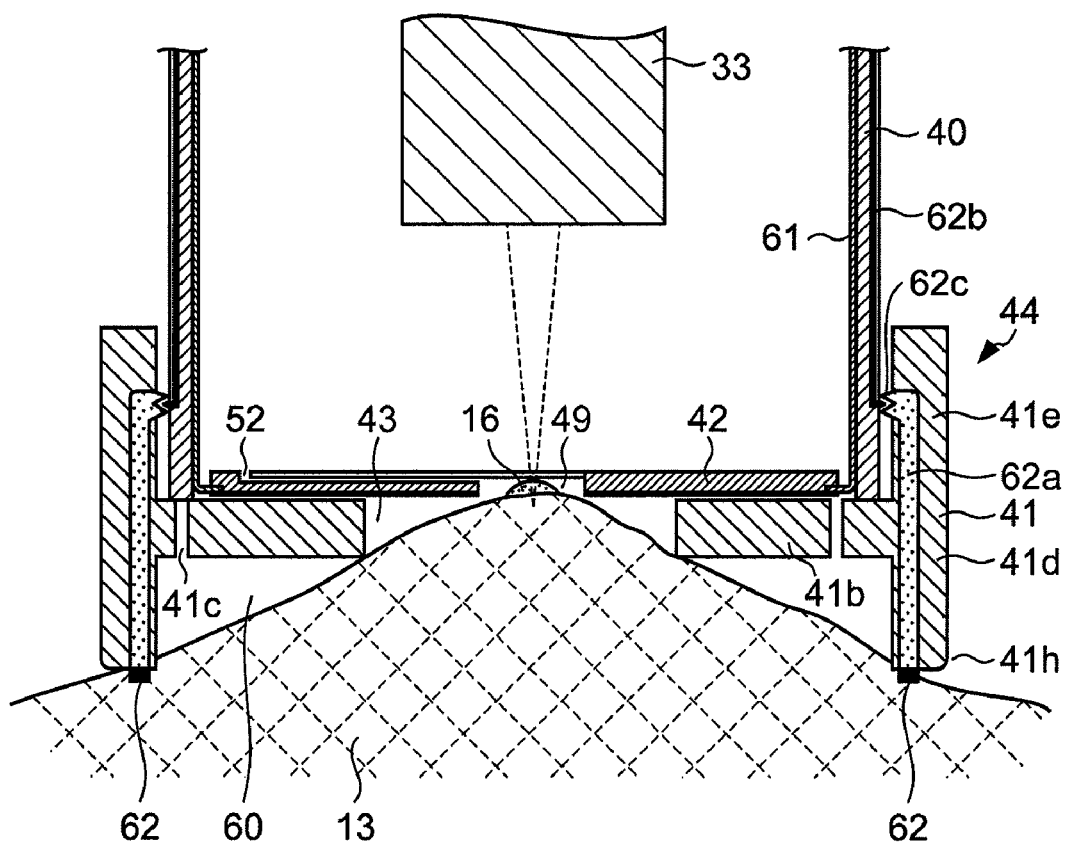
FIG. 16 is a cross-sectional view showing a blood sensor unit and its neighborhood in the blood test apparatus of the present invention.

FIG. 16 is a cross-sectional view of blood sensor unit 44 and the neighborhood of blood sensor unit 44. The cross section of blood sensor unit 44 is configured in the shape of "H" by cylinder-shaped holder 41 that opens upward and downward, and attaching part 41b that is provided so as to seal the interior of holder 41.

The material of holder 41 is preferably resin that is applicable to injection molding, including ABS resin, AS resin and thermoplastic resin such as polyethylene, polypropylene, polyvinyl chloride and polyethylene terephthalate, or thermosetting resin such as phenol resin, epoxide resin and silicon resin.

Blood sensor 42 is attached to attaching part 41b. Blood sensor 42 can be attached and removed. Although, in FIG. 16, blood sensor 42 is attached to an upper side (the laser emitting apparatus 33 side) of attaching part 41b, blood sensor 42 may be attached to a lower side (the punctured skin 13 side) of attaching part 41b.

In the center of attaching part 41b, window 43 is preferably provided so as to correspond to storing part 49. The area of the opening part of window 43 is preferably larger than the area of the opening part of storing part 49. Further, negative pressure path 41c is provided that penetrates the upper side and the lower side of attaching part 41b. Negative pressure path 41c may be provided, for example, between the outer periphery of blood sensor 42 and the inner periphery of holder 41.

Cylindrical body 41d located below attaching part 41b forms negative pressure chamber 60 between skin 13 and cylindrical body 41d. Further, the inner wall of cylindrical body 41e located above attaching part 41b of blood sensor unit 44 is latched outside adapter 40.

Connector 61 is provided inside adapter 40. Connector 61 includes a plurality of (for example, five) individual connectors 61a to 61e. When blood sensor unit 44 is attached to adapter 40, connectors 61a to 61e contact with contact parts 54b to 57b and 56c of blood sensor 42, respectively. Signals of connectors 61a to 61e are led to electrical circuit section 36.

First skin contact sensor 62 provided at tip 41h of cylindrical body 41d detects skin 13 when blood sensor unit 44 comes into contact with skin 13. First skin contact sensor 62 also connects to connection part 62c provided in adapter 40 via conductor 62a arranged inside holder 41, and further connects to conductor 62b at the adapter 40 side. Conductor 62b is led to electrical circuit section 36.

A plurality of (for example, two) first skin contact sensors 62 made of conductors are preferably provided in different parts in tip 41h of cylindrical body 41d (in FIG. 16, two first skin contact sensors 62 are provided symmetrically with respect to the center of cylindrical body 41d). By measuring the resistance value between two conductors of first skin contact sensor 62, skin 13 is detected when blood sensor unit 44 comes into contact with skin 13. Therefore, it is possible to detect skin 13 when the tip of blood sensor unit 44 comes into contact with skin 13 completely without space. Laser light is preferably not allowed to emit unless first skin contact sensor 62 detects a contact with the skin. First skin contact sensor 62 may be a mechanical micro switch or a reflection optical switch.

By emitting laser light from laser emitting apparatus 33, blood capillaries in skin 13 are damaged by the laser light, and blood 16 flows out. The outflow of blood 16 is stored in storing part 49.

Figure 17:
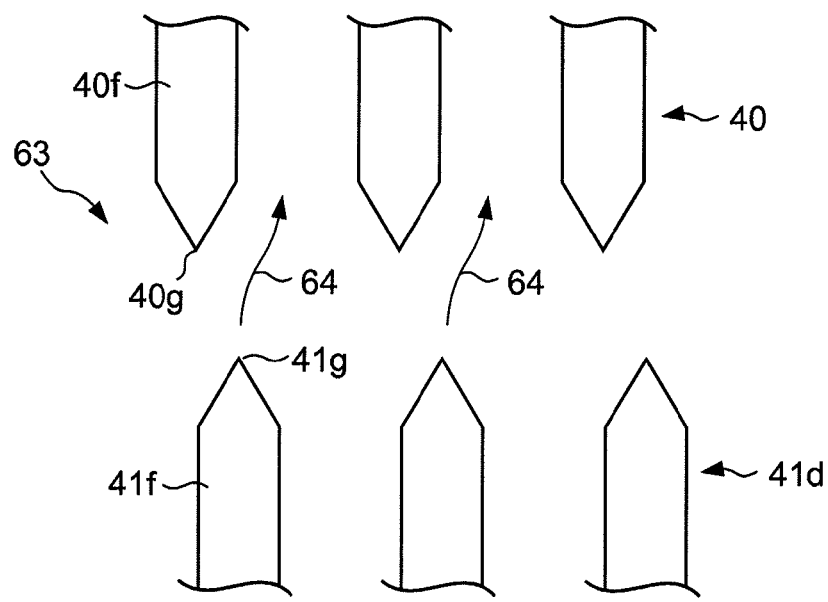
FIG. 17 is an exploded elevation view showing the primary part of a guide part for attaching the blood sensor unit to the blood test apparatus of the present invention.

A guide part for attaching blood sensor unit 44 in a simple manner may be provided in cylindrical body 41d and adapter 40 of blood sensor unit 44. FIG. 17 is an exploded elevation view of the primary part of guide part 63 that guides insertion of blood sensor unit 44 into adapter 40. Convex part 41f is formed inside cylindrical body 41d, and convex part 40f is formed outside adapter 40. Tip part 41g and tip part 40g, which are the tips of convex part 41f and convex part 40f, respectively, are made sharp. Tip part 41g and tip part 40g face each other. Convex part 40f and its tip part 40g, and convex part 41f and its tip part 41g, constitute guide part 63.

When blood sensor unit 44 is inserted into adapter 40, even when the relative alignment between blood sensor unit 44 and adapter 40 is out of predetermined alignment, blood sensor unit 44 is inserted along guide part 63 while correcting the course (see arrow 64). As a result, connectors 61a to 61e provided in adapter 40 are sure to contact with one of contact parts 54b to 57b and 56c provided in sensor 42. Therefore, blood sensor unit 44 can be inserted without taking into account the rotation angle with respect to the axis of the insertion direction, so that blood sensor unit 44 can be attached in a simple manner.

Figure 18:
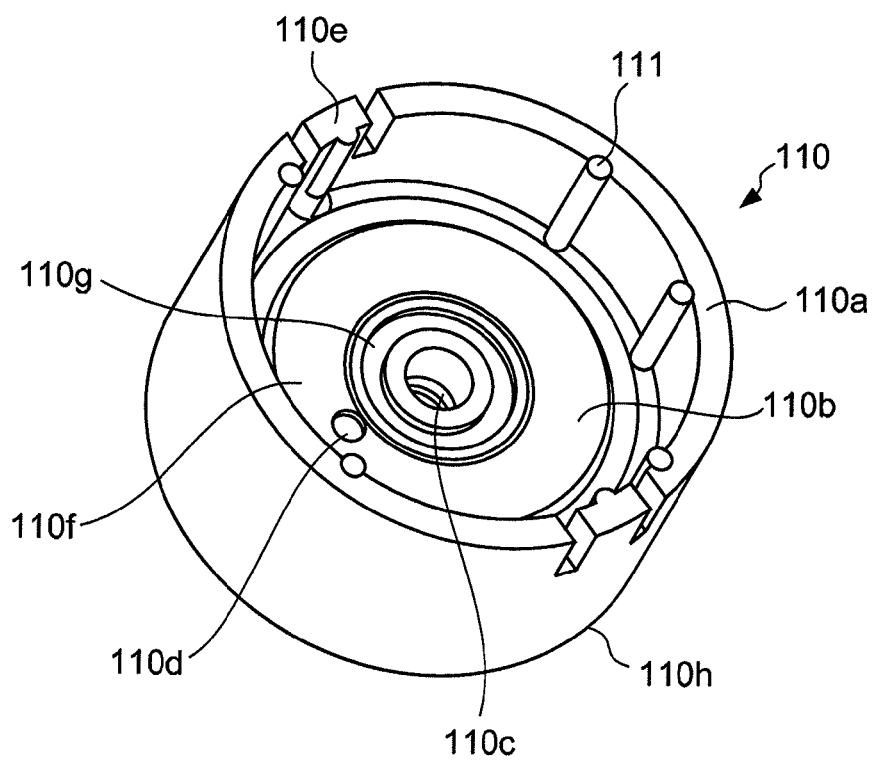
FIG. 18 is a perspective view showing an example of the blood sensor unit in the blood test apparatus of the present invention.

FIG. 18 is a diagrammatic perspective view of the blood sensor unit. Blood sensor unit 110 shown in FIG. 18 may have the same structure as blood sensor unit 44 unless described otherwise. Blood sensor unit 110 has the shape of a cylinder, and its cross section has the shape of "H." Five connectors 111 that transmit signals of the contact part of the blood sensor (one of blood sensors 42, 101, 102 and 103) to electrical circuit section 36 may be provided inside holder 110a of blood sensor unit 110 (in the case of blood sensor 102, four connectors may be provided). Connector 111 connects to adapter 40 at an upper end of holder 110a and is led to electrical circuit section 36 via this adapter 40. Connector 111 may be provided in the adapter and may be connected with the contact part of the blood sensor of blood sensor unit 110.

Blood sensor 42 is attached on the reverse side (the lower end 110h side, that is, the side the punctured skin is arranged) of attaching part 110b provided so as to seal the opening of holder 110a. Window 110c provided near the center of attaching part 110b is provided so as to meet the position of storing part 49 of blood sensor 42. Laser light passes through window 110c and storing part 49 and punctures skin 13.

Air hole 110d provided in attaching part 110b is provided in the position meeting air hole 52 of blood sensor 42. Air hole 110d is provided so that blood 16 runs into supply channel 50 of blood sensor 42 or create a negative pressure in storing part 49.

Engaging part 110e of blood sensor unit 110 engages with adapter 40 via the elasticity of engaging part 110e which engages with adapter 40. Two engaging parts 110e that face each other are provided in holder 110a. Engaging parts 110e have slits on both sides so as to have elasticity, and are formed integrated with holder 110a. Therefore, engaging parts 110e can be made at a low cost.

Deodorizing member storage 110f is provided on the upper face of attaching part 110b in a concentric fashion. A deodorizing member is placed on deodorizing member storage 110f. When the skin is punctured with laser light, cases occur where skin 13 is carbonized and produces an odor. This odor can be deodorized with the deodorizing member (such as deodorant agent). Further, blood pool 110g is provided on the upper face of attaching part 110b in a concentric fashion. Therefore, even if blood 16 overflows from hole 103b of blood sensor 103 (see FIG. 10), blood 16 stays in blood pool 110g, so that it is possible to prevent blood 16 from contaminating the body part of blood test apparatuses 31 or 31a.

Figure 19:
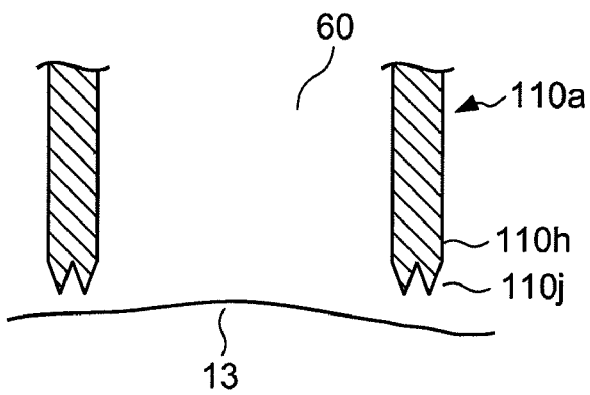
FIG. 19 is a cross-sectional view of the primary part of one configuration example showing the neighborhood of the lower end of a holder in the blood sensor unit of FIG. 18.

FIG. 19 is a cross-sectional view showing the primary part of one configuration example of neighborhood of lower end 110h of holder 110a. An end part of lower end 110h comes into contact with skin 13 of the patient and forms negative pressure chamber 60. Lower end 110h needs to closely contact with skin 13. Therefore, lower end 110h may be formed with two concentric lines 110j which are made sharp at an acute angle. Since line 110j comes into contact with skin 13 reliably by line contact, negative pressure chamber 60 is kept sealed. The number of lines 110j does not have to be two, and there may be one or a plurality of lines 110j.

Further, if a capillary function is given to a groove formed between two concentric lines 110j, over-sampled blood 16 after measurement is sucked in the groove. Therefore, it is not necessary to prepare paper for wiping off blood flowing out.

Figure 20:
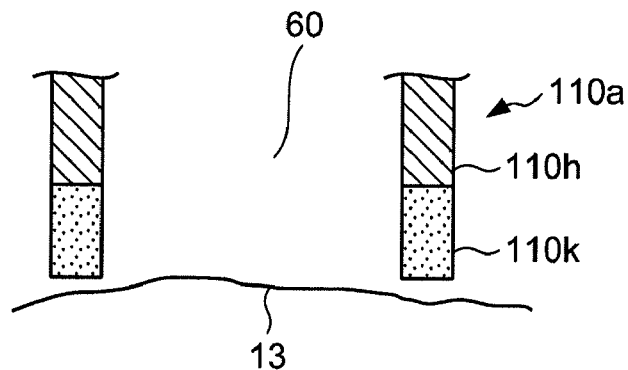
FIG. 20 is a cross-sectional view of the primary part of another configuration example showing the neighborhood of the lower end of the blood sensor unit in the blood test apparatus of the present invention.

FIG. 20 is a cross-sectional view showing the primary part of another configuration example near lower end 110h of holder 110a. Concentric contacting part 110k made of elasticity such as rubber, silicon, urethane and a sponge, is formed in lower end 110h. Therefore, contacting part 110k can come into close contact with skin 13 by its elasticity, and negative pressure chamber 60 is kept sealed. The contact surface of contacting part 110k is preferably a flat to increase the area where contacting part 110k comes into contact with skin 13.

By forming contacting part 110k with an absorbing member, such as a sponge, that has absorbency, it is possible to wipe off over-sampled blood 16 flowing out by puncturing after measurement. Therefore, it is not necessary to prepare wiping paper. Further, if an antiseptic is applied to the absorbing member, the absorbing member becomes sanitary.

Figure 21:
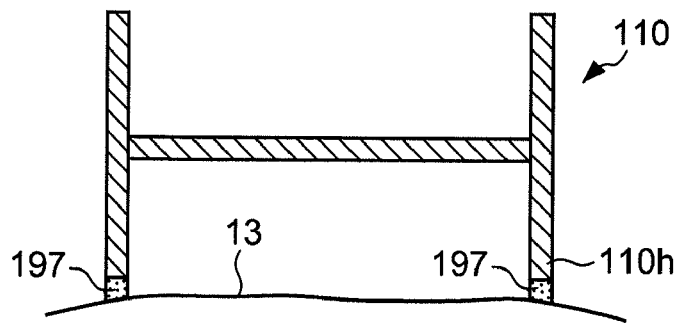
FIG. 21 is a cross-sectional view of the primary part of still another example showing the neighborhood of the lower end of the blood sensor unit in the blood test apparatus of the present invention.

The wetness of skin 13 changes with the external environment such as seasons. Therefore, the wetness near skin 13 to be punctured is preferably maintained constant. Therefore, before puncturing, measurement may be performed in a stable condition by providing an adequate level of moisture content to skin 13 and moistening the skin. Therefore, as shown in FIG. 21, it is also possible to provide water storing part 197 which is soaked with water, throughout the perimeter of lower end 110h of holder 110a of blood sensor unit 110, soak skin 13 near the part to be punctured with water in advance and puncture skin 13 with laser light. Water storing part 197 may be a porous body that has elasticity such as a sponge.

Figure 22:
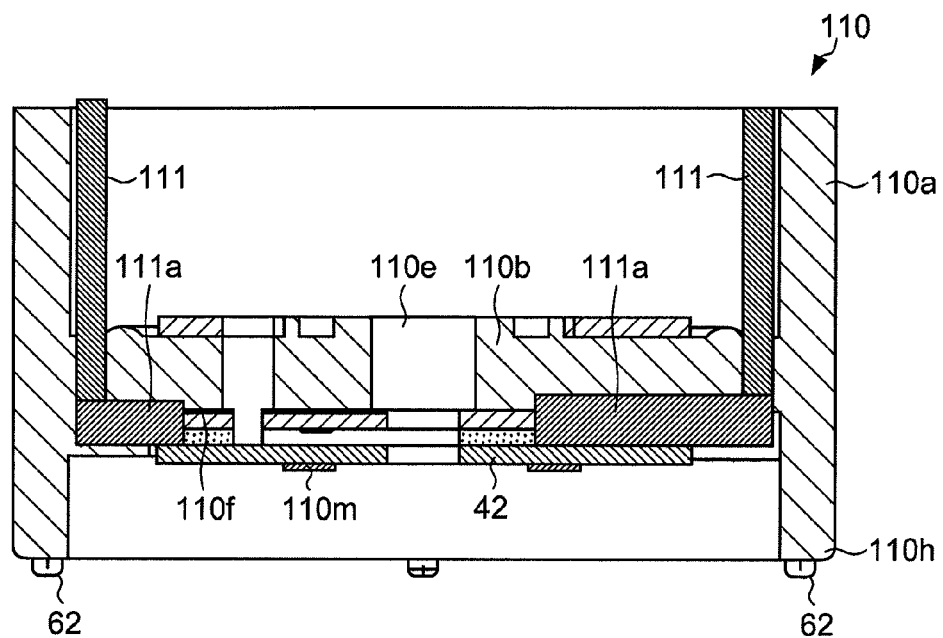
FIG. 22 is a cross-sectional view of the blood sensor unit of FIG. 18.

FIG. 22 is a cross-sectional view of blood sensor unit 110. As shown in FIG. 22, blood sensor 42 is arranged in the lower face of attaching part 110b of blood sensor unit 110 and is held by attaching part 110b. Skin 13 is lifted by negative pressure means 34 or 140 (see FIG. 2 and FIG. 3) and is in close contact with blood sensor 42. Blood sensor 42 is held by attaching part 110b, and so is less likely to be distorted by skin 13 that is in close contact with blood sensor 42. Connectors 111 contact with contact parts 54b to 57b and 56c of blood sensor 42. Guide part 63 (see FIG. 17) matching adapter 40 is preferably provided in holder 110a.

The blood test apparatus of the present invention has a negative pressure means, the negative pressure means create a negative pressure inside blood sensor unit 110. As a negative pressure path, groove 110f may be formed in attaching part 110b of blood sensor unit 110. Groove 110f extends to window 110e formed near the center of attaching part 110b, from the outer periphery side of attaching part 110b of holder 110a. When a negative pressure is created, a negative pressure is also created in groove 110f, and blood sensor 42 is in close contact with attaching part 110b. When the negative pressure is released to the atmosphere, blood sensor 42 is removed from attaching part 110b. Connector 111 contacts with blood sensor 42 in contact surface 111a. Connector 111 is integrated with holder 110a and formed so as to cut into part of attaching part 110b. By this means, the contact parts of the connection electrodes formed on the upper face of blood sensor 42 connect with contact parts (not shown) provided in connectors 111.

Second skin contact sensor 110m may be provided in the lower face of blood sensor 42. By this means, skin 13 is detected when skin 13 comes into contact with second skin contact sensor 110m by the negative pressure in negative pressure chamber 60. Second skin contact sensor 110m may be, for example, configured with a counter electrode. Laser light emission is preferably not allowed unless second skin contact sensor 110m detects a contact with the skin. Negative pressure means 34 may stop creating a negative pressure in negative pressure chamber 60 when second skin contact sensor 110*m* detects the contact with the skin. By controlling negative pressure means 34 in this way, negative pressure means 34 can be controlled without wasting a negative pressure power.

Further, first skin contact sensor 62 may be provided in lower end 110*h* of holder 110*a*.

Figure 23:
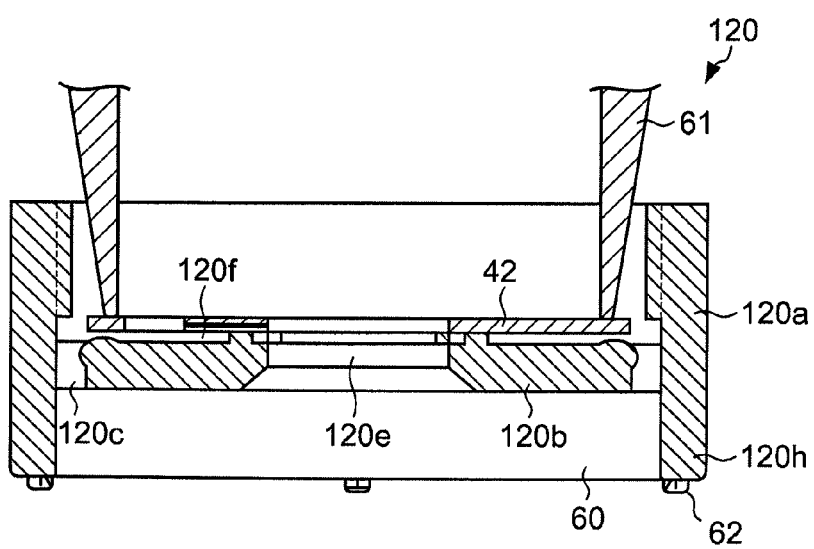
FIG. 23 is a cross-sectional view showing another example of the blood sensor unit in the blood test apparatus of the present invention.

FIG. 23 is a cross-sectional view of another blood sensor unit. Blood sensor unit 120 shown in FIG. 23 may have the same structure as blood sensor unit 110 unless described otherwise. Blood sensor unit 120 is different from blood sensor unit 110 in that blood sensor 42 is mounted on the upper side of attaching part 120*b* formed so as to seal the opening of holder 120*a*. Connector 61 connected to electrical circuit section 36 conducts with contact part (54*b* to 57*b* and 56*c*) of blood sensor 42.

The upper space and the lower space in attaching part 120*b* of blood sensor unit 120 having an H-shaped cross section, communicate through negative pressure path 120*c*. The lower space forms negative pressure chamber 60. First skin contact sensor 62 is provided in lower end 120*h* of holder 120*a*. Further, second skin contact sensor 120*m* is provided in the lower face of attaching part 120*b* (not shown).

By attaching blood sensor 42 on the upper face of attaching part 120*b*, it is possible to increase the contact pressure between connector 61 and the contact part (54*b* to 57*b* and 56*c*) of blood sensor 42. Further, it is possible to attach blood sensor 42 to attaching part 120*b* in a simple manner.

The space on the side of apparatus body 39 (the upper space in the figure) and the space on the side of skin 13 (the lower space in the figure) separated by blood sensor 42 and attaching part 120*b*, communicate with each other via negative pressure path 120*c*. On creating a negative pressure on skin 13, it is possible to create a negative pressure in the space on the side of skin 13 via this negative pressure path 120*c*. Further, when a negative pressure is released to the atmosphere, airflows into space on the side of apparatus body 39 quickly via negative pressure path 120*c*. Therefore, it is possible to prevent blood led in blood sensor 42 from splashing to apparatus body 39.

Groove 120*f* may be formed on the upper side of attaching part 120*b* as a negative pressure path. Groove 120*f* extends from the outer periphery of attaching part 120*b* of holder 120*a* to window 120*e* formed near the center of attaching part 120*b*. Providing groove 120*f* makes it unnecessary to provide a hole (negative pressure path 120*c*) which penetrates attaching part 120*b*.

Figure 24:
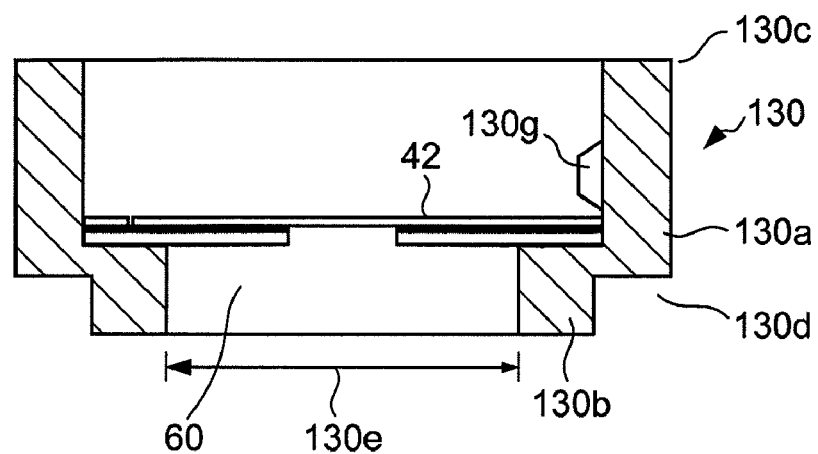
FIG. 24 is a cross-sectional view showing still another example of the blood sensor unit in the blood test apparatus of the present invention.

FIG. 24 is a cross-sectional view of another blood sensor unit. Blood sensor unit 130 shown in FIG. 24 may have the same structure as blood sensor unit 44 unless described otherwise. Here, blood sensor 42 is attached on the upper face of attaching part 130*b* of blood sensor unit 130. The inner diameter of lower end 130*d* of holder 130*a* is smaller than the inner diameter of upper end 130*c*.

The diameter of opening part 130*e* of negative pressure chamber 60 formed on the lower side of attaching part 130*b* is preferably 2 to 20 mm, more preferably, 3 to 10 mm, and, even more preferably, 5 to 7 mm, so that a negative pressure is created on the skin to be punctured more efficiently. Further, by making the outer shape of lower end 130*d* smaller than the outer shape of upper end 130*c*, it is possible to stack a plurality of blood sensor units 130 vertically and accommodate blood sensor units 130 efficiently. Generally, blood sensor 42 needs to have a certain size, and so the outer shape of upper end 130*c* is difficult to be made smaller.

Further, locking convex part 130*g* latches blood sensor 42 and prevents blood sensor 42 from being removed from holder 130*a* wherein locking convex part 130*g* is provided inside holder 130*a* so as to project toward blood sensor 42.

Figure 25:
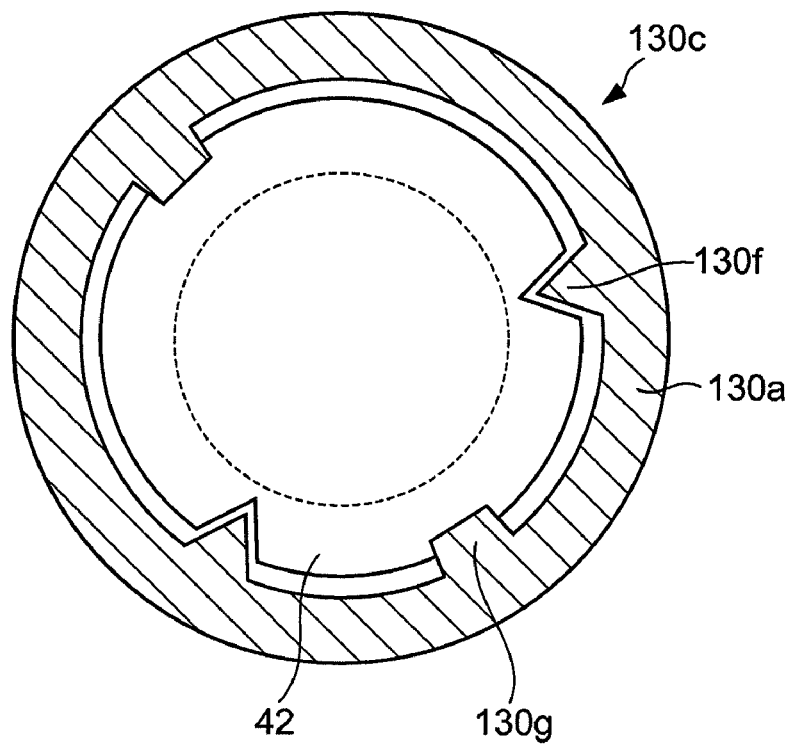
FIG. 25 is a plan view showing the blood sensor unit of FIG. 24.

FIG. 25 is a plan view of blood sensor unit 130. Two convex parts 130*f* that fit concave parts 46*c* and 47*c* (see FIG. 15) for aligning blood sensor 42 are formed in holder 130*a* of blood sensor unit 130 (at an angle of approximately 120 degrees). The alignment where blood sensor 42 is arranged in blood sensor unit 130 is determined by convex part 130*f* of holder 130*a* and aligning concave part 46*c* of blood sensor 42. Blood sensor unit 130 where blood sensor 42 is arranged adequately is attached to adapter 40 in a predetermined alignment by guide part 63 (see FIG. 17). In this way, signals of detection electrodes 54 to 57 of blood sensor 42 are transmitted to electrical circuit section 36. There may be one convex part 130*f*, but, in that case, attaching part 130*b* preferably has a structure that allows blood sensor 42 to be fit in.

The Focal Point of Laser Light

The blood test apparatus of the present invention uses laser light as a puncturing means, and, the laser emitting apparatus is accommodated in the apparatus body (see FIG. 2, for example). The emitted laser light is focused by a focus lens and emitted to skin. In the blood test apparatus of the present invention, laser light is preferably focused near the surface of the blood sensor. As described above, skin to be punctured is sucked in by the negative pressure means and is placed in close contact with the blood sensor, so that the laser light focused near the surface of the blood sensor can puncture the skin effectively.

Figure 26:
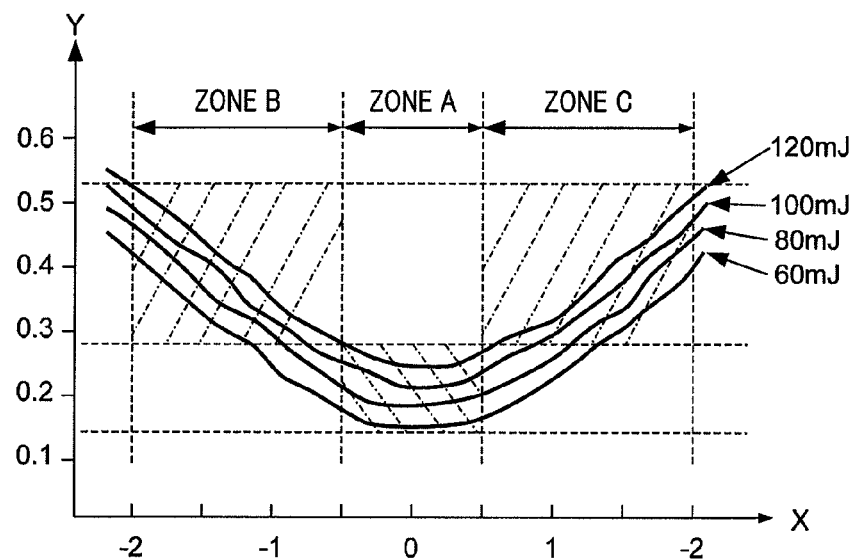
FIG. 26 is a graph showing the relationship between the distance from the focal point of a laser light to the puncturing target (X axis), and the burn pattern diameter (Y axis), in the blood test apparatus of the present invention.

The focal point of the laser light may be at the surface of the blood sensor or may be closer to the skin than the surface of the blood sensor or closer to the laser emitting apparatus than the surface of the blood sensor. FIG. 26 shows a result of examining using a laser alignment paper (ZAP-IT corporation: Z-48), the relationship between the "burn pattern diameter (mm)" (Y axis) and the "distance (mm) from the laser focus to the target to be punctured (the puncturing target, which in this case is the laser alignment paper)" (X axis). The "burn pattern diameter" is the diameter of the hole which is opened when laser light is emitted.

FIG. 26 is a graph showing the relationship between the distance (X axis) from the focal point of laser light to the puncturing target, and the burn pattern diameter (Y axis) in the blood test apparatus of the present invention. In the X axis in the graph shown in FIG. 26, "0" is the focal point of laser light. The negative ("−") domain indicates cases where the position of the puncturing target is set closer to laser emitting apparatus 33 than the focal point of laser light, and the positive ("+") domain indicates cases where the position of the puncturing target is set farther from laser emitting apparatus 33 than the focal point of laser light.

The laser output intensity includes four types of 60 mJ, 80 mJ, 100 mJ and 120 mJ. Although the burn pattern diameter becomes greater proportional to the output intensity, the relationship between the distance (X) from the puncturing target to the focal point and the burn pattern diameter (Y) is similar between all output intensities.

In zone A (when the focus is adjusted near the puncturing target), even when the position of the puncturing target shifts somewhat, the burn pattern diameter does not change significantly. Therefore, it is possible to puncture the skin reliably. On the other hand, in zone B or zone C, the burn pattern diameter changes significantly by the shift of the position of the puncturing target. In a case that the focus position of laser light shifts, the burn pattern diameter change in the same manner, because the focus position of laser light has a relative relationship with the position of the puncturing target. That is, when the position of the puncturing target is fixed, for example, in zone A (when the focus is adjusted near the puncturing target), even if the focal point of laser light shifts somewhat, the burn pattern diameter does not change significantly. Therefore, it is possible to puncture the skin reliably. On the other hand, in the case of zone B or zone C, when the focal point of laser light shifts, the burn pattern diameter changes significantly.

If the focal point of laser light shifts so as to increase the burn pattern diameter, the skin is not punctured, so that safety improves. For example, if the focal point of laser light is adjusted in zone B, unless the position of the puncturing target approaches the position from which the laser light is emitted, up to a predetermined position, the skin is not punctured. That is, unless enough skin is sucked in and lifted by a negative pressure, the skin is not punctured. Further, by adjusting the focal point of the laser light in zone C, when the position of the puncturing target comes closer to the position from which the laser light is emitted, than a predetermined position, the skin is not punctured. That is, when skin is sucked in and lifted more than necessary by a negative pressure, the skin is not punctured.

Further, when a film that is prone to melt is arranged in blood sensor 42, there is a case where the focal point is not preferably adjusted on blood sensor 42, because the film melts and energy of laser light is consumed. Therefore, there is a case where the focal point is preferably adjusted in zone B or zone C.

The Negative Pressure Chamber

The blood test apparatus of the present invention has a negative pressure means, and, the apparatus body accommodates a mechanical suction pump (see 34a in FIG. 2) or a manual suction pump (see 141 in FIG. 3) as one component of the negative pressure means. The negative pressure means creates a negative pressure in a negative pressure chamber and sucks in and lifts skin, which is the part to be punctured, thereby bringing the skin into close contact with the blood sensor.

As described above, negative pressure means 34 is configured with suction pump 34a, pump valve unit 34b and vent switch 34c (see FIG. 2). Negative pressure means 140 is configured with manual pump 141 and manual pump knob 142, in addition to pump valve unit 143 and vent switch 144 (see FIG. 3). In a broad sense, the term "negative pressure means" includes the negative pressure path in addition to the pump (a suction pump or a negative pressure pump) and the valve (a negative pressure valve or an open valve). Further, here, "driving the negative pressure means" means driving the pump and the valve, and "releasing the negative pressure" means opening the valve and introducing an outside atmospheric pressure (for example, atmospheric pressure).

Figure 27:
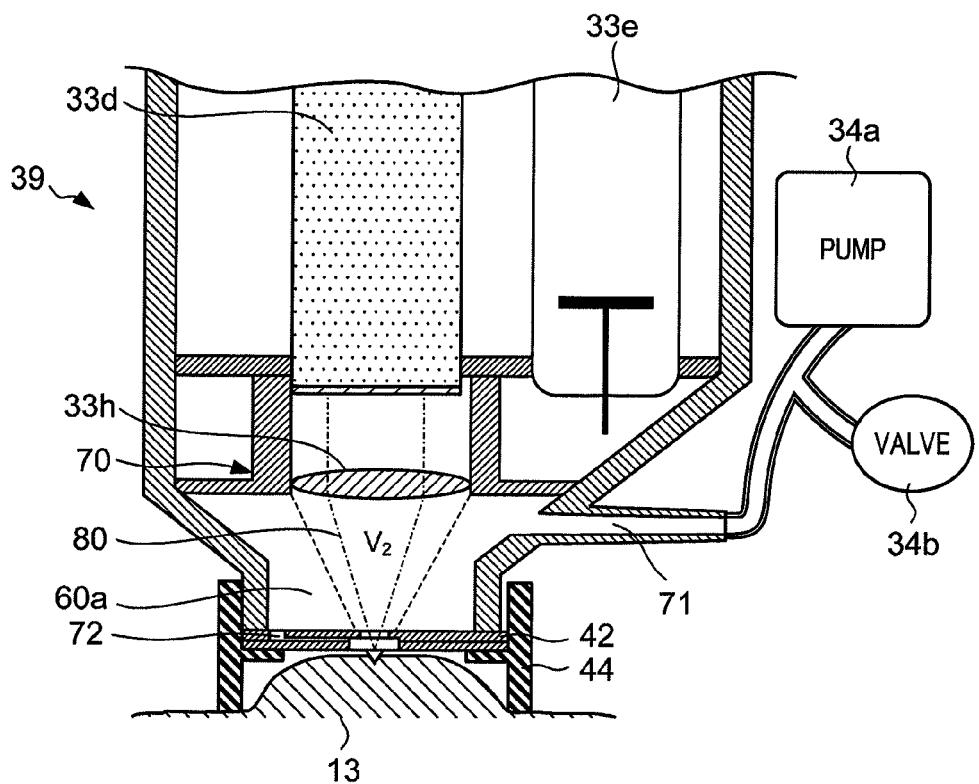
FIG. 27 is an enlarged view of the primary part showing an example of a negative pressure chamber and a negative pressure path in the blood test apparatus of the present invention.
Figure 28:
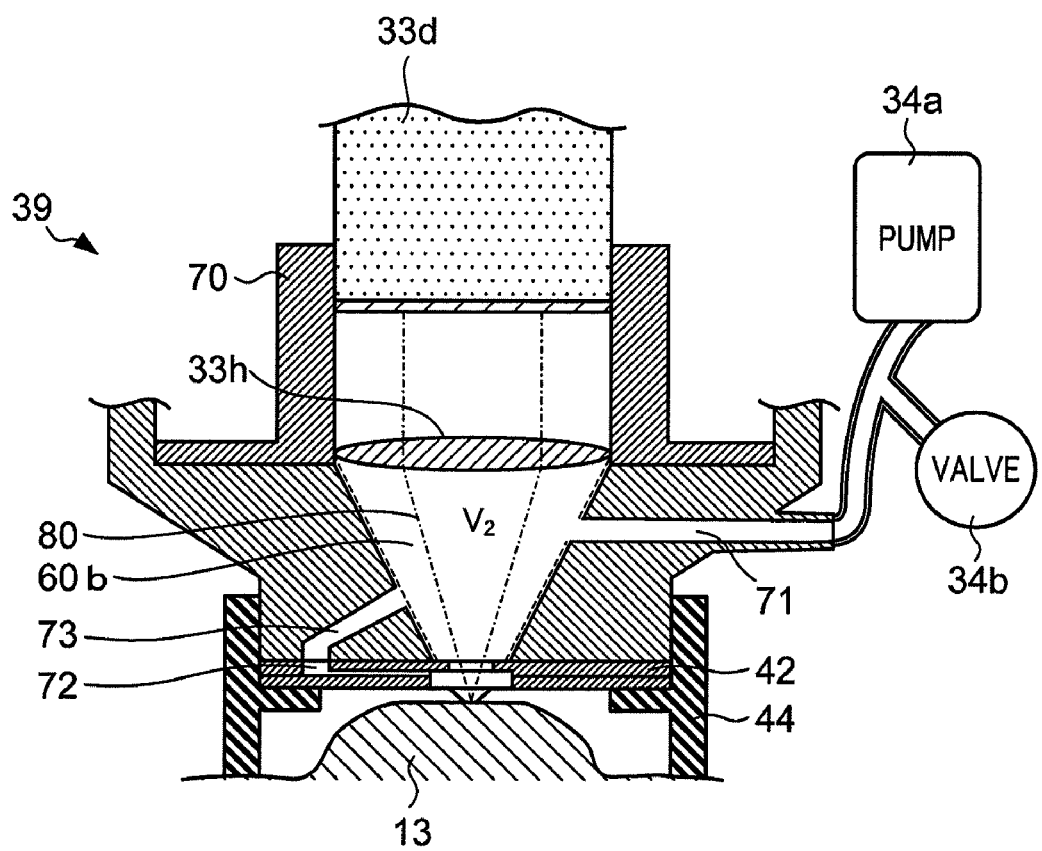
FIG. 28 is a cross-sectional enlarged view of the primary part showing another example of the negative pressure chamber and the negative pressure path in the blood test apparatus of the present invention.

FIG. 27 and FIG. 28 show a negative pressure chamber (suction chamber) and a negative pressure path. FIG. 27 shows a negative pressure path for the case where the negative pressure chamber is the largest, and FIG. 28 shows a negative pressure path for the case where the negative pressure chamber is the smallest. The negative pressure chamber of the blood test apparatus is explained referring to apparatus 31 in FIG. 2 as an example. Both suction chamber 60a shown in FIG. 27 and suction chamber 60b shown in FIG. 28 are internal space of apparatus body 39, and provided in space closer to blood sensor 42 than laser emitting hole 33c of laser emitting apparatus 33. Negative pressure chamber 60 widely refers to space where skin 13 comes into contact with blood sensor unit 44 and a negative pressure is created upon measurement, and includes internal space of blood sensor unit 44 in addition to suction chambers 60a and 60b in apparatus body 39. As shown in FIG. 27 and FIG. 28, negative pressure chamber 60 (particularly, suction chambers 60a and 60b) is, for example, vacuumed by pump 34a (that is, a negative pressure is created), and a negative pressure is released by valve 34b.

If negative pressure chamber 60 is small, the energy required to create a negative pressure is reduced and the time required for the blood test is also reduced. Therefore, negative pressure chamber 60 (particularly, suction chambers 60a and 60b) inside blood test apparatuses 31 and 31a of the present invention is preferably partitioned by a wall provided closer to blood sensor 42 than laser emitting hole 33c of laser emitting apparatus 33.

To be more specific, wall (partition or dividing wall for a negative pressure) 70 that partitions suction chambers 60a and 60b is preferably arranged in the same position as laser emitting hole 33c or in the same position as focus lens 33h (that is, the wall and focus lens 33h are integrated), or focus lens 33h itself may serve as a wall. Examples shown in FIG. 27 and FIG. 28 show the latter case. Further, to reduce the volume of negative pressure chamber 60, the shape of the suction chamber may be a conically-shaped (see suction chamber 60b in FIG. 28). Apparatus body 39 has negative pressure path 71 that communicates with suction chambers 60a and 60b, and this negative pressure path 71 is connected to the suction port of pump 34a. As described above, storing part 49, supply channel 50 and air hole 52 which also function as negative pressure path 72, are provided inside blood sensor 42. Suction chambers 60a and 60b also communicate with this negative pressure path 72 in blood sensor 42. Particularly, in a configuration example of FIG. 28, tiny negative pressure path 73 that connects suction chamber 60b and air hole 52 is further provided in apparatus body 39. Negative pressure paths 72 and 73 (except part of storing part 49) are microchannels, having approximately zero volume.

Figure 29:
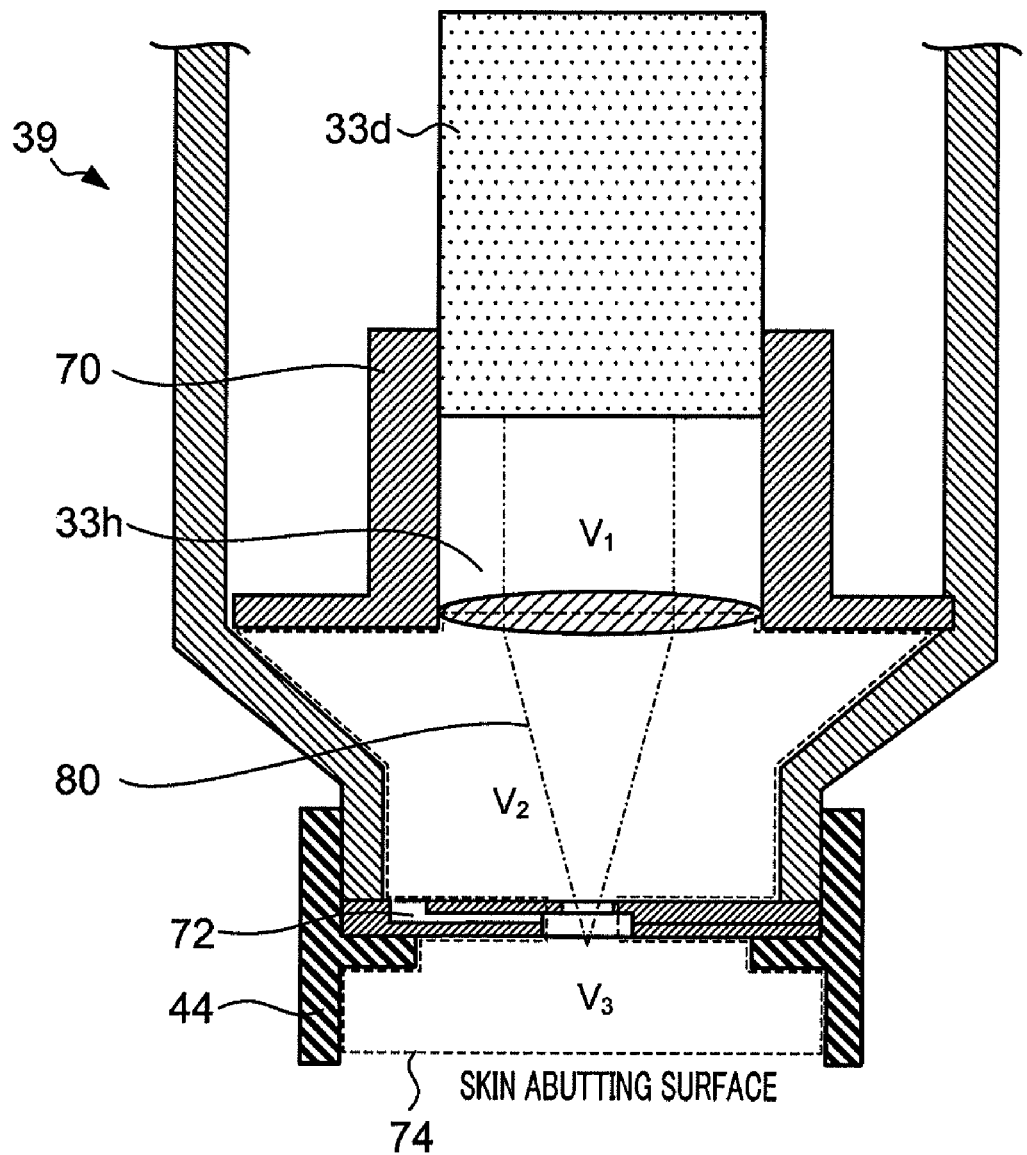
FIG. 29 illustrates the volume of the negative pressure chamber shown in FIG. 27.
Figure 30:
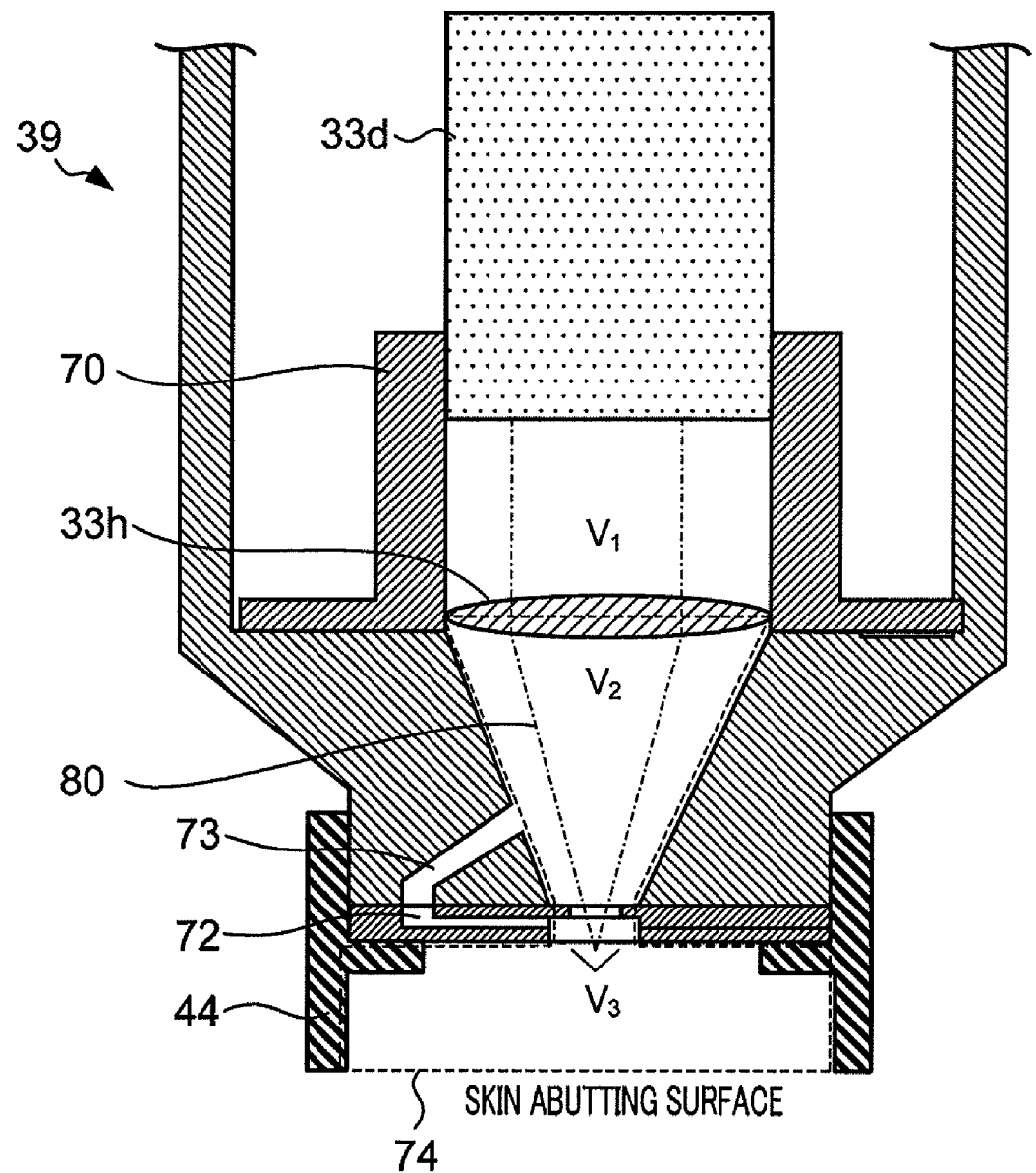
FIG. 30 illustrates the volume of the negative pressure chamber shown in FIG. 28.

As shown in FIG. 29 and FIG. 30, in blood test apparatuses 31 and 31a, there are at least three internal spaces $V_1$, $V_2$ and $V_3$ as the internal space including the path of laser light 80. Internal space $V_1$ is the space between the front surface of laser crystal (laser rod) 33d and focus lens 33h. Internal space $V_2$ is the space between focus lens 33h and blood sensor 42 (or holder 41) in blood sensor unit 44, and corresponds to suction chamber 60a or 60b in apparatus body 39 in the configuration examples in FIG. 27 or FIG. 28. Internal space $V_3$ is the space between blood sensor 42 (or holder 41) in blood sensor unit 44 and skin contacting surface 74 and mainly corresponds to the internal space of blood sensor unit 44. Negative pressure chamber 60 shown in FIG. 27 is configured with $V_2$ and $V_3$ and has a volume of approximately 9 cc when the volume of suction chamber 60a is made a maximum (see the area surrounded by a dotted line in FIG. 29). Further, negative pressure chamber 60 shown in FIG. 28 is also configured with $V_2$ and $V_3$ and has a volume of approximately 0.45 cc when the volume of suction chamber 60b is made a minimum (see the area surrounded by a dotted line in FIG. 30).

The Electrical Circuit

Figure 31:
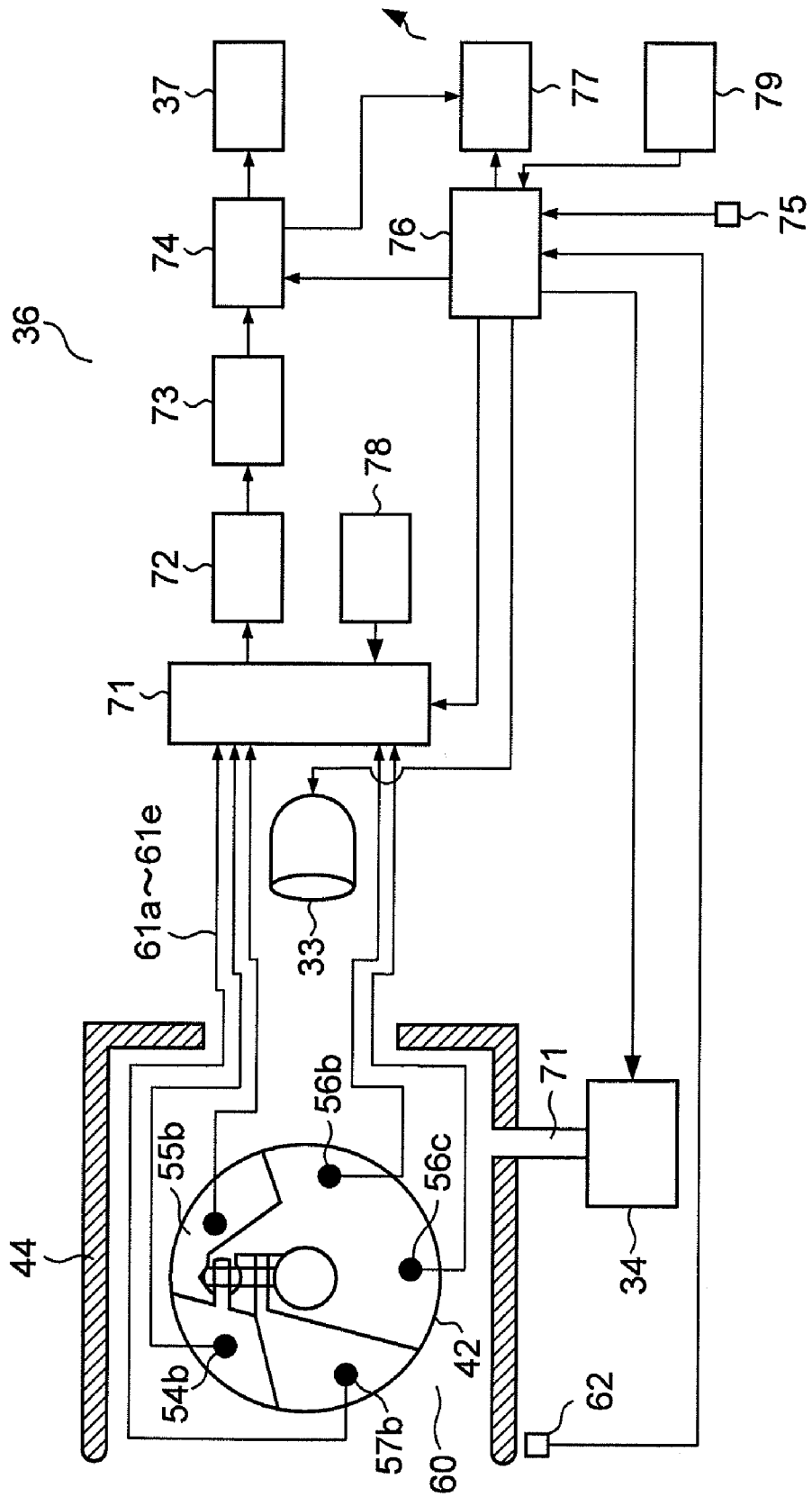
FIG. 31 is a block diagram showing an electrical circuit section in the blood test apparatus of the present invention.

FIG. 31 is a block diagram of electrical circuit section 36. In FIG. 31, 54b to 57b and 56c are contact parts provided in blood sensor 42. Contact parts 54b to 57b and 56c are connected to switch circuit 71 via connectors 61a to 61e. The output of switch circuit 71 is connected to the input of current/voltage converter 72. The output of current/voltage converter 72 is connected to the input of calculating section 74 via analogue/digital converter (hereinafter "A/D converter") 73. The output of calculating section 74 is connected to display section 37 formed with liquid crystal. Further, reference voltage supply 78 is connected to switch circuit 71. Reference voltage supply 78 may be a ground potential.

The output and input of controlling section 76 is connected to a control terminal of switch circuit 71, calculating section 74, puncture button 75, transmitting section 77, timer 79, laser emitting apparatus 33, negative pressure means 34 (particularly, suction pump 34a) and first skin contact sensor 62, and also connected to a warning means (not shown) and second skin contact sensor 110m (see FIG. 22). Further, the output of calculating section 74 is also connected to the input of transmitting section 77. The suction port of negative pressure means 34 (particularly, pump valve unit 34b) is led inside negative pressure chamber 60 and blood sensor unit 44 via negative pressure path 71.

The operation of electrical circuit section 36 will be described. Before a blood test, it is specified to which of connectors 61a to 61e, contact parts 54b to 57b and 56c of blood sensor 42 are each connected. First, by the command from controlling section 76, contact part 56c is specified among connectors 61a to 61e, wherein electrical resistance between contact part 56c and the neighboring terminals is zero, is specified. The connection electrode connected to specified contact part 56c is determined as reference electrode 56d. Using connector 61 connected to contact part 56c as a reference, connectors 61 connected to connection electrodes 56a, 57a, 54a and 55a, are specified in order. In this way, connectors 61 connected to connection electrodes 54a to 57a are specified.

Then, a blood test is conducted. Next, switch circuit 71 is switched, and detection electrode 54 as an active electrode for measuring the amount of blood component is connected to current/voltage converter 72 via connectors 61 determined as described above. Further, detection electrode 54 which serves as a sensing electrode for detecting the inflow of blood 16 is connected to reference voltage supply 78 via connectors 61 determined as described above. A certain voltage is applied between detection electrode 54 and detection electrode 55. When blood 16 flows into detecting section 51 in this state, a current flows between detection electrode 54 and detection electrode 55. This current is converted to a voltage by current/voltage converter 72, and the voltage value is converted to a digital value by A/D converter 73. The digital value is outputted to calculating section 74. Calculating section 74 detects a sufficient inflow of blood 16 based on the digital value.

When blood 16 is not detected at detecting section 51 after a predetermined time has passed or when the amount of blood 16 is not adequate, a warning means may be started for warning, and the treatment may be displayed on display section 37.

Next, glucose, which is a blood component, is measured. The glucose content is measured by, first, switching switch circuit 71 by the command from controlling section 76 and connecting detection electrode 54, which serves as the active electrode for measuring the glucose content, to current/voltage converter 72 via connectors 61. Further, detection electrode 56, which serves as the counter electrode for measuring the glucose content, is connected to reference voltage supply 78 via connectors 61.

For example, while the glucose in blood and the oxidation-reduction enzyme are reacted for a certain period, current/voltage converter 72 and reference voltage supply 78 are turned off. After a certain period (1 to 10 seconds) has passed, by the command from controlling section 76, a certain voltage (0.2 V to 0.5 V) is applied between detection electrode 54 and detection electrode 56. The current flowing between detection electrode 54 and detection electrode 56 is converted to a voltage by current/voltage converter 72. This voltage value is converted to a digital value by A/D converter 73. This digital value is outputted to calculating section 74. Calculating section 74 calculates the glucose content based on this digital value.

While the glucose content is measured, the Hct (hematocrit) level is measured. First, by the command from controlling section 76, switch circuit 71 is switched. Detection electrode 57, which serves as an active electrode for measuring the Hct level, is connected to current/voltage converter 72 via connectors 61. Further, detection electrode 54, which serves as a counter electrode for measuring the Hct level, is connected to reference voltage supply 78 via connectors 61.

Next, by the command from controlling section 76, a certain voltage (2V to 3V) is applied between detection electrode 57 and detection electrode 54. The current flowing between detection electrode 57 and detection electrode 54 is converted to a voltage by current/voltage converter 72. This voltage value is converted to a digital value by A/D converter 73. This digital value is outputted to calculating section 74. Calculating section 74 calculates the Hct level based on this digital value.

Using the calculated Hct level and the glucose content, and, with reference to a calibration curve or a calibration table, which was calculated in advance, the glucose content is corrected with the Hct level. The corrected result is displayed on display section 37.

Further, the corrected result may be transmitted from transmitting section 77 to an injection apparatus that injects insulin (an example of a curative drug). The result may be transmitted by radio, but is preferably transmitted via optical communication which does not interfere with medical equipment. If the injection apparatus can set the dose of insulin automatically based on the measured data transmitted to the injection apparatus, the patient does not have to set the dose of insulin to be administered in the injection apparatus, which alleviates the inconvenience of the setting. Further, the dose of insulin can be set in the injection apparatus without involving an artificial means, so that it is possible to prevent setting human errors.

Although the blood test apparatus of the present invention has been described using an example of measuring glucose, the blood test apparatus of the present invention is also applicable to measurement of the blood component (such as the lactate level acid and cholesterol) other than glucose.

Flow 1 of Measurement Steps

Figure 32:
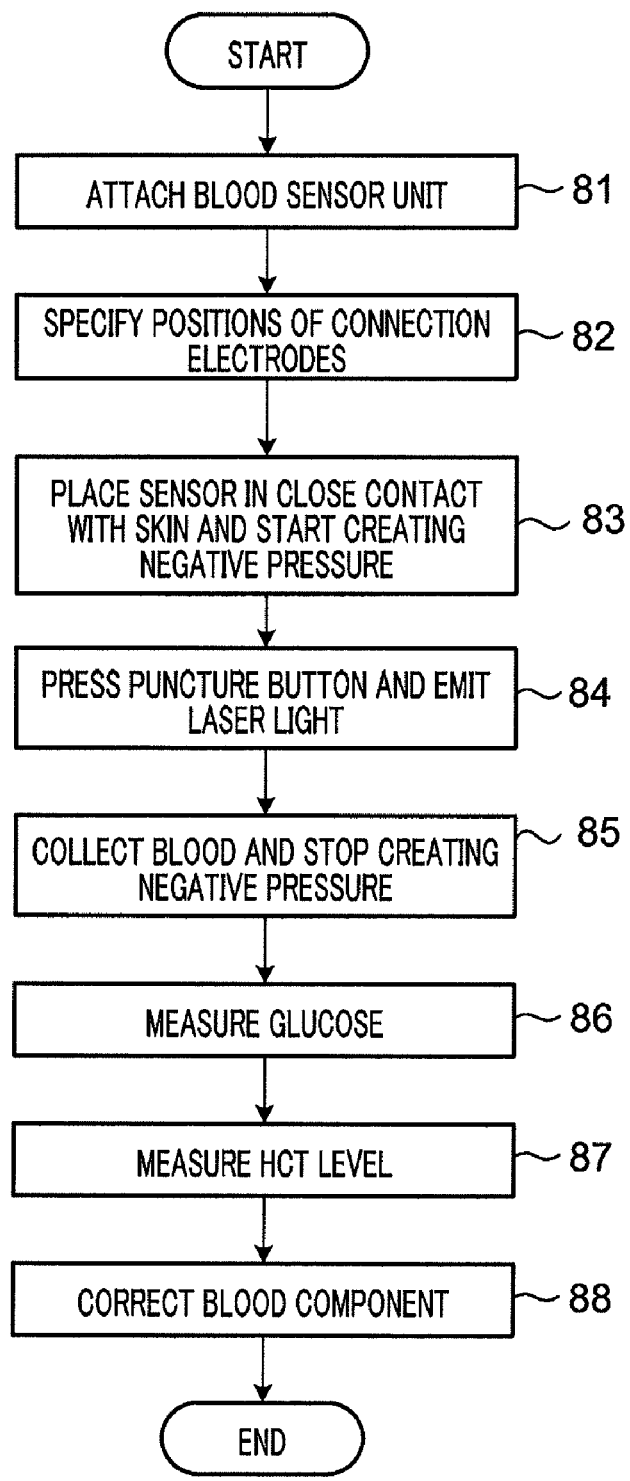
FIG. 32 is a flowchart showing an example of steps of test using the blood test apparatus of the present invention.
Figure 33A:
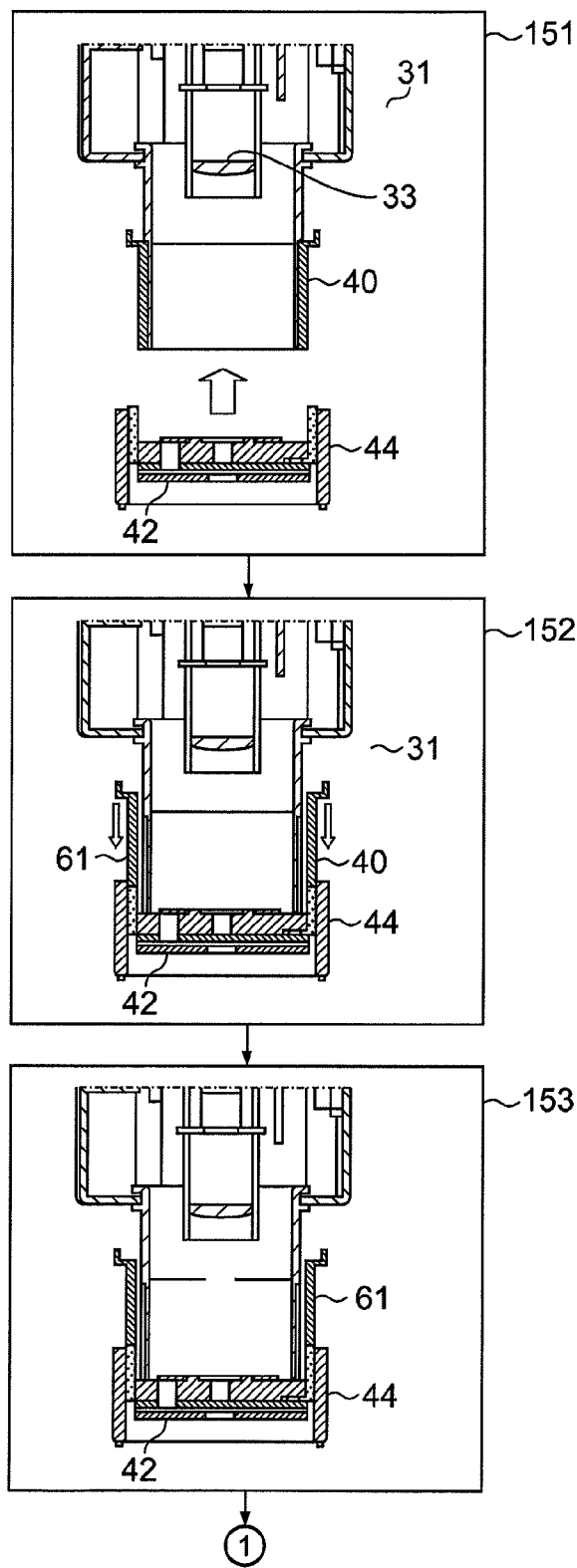
FIG. 33A is a cross-sectional view showing individual steps in an example of steps of test using the blood test apparatus of the present invention more specifically.
Figure 33B:
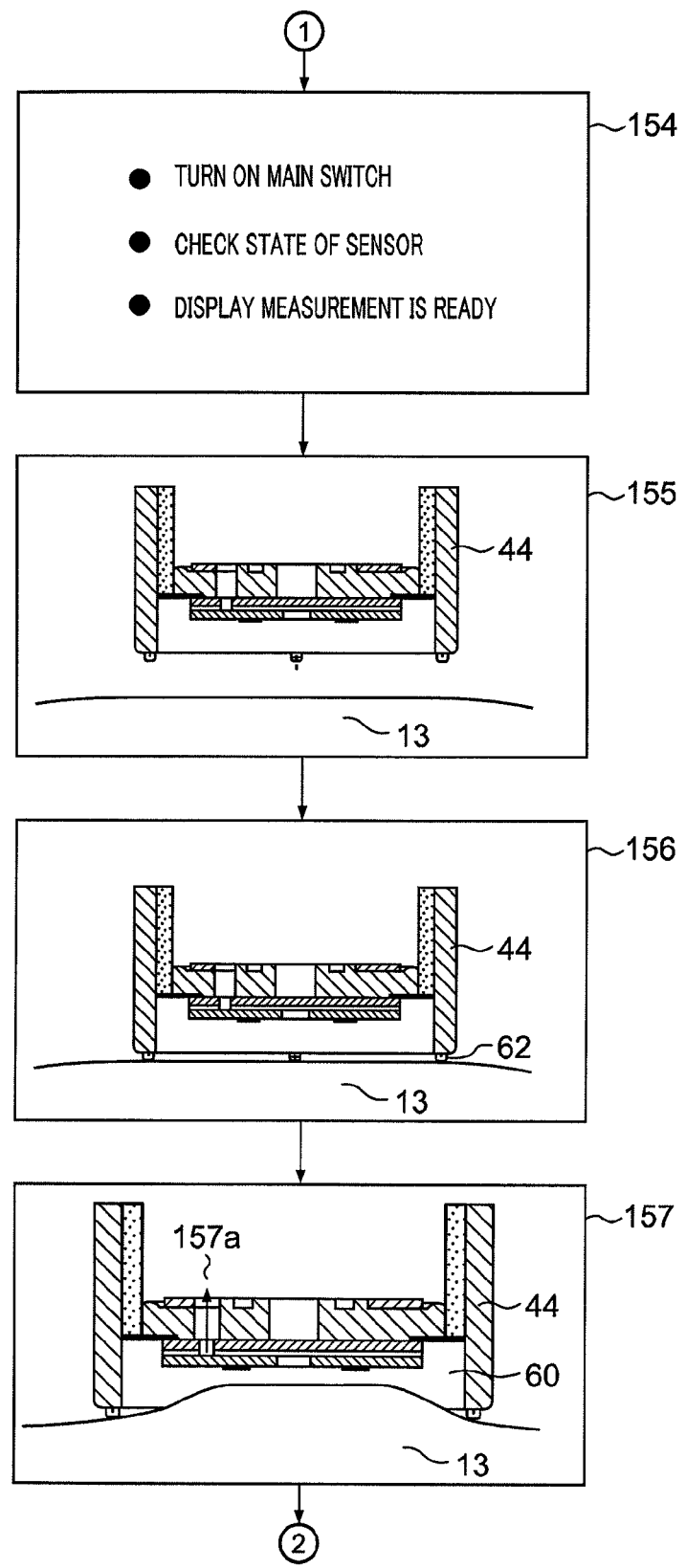
FIG. 33B is a cross-sectional view showing individual steps following FIG. 33A.
Figure 33C:
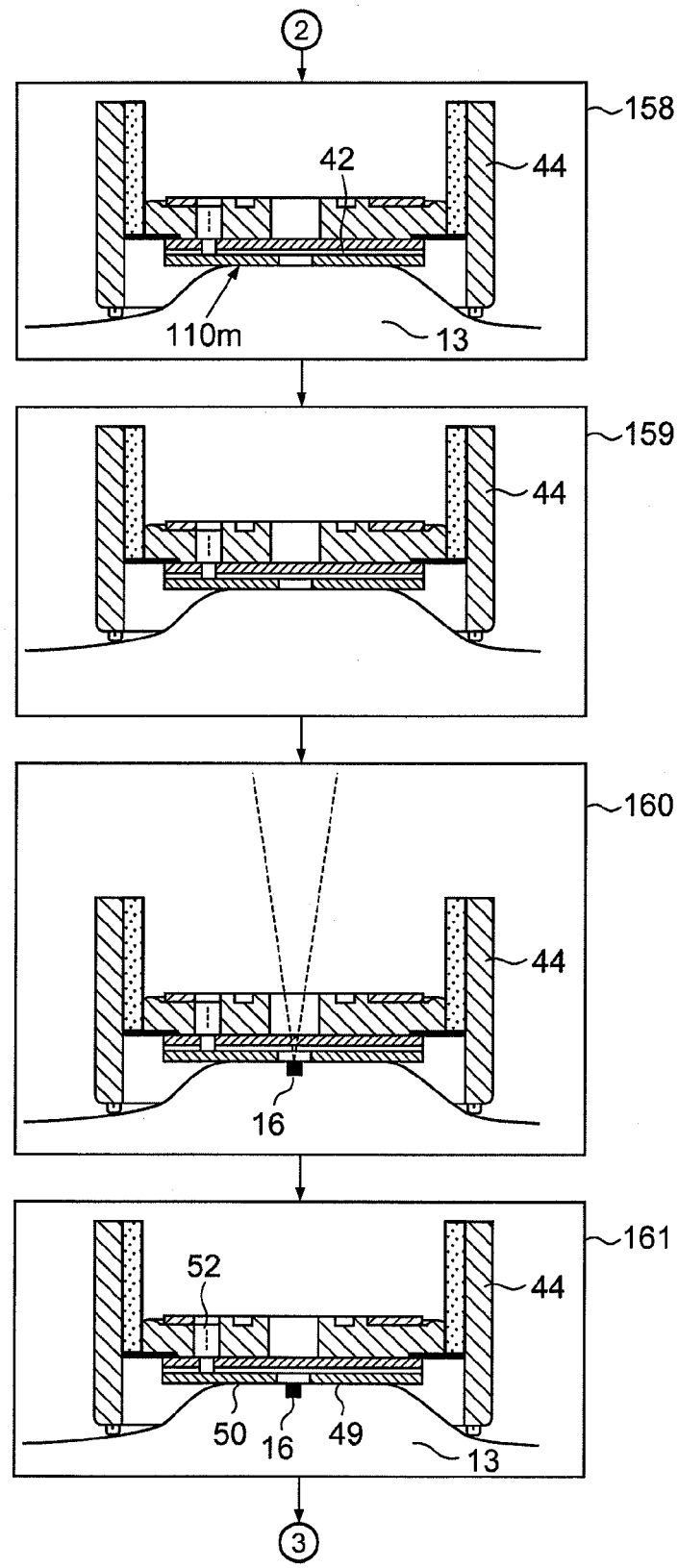
FIG. 33C is a cross-sectional view showing individual steps following FIG. 33B.
Figure 33D:
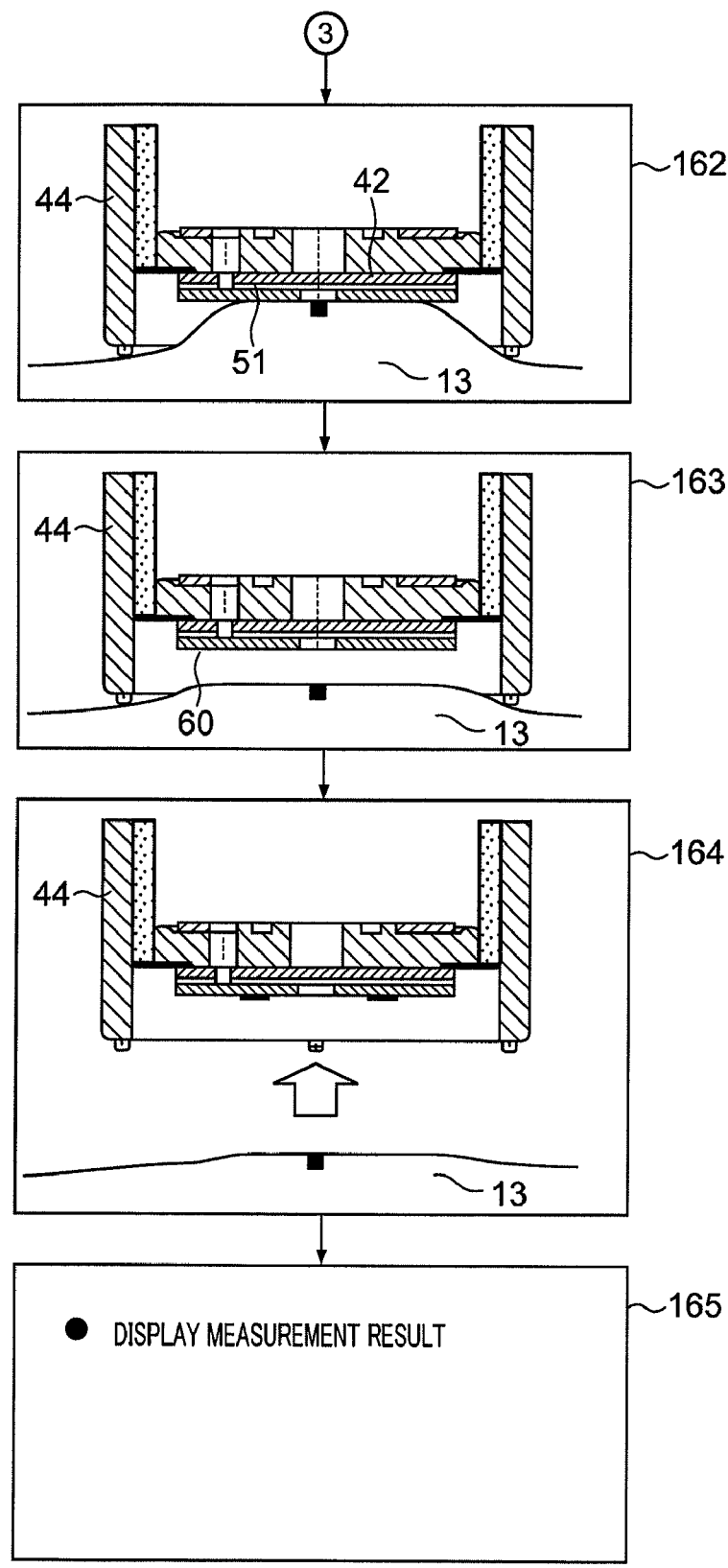
FIG. 33D is a cross-sectional view showing individual steps following FIG. 33C.

The flow of a blood test using blood test apparatus 31 shown in FIG. 2 will be described with reference to FIG. 32.

First, blood sensor unit 44 is attached to blood test apparatus 31 (step 81). In this step 81, blood sensor unit 44 is inserted into adapter 40. By this insertion, the tip of adapter 40 abuts on attaching part 41b of blood sensor unit 44. Blood sensor unit 44 is latched to adapter 40 by the elasticity of holder 41.

Next, connection electrodes 54a to 57a of blood sensor 42 are specified (step 82). Here, reference electrode 56d is specified from the resistance values between neighboring connectors 61a to 61e in electrical circuit section 36. From specified reference electrode 56d, connection electrodes 56a, 57a, 54a and 55a are specified clockwise. In this way, each of connection electrodes 54a to 57a of blood sensor 42 of blood sensor unit 44 inserted at an arbitrary angle is specified in step 82, and, as a result, each of detection electrodes 54 to 57 is specified.

Next, tip 41h of blood sensor unit 44 is pressed against skin 13 of the patient and is brought into close contact with skin 13 (step 83). When first skin contact sensor 62 detects a contact between skin 13 and tip 41h, suction pump 34a of negative pressure means 34 operates and starts creating a negative pressure. At this time, it is also possible to detect the load current applied to suction pump 34*a* with controlling section 76, and display on display section 37 whether the negative pressure is enough for puncturing. Instead of detecting a load current, it is possible to measure a predetermined time from the point when a negative pressure is created with timer 79 and display on display section 37 whether puncturing is possible. Further, if a second skin contact sensor (for example 110*m* in FIG. 22) is provided, it is possible to detect a lift of skin 13 by suction of a negative pressure. The detection may be displayed on display section 37.

In this way, if a negative pressure is created on skin 13 when skin 13 is punctured with laser light, skin 13 that is relaxed is brought in a state of tension, so that it is possible to collect blood 16 efficiently even if the prick by the puncturing is small. Therefore, the pain the patient feels is alleviated. Further, by lifting skin 13 to a predetermined position by a negative pressure to keep (control) the position of skin 13, it is possible to focus the emitted laser light correctly.

Next, puncture button 75 is pressed (step 84). A signal of puncture button 75 is recognized in electrical circuit section 36. When electrical circuit section 36 starts laser emitting apparatus 33, laser light is emitted toward skin 13. By setting the puncturing voltage of the laser light approximately 300 V, the pain the patient feels is alleviated.

Next, blood is collected (step 85). Blood 16 flowing out from skin 13 of the patient, punctured with the laser light, is stored in storing part 49 of blood sensor 42 (see FIG. 8, for example). Blood 16 stored in storing part 49 intrudes into supply channel 50 by capillary action and is led to detecting section 51. When blood 16 led to detecting section 51 reaches detection electrode 55 as the sensing electrode, detection electrode 55 determines that the amount of blood 16 required for measurement is obtained. At this time, negative pressure means 34 may be stopped, or negative pressure means 34 may be stopped after skin contact sensor 62 detects a non-contact of the skin.

On the other hand, when blood 16 is not detected at detecting section 51 after a predetermined time has passed or when the amount of blood 16 is not adequate (which is detected using the resistance between detection electrode 54 and detection electrode 55), a warning means may be started for warning, and the appropriate measures may be displayed on display section 37.

Next, glucose is measured (step 86). After glucose in blood and glucose oxidation-reduction enzyme are reacted for a certain period, glucose may be measured by applying a voltage between detection electrode 54 as the active electrode and detection electrode 56 as the counter electrode.

Further, the Hct level is measured (step 87). When a voltage is applied between detection electrode 57 as the active electrode and detection electrode 54 as the counter electrode, a current that depends on the Hct level is measured. The Hct level is measured based on this current.

Finally, the blood components are corrected (step 88). That is, the glucose content calculated in step 86 is corrected with the Hct level measured in step 87. The corrected result is displayed on display section 37. When measurement of the blood sugar level is finished through the above-described steps, blood sensor unit 44 after use is discarded.

Flow 2 of Measurement Steps

FIG. 33 schematically illustrates a flowchart of measuring steps in more detail. In FIG. 33, step 151 shows a state before blood sensor unit 44 is attached to adapter 40 of blood test apparatus 31. Step 152 shows a state where blood sensor unit 44 is inserted into adapter 40 along guide part 63 (see FIG. 7).

Step 153 shows a state where connector 61 is pressed down and contacts with contact parts 54*b* to 57*b* and 56*c* of sensor 42.

Next, in step 154, a main switch of blood test apparatus 31 is turned on. Electrical circuit section 36 detects reference electrode 56*d* automatically and specifies each of detection electrodes 54 to 57. Display section 37 then displays that preparation for measurement is completed.

In step 155, the end part of blood sensor unit 44 of blood test apparatus 31 is abutted on skin 13. In FIG. 33 after step 155, apparatus body 39 of blood test apparatus 31 is omitted, and only blood sensor unit 44 is shown. In step 156, blood test apparatus 31 is abutted on skin 13 of the patient. First skin contact sensor 62 detects skin 13 when blood test apparatus 31 comes into contact with skin 13.

When first skin contact sensor 62 detects skin 13, step 157 is started. Negative pressure means 34 starts operating and vacuums negative pressure chamber 60 as shown by arrow 157*a*. As a result of the suction, skin 13 is lifted. In the case of manual negative pressure means 140 (see FIG. 3), display section 37 displays start of manual operation, and the patient starts operating manual pump knob 142.

When a negative pressure is created, skin 13 is further lifted as shown in step 158 and touches second skin contact sensor (skin contact electrode) 110*m*. Second skin contact sensor 110*m* may be formed on the reverse side of blood sensor 42 attached on the lower face of blood sensor unit 44 (see FIG. 22) or formed on the lower face of attaching part 120*b* when blood sensor 42 is attached on the upper face of blood sensor unit 44 (see FIG. 23). Second skin contact sensor 110*m* only has to detect a contact between skin 13 and blood sensor 42, and, for example, an optical sensor, a mechanical switch or an electrical resistance detection element may be used instead of an electrode.

In step 159, suctioning skin 13 in negative pressure chamber 60 is stopped. When second skin contact sensor 110*m* is not provided, the suction may be stopped after a predetermined time has passed since negative pressure means 34 started operating. The time passed may be measured with timer 79 of electrical circuit section 36.

Next, in step 160, skin 13 is irradiated with laser light and punctured. By this puncturing, blood 16 flows out from skin 13. Skin 13 may be punctured automatically when second skin contact sensor 110*m* detects skin 13. Alternatively, it is also possible to allow the patient to press puncture button 75 (see FIG. 29) according to display on display section 37 that blood sensor unit 44 abuts on skin 13. When the patient presses puncture button 75, the patient can get ready for puncturing.

As shown in step 161, blood 16 flowing out from skin 13 fills storing part 49 and flows into supply channel 50. Blood 16 flows into supply channel 50 by capillary action in supply channel 50 and the suction through air hole 52 by negative pressure means 34. As shown in step 162, blood 16 is led to detecting section 51 of blood sensor 42. When the inflow of blood 16 into detecting section 51 is detected, the operation of negative pressure means 34 is stopped (step 163). When blood 16 reaches detection electrode 55 (see FIG. 12) of sensor 42, the inflow of blood 16 is detected. Then, vent switch 34*c* is operated to make the pressure in negative pressure chamber 60 equal to the outside atmospheric pressure.

Next, as shown in step 164, blood test apparatus 31 is released from skin 13. When measurement is finished, display section 37 displays that the measurement is finished. Then, in step 165, display section 37 displays the result of measuring collected blood 16.

Flow 3 of Measurement Steps (Including Authentication Steps)

The flow of a blood test using the blood test apparatus of the present invention may include the steps of authenticating the user (i.e., the patient), so that a party other than the authorized party is not allowed to use in view of safety, given that the blood test apparatus is laser equipment.

Figure 34:
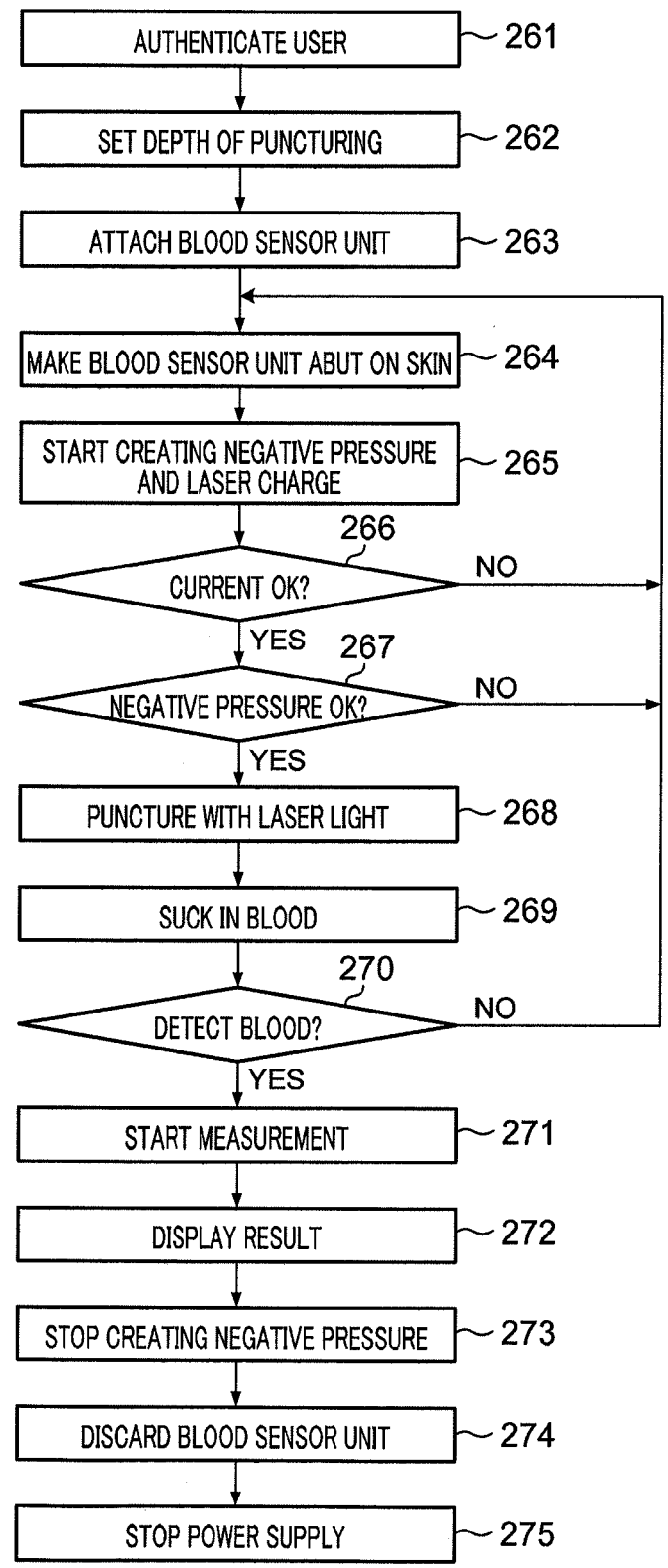
FIG. 34 is a flowchart showing another example of steps of test using the blood test apparatus of the present invention.

FIG. 34 shows a flow of a test including authentication step 261. Whether the patient is a predetermined authorized party may be authenticated using fingerprints, voice prints, iris and vein patterns, for example.

When the patient is authorized to use the apparatus, the flow proceeds to step 262. The patient sets the depth of puncturing (i.e., laser power) by operating dials. Then, in step 263, blood sensor unit 44 including blood sensor 42 is attached to adapter 40 of blood test apparatus 31. Apparatus body 39 automatically starts upon attachment of blood sensor unit 44 and enters a measurement standby state. It is also possible to perform step 263 of attaching blood sensor unit 44 before step 261. Although the measurement operation cannot be performed unless blood sensor unit 44 is attached, it is possible to display the measurement result.

Next, in step 264, first skin contact sensor 62 (see FIG. 16, for example) detects whether blood sensor unit 44 comes into contact with skin 13. Instead of using first skin contact sensor 62, the presence or absence of a blood vessel, the body temperature, the electrical resistance of the skin, or pulse, may be detected. In any case, in view of safety, the operation of step 265 and after step 265 is performed when a state where the contact between blood sensor unit 44 and skin 13 is detected. The apparatus waits in step 264 until the contact between blood sensor unit 44 and skin 13 can be detected.

When first skin contact sensor 62 detects the skin, the operation of negative pressure means 34 is started in step 265. Further, laser emitting apparatus 33 starts being charged with a drive voltage at the same time. In step 266, the value of the current flowing into negative pressure means 34 is monitored for 1 to 5 seconds. When the current value is not normal, display section 37 displays that the current value is not normal, and the flow returns to the step before step 264.

When the current value is normal, step 267 is started, and whether the negative pressure is adequate is determined. Whether the negative pressure is adequate is determined by comparing the current flowing into negative pressure means 34 with a predetermined threshold. When the negative pressure reaches a certain level, step 268 is started, and laser light emission is allowed. When the negative pressure does not exceed the threshold, assuming an air leakage (i.e., poor contact between blood sensor unit 44 and skin 13), suction by negative pressure means 34 is stopped and a retry is commanded, and then the flow returns to the step before step 264.

Further, by arranging second skin contact sensor 110m (see FIG. 22), it is possible to detect the lift of skin 13 sucked in by a negative pressure. When skin 13 is lifted adequately and is in close contact with blood sensor 42, laser light emission is allowed.

In step 268, laser light is emitted and punctures skin 13. In step 269, blood 16 flowing out from skin 13 by puncturing is guided into blood sensor 42. At this time, negative pressure means 34 continues to be driven.

Next, in step 270, it is checked whether blood 16 is guided into detecting section 51 (see FIG. 8) of blood sensor 42. Within a certain time (for example, 2 to 10 seconds) after puncturing, it is detected whether blood 16 reaches detection electrode 55. When blood 16 is not detected within a certain time, the flow returns to the step before step 264, and the skin is punctured again. Therefore, blood sensor 42 once attached is not wasted without being used. In addition, it is possible to quickly puncture the skin again.

When blood 16 is detected, step 271 is started, and the blood sugar level starts being measured. Further, in step 271, the negative pressure starts being released to the atmosphere by controlling pump valve unit 34b (see FIG. 2). At this time, negative pressure means 34 still operates, so that the patient figures out that measurement is still in progress from sound and vibration produced while negative pressure means 34 is driven, and the patient does not remove blood test apparatus 31 from skin 13. By this means, blood test apparatus 31 during measurement of the blood components is prevented from vibration and shock, and stable measurement is realized. Further, this prevents the patient from releasing the apparatus from skin 13 immediately after the negative pressure is released, and prevents blood 16 from splashing and contaminating the surrounding.

When the measurement is finished in step 271, step 272 is started, and display section 37 displays the measurement result. In step 273, negative pressure means 34 (particularly, suction pump 34a and pump valve unit 34b) (see FIG. 2) stops being driven. Afterward, the patient removes blood test apparatus 31 from skin 13.

Next, in step 274, the patient removes blood sensor unit 44 from apparatus body 39 of blood test apparatus 31 and discards blood sensor unit 44. In step 275, removal of blood sensor unit 44 is detected, and apparatus body 39 automatically turns off.

As described above, in measurement of the blood sugar level using blood test apparatus 31, laser emitting apparatus 33 is driven under the conditions (conjunctive condition) that blood test apparatus 31 contacts with skin 13, and so laser light is not emitted for purposes other than puncturing skin 13, so that it is secure. Further, prior to use of blood test apparatus 31, the user is authenticated in step 261. It is therefore also possible to allow only the authorized party to operate the apparatus and prevent the unauthorized user to operate the apparatus, so that the apparatus is secure.

Blood test apparatus 31 automatically turns on and off, so that it is possible to make the operation simple and reduce consumption of battery 35.

Control of a Negative Pressure in Laser Emission

Figure 35:
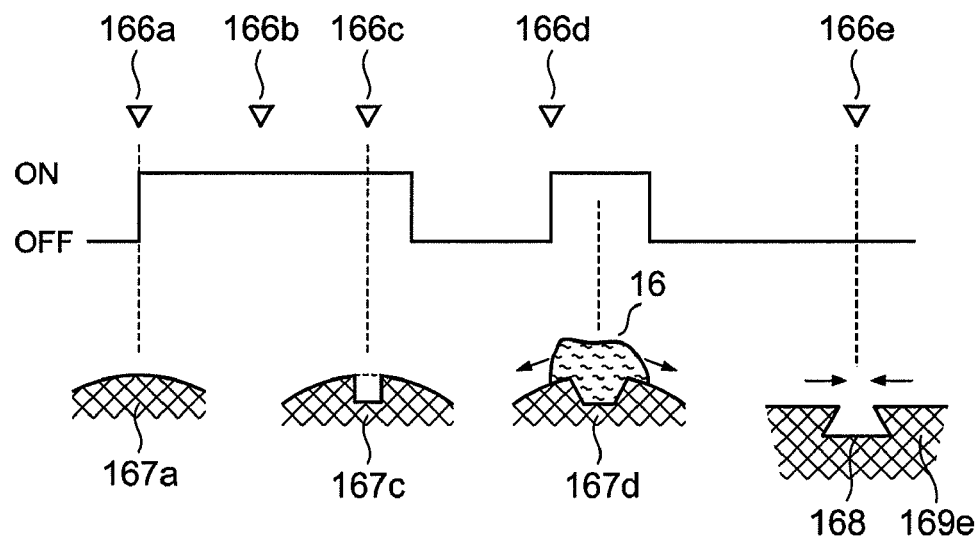
FIG. 35 illustrates an example of negative pressure control in the blood test apparatus of the present invention.
Figure 36:
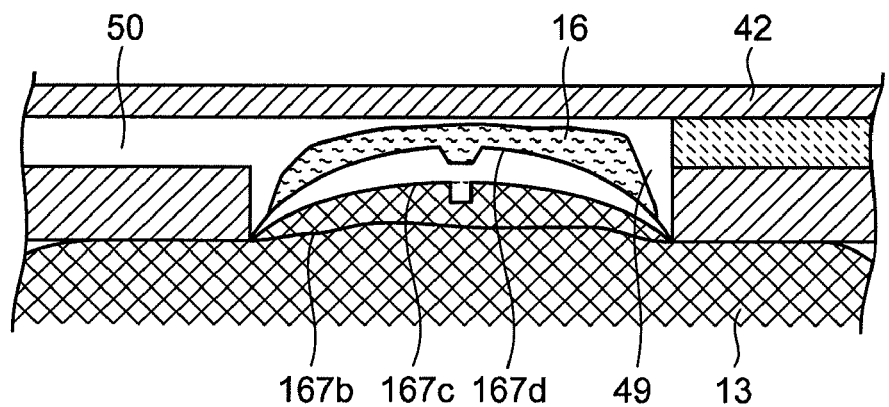
FIG. 36 schematically shows how skin is lifted by the negative pressure control illustrated in FIG. 35.

Blood test apparatus 31 of the present invention may intermissively create a negative pressure more than once after puncturing. The timing of creating a negative pressure and its effect will be described with reference to FIG. 35 and FIG. 36. When first skin contact sensor 62 detects skin 13, negative pressure means 34 starts being driven at time 166a (step 156 in FIG. 33). A negative pressure is created in negative pressure chamber 60, and skin 13 is tensed and lifted as shown in state 167a (step 157 in FIG. 33). Skin 13 is lifted and comes into contact with second skin contact sensor 110m at time 166b (step 158 in FIG. 33). At time 166b, skin 13 is as shown in state 167b in FIG. 36. Here, the negative pressure supplied to negative pressure chamber 60 is stopped (step 159 in FIG. 33). Then, at time 166c, skin 13 is punctured (step 160 in FIG. 33). Skin 13 becomes as shown in state 167c, and blood 16 leaks.

Then, after the negative pressure supply is once stopped, a negative pressure is created again at time 166d. By a negative pressure, the opening part of skin 13 widens as shown in state 167d, so that blood 16 flows out more easily (step 161 in FIG. 33). Therefore, one of the reasons for intermissively creating negative pressure is to widen the hole punctured in skin 13 and collect blood 16 more easily. Another reason is to prevent blood 16 from gushing out and being oversampled when suction is continuously performed with a strong negative pressure. Therefore, negative pressure means 34 is operated intermissively so that blood 16 does not overflow. In this way, power is saved by weakening sucking force, and an adequate amount of blood 16 is collected. When an adequate amount of blood 16 is obtained and accurate measurement is finished, blood test apparatus 31 is removed from skin 13 (step 164 in FIG. 33). At time 166e when the measurement is finished, as shown in state 169e, wound 168 widened by a negative pressure, of skin 13, is sealed again. Therefore, the wound heals faster.

There may be a case for some patients, little blood 16 flows out from skin 13 even if skin 13 is punctured with laser light. In such a case, it is also possible to make blood 16 flow out easily by increasing the negative pressure after puncturing compared to the negative pressure before puncturing. Since the maximum pressure (negative pressure) is fixed, a negative pressure is controlled by controlling the period valve 34b is closed. Further, it is also possible to configure so as to create a negative pressure continuously, instead of creating a negative pressure intermissively.

Figure 37:
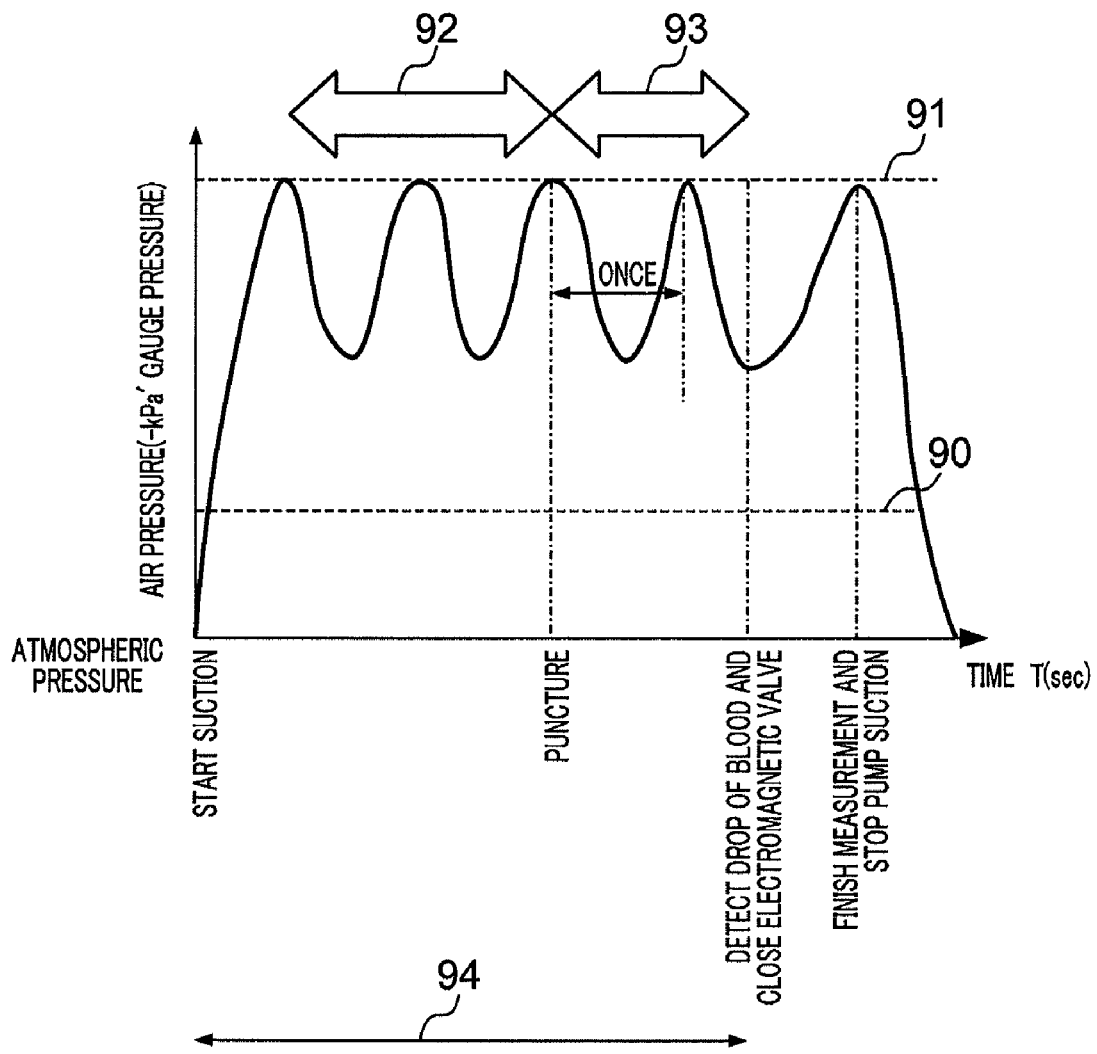
FIG. 37 illustrates another example of the negative pressure control in the blood test apparatus of the present invention.

Further, blood test apparatus 31 of the present invention may perform a "rubbing operation" before and after puncturing. The rubbing operation will be described with reference to FIG. 37. The rubbing operation is performed, for example, by driving pump 34a (for example, an electric suction pump) at a constant voltage and opening and closing valve 34b (for example, an electromagnetic valve) at a predetermined timing. In the operation example shown in FIG. 37, during the period after first skin contact sensor 62 detects skin 13 and negative pressure means 34 starts being driven (starts suction) until the skin is punctured with laser light, rubbing is performed as preparation before puncturing. After the skin is punctured with laser light, during the period after guiding of blood 16 into detecting section 51 of blood sensor 42 is detected (a drop of blood is detected) until electromagnetic valve 34b is closed, rubbing is performed at least once. In FIG. 37, air pressure level 90 is a negative pressure level (for example, −10 kPa) at which suction is hardly felt by patient, and level 91 is the maximum pressure (negative pressure) (for example, −70 kPa) when pump 34a is driven at a constant voltage. The opening and closing operations of valve (electromagnetic valve) 34b that results in rubbing operation, is performed at a timing at which the air pressure in negative pressure chamber 60 changes between level 90 and level 91 and its change period is longer (for example, 0.1 second or longer) than the minimum period skin 13 reacts to the change of the negative pressure. Such opening and closing operations of valve (electromagnetic valve) 34b are performed from when suction is started until when a drop of blood is detected and the electromagnetic valve is closed. As described above, the electromagnetic valve is closed after a drop of blood is detected, so that the punctured hole in skin 13 is widened and blood 16 is collected more easily. When blood 16 is collected and measurement is finished, negative pressure means 34 stops being driven (i.e., suction by a pump is stopped and the valve is released).

This rubbing operation improves blood circulation and makes blood 16 flow out more easily. By rubbing skin 13, the part to be punctured is heated (which improves blood circulation), so that it is possible to increase the amount of blood collected compared to a case where skin 13 is not rubbed. Further, the rubbing operation alleviates the pain upon puncturing.

The Laser Perforation Apparatus

Figure 38:
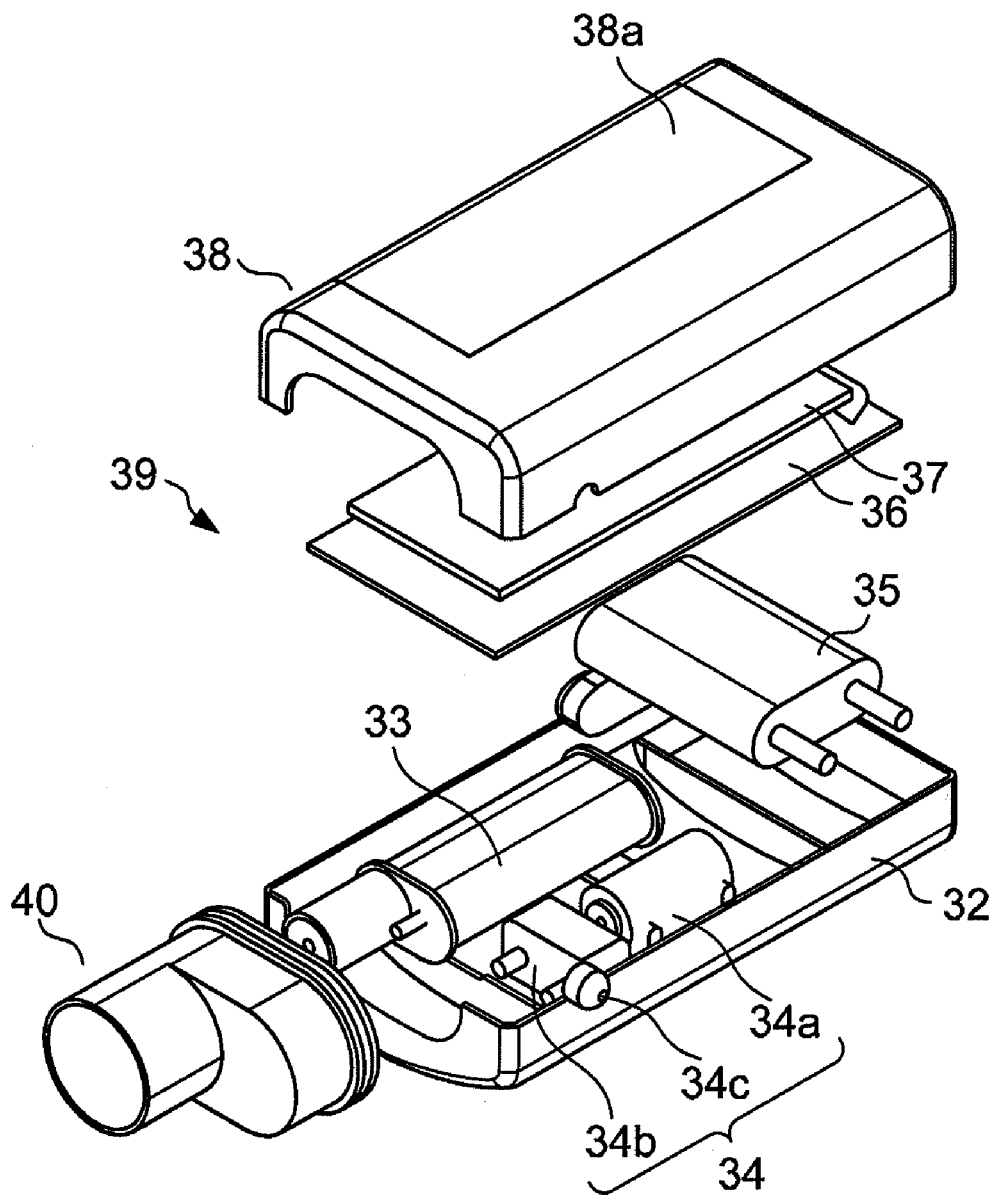
FIG. 38 is an exploded assembly perspective view showing an example of the laser perforation apparatus included in the blood test apparatus of the present invention.

Blood test apparatuses 31 and 31a of the present invention include a laser perforation apparatus shown in FIG. 38. This laser perforation apparatus has a same structure as blood test apparatuses 31 and 31a without blood sensor unit 44 and members relating to blood sensor unit 44 (for example, connectors connected with blood sensor 42). This laser perforation apparatus has a function of controlling the laser output of laser emitting apparatus 33 so as to puncture the same position to be punctured in a divided manner in one puncturing operation. Here, the "puncturing in a divided manner" refers to dividing one puncturing operation in space or in time. To be more specific, the former refers to a case where the puncturing operation is performed by dividing a laser light into a plurality of optical paths (branch control of the laser output), and the latter refers to a case where the puncturing operation is performed by emitting a laser light at several separate times (pulse control of the laser output).

Branch of Laser Light in Laser Emission

Figure 39:
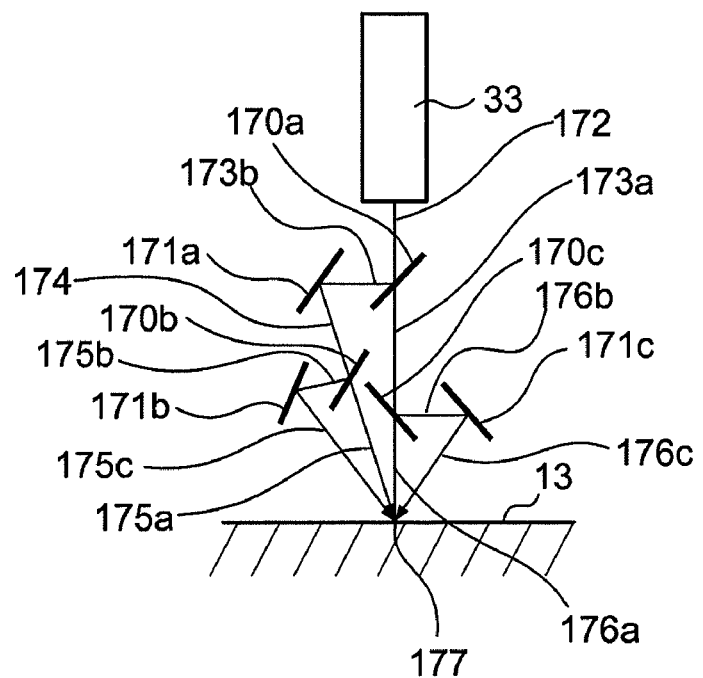
FIG. 39 shows an example of laser branch control in the blood test apparatus of the present invention.

Blood test apparatuses 31 and 31a of the present invention may puncture skin 13 by dividing one laser light emitted from laser emitting apparatus 33 into a plurality of laser lights. In FIG. 39, the reference numeral "33" is the laser emitting apparatus, and "13" is the skin of the patient. Further, reference numerals "170a," "170b" and "170c" are splitters that distribute incident light uniformly by allowing half of the incident light to pass and reflecting the other half of the incident light. These splitters 170a, 170b and 170c are formed with half mirrors.

Reference numerals "171a," "171b" and "171c" are total reflection mirrors that reflect all the incident light. These total reflection mirrors (hereinafter simply "mirrors") 171a, 171b and 171c are paired with splitters 170a, 170b ad 170c, respectively. In FIG. 39, these splitters 170a, 170b and 170c and mirrors 171a, 171b and 171c are set at predetermined angles with respect to an incident light so that the same irradiated position 177 is punctured.

Laser light 172 emitted from laser emitting apparatus 33 is branched into laser light 173a and 173b by splitter 170a. Branched laser light 173b enters mirror 171a, and laser light 173b is totally reflected by this mirror 171a and becomes laser light 174. This laser light 174 is branched into laser light 175a and laser light 175b by splitter 170b. Branched laser light 175a directly punctures irradiated position 177 in skin 13. Further, laser light 175b branched at splitter 170b is totally reflected by mirror 171b, becomes laser light 175c and punctures irradiated position 177 in skin 13.

On the other hand, laser light 173a which passes through splitter 170a is branched into laser light 176a and laser light 176b by splitter 170c. Branched laser light 176a directly punctures irradiated position 177 in skin 13. Further, laser light 176b branched by splitter 170c is totally reflected by mirror 171c, becomes laser light 176c and punctures irradiated position 177 in skin 13.

In this way, one laser light 172 is branched into a plurality of optical paths and punctures irradiated position 177 in skin 13, and the skin is punctured with laser light with a small output, so that it is possible to alleviate the pain. Therefore, it is possible to focus laser light on blood capillaries inside skin 13 and perform puncturing.

Figure 40:
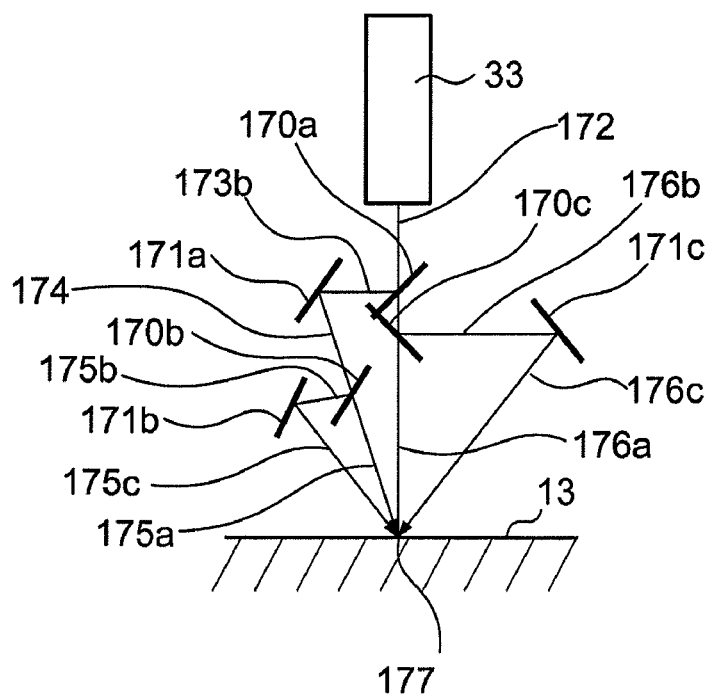
FIG. 40 illustrates the laser branch control of FIG. 39.

Further, as shown in FIG. 40, if mirror 171c is arranged farther from laser light 176a than the position shown in FIG. 39, it takes a longer time for laser light 176b branched by splitter 170c to reach irradiated position 177 in skin 13. Laser light 176b is totally reflected by mirror 171c and becomes laser light. In this way, by arranging mirrors at appropriate positions, it is possible to control the laser output so that the same position can be irradiated with a plurality of branched laser lights in order.

Figure 41:
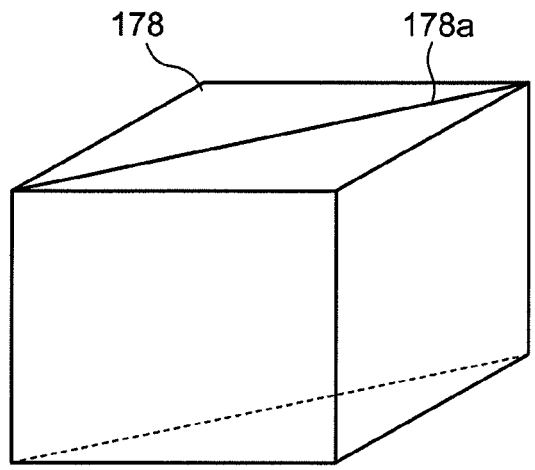
FIG. 41 is a perspective view of a cubic optical device that can be used in the laser branch control of FIG. 39.

Cubic optical device 178 that divides a rectangular parallelepiped with diagonal line 178a as shown in FIG. 41 is preferably used as splitters 170a, 170b and 170c and mirrors 171a, 171b and 171c. Cubic splitters 170a, 170b and 170c are formed by stacking mirrors of different refractive indexes on the matching surfaces, and cubic mirrors 171a, 171b and 171c are formed by stacking surfaces that totally reflect light and surfaces that totally transmit light. In this way, optical device 178 formed in a cubic shape does not cause a shift of the transmitting optical path and ghost, and can maintain high accuracy against changes such as division and refraction of the optical path. Further, one cubic optical device can constitute all or each of splitters 170a, 170b and 170c and mirrors 171a, 171b and 171c.

Figures 42A, 42B:
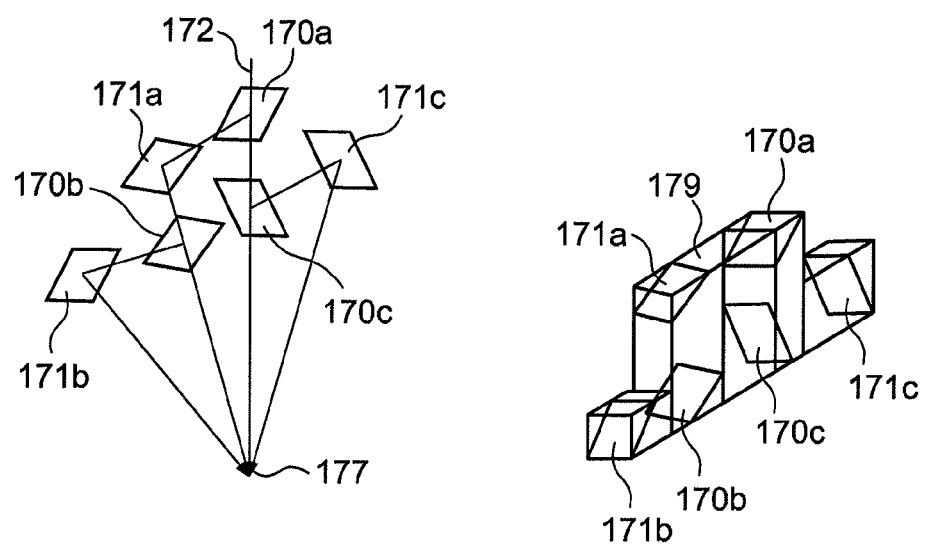
FIG. 42A shows branch of the laser light using a three-dimensional image.
FIG. 42B shows an example of a cube that realizes the branch.

For example, a case will be described where laser branches shown in FIG. 39 and FIG. 40 are configured with cubic optical devices. Branches of laser light 172 are shown in a two-dimensional image in FIG. 39 and FIG. 40. However when these are shown in a three-dimensional image, the image becomes as shown in FIG. 42. As shown in FIG. 42A, laser light 172 emitted from laser emitting apparatus 33 is once branched into a plurality of optical paths and focused on one position 177 to be irradiated finally. FIG. 42B shows an example of a cube that realizes this branch. In cube 179 shown in FIG. 42B, splitters 170a, 170b and 170c and mirrors 171a, 171b and 171c are arranged at fixed predetermined positions. In this way, by accommodating splitters 170a, 170b and 170c and mirrors 171a, 171b and 171c used for laser branch in cube 179, it is possible to make fine positioning unnecessary and emit laser light which is controlled in blanches, to the desired position only by arranging cube 179 on a laser optical axis.

Figure 63B:
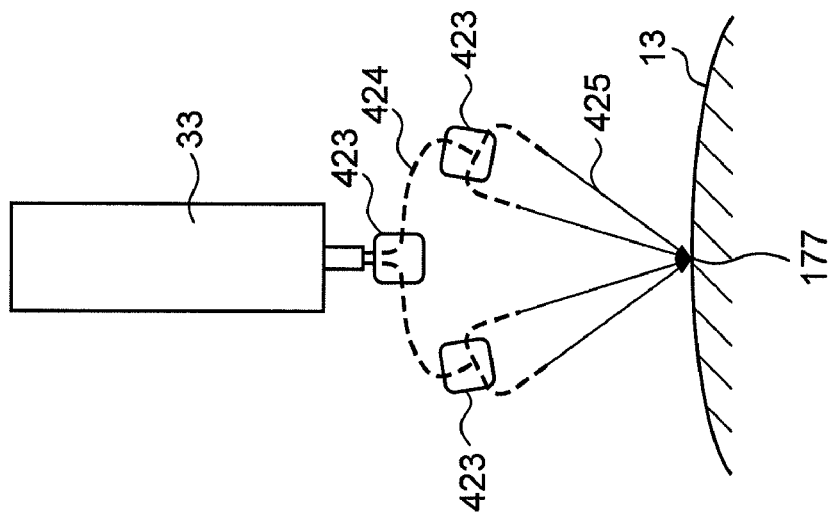
FIG. 63B shows a case where a laser light is divided into four branches.
Figure 63A:
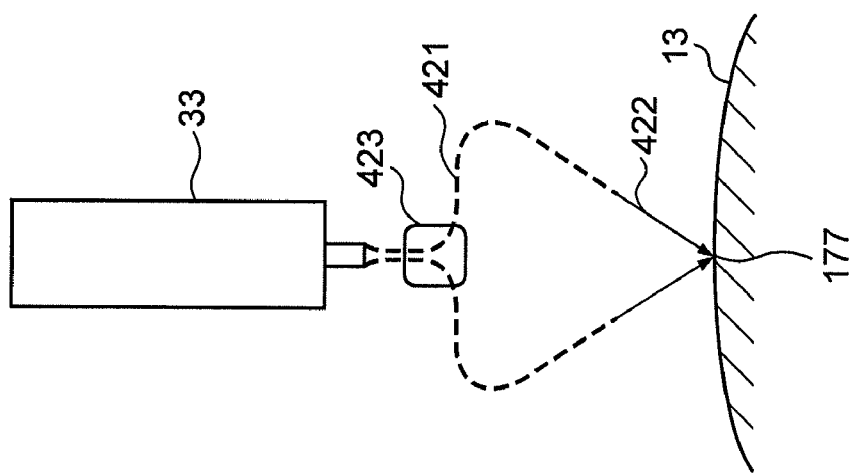
FIG. 63A shows a case where a laser light is divided into two branches.

As the method of branching a laser light, a laser light may be divided using an optical fiber. FIG. 63A and FIG. 63B show a method of branching a laser light using an optical fiber. FIG. 63A shows a case where a laser light from laser emitting apparatus 33 is divided into two branches by branch fiber cable 421. In this case, laser light 422 which is divided into two branches is emitted from this two-branch fiber cable 421 toward the same position 177 in skin 13 to be irradiated. Two-branch fiber cable 421 includes one optical fiber directional coupler 423. Further, FIG. 63B shows a case where a laser light from laser emitting apparatus 33 is divided into four branches by branch fiber cable 424. In this case, laser light 425 divided into four branches is emitted from this four-branch fiber cable 424 toward position 177 in skin 13 to be irradiated. Four-branch fiber cable 424 includes three optical fiber directional couplers 423. In this way, when an optical fiber is used, as in the case shown in FIG. 39, one laser light emitted from laser emitting apparatus 33 can be divided into a plurality of branches and puncture skin 13. Particularly, when a fiber cable is used, laser light does not leak outside, so that handling is much simpler than the case where a splitter is used.

Figure 64:
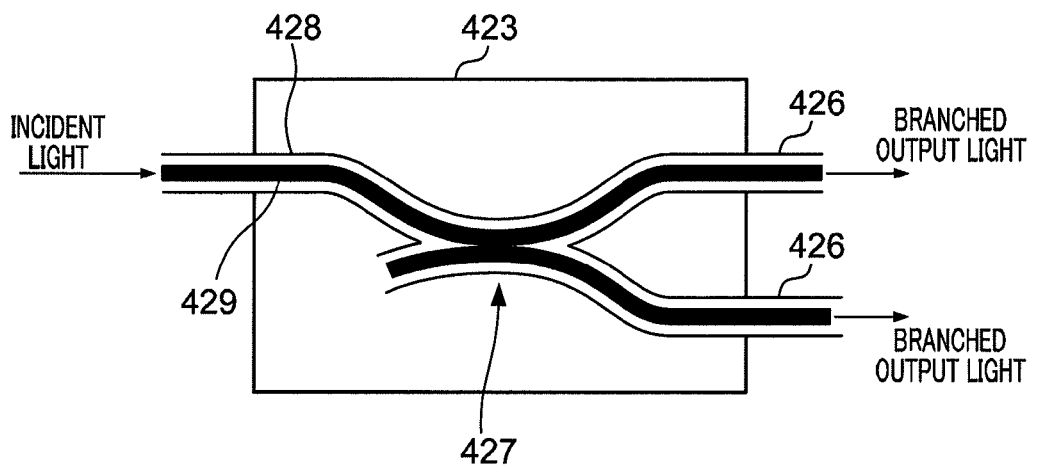
FIG. 64 is a schematic view showing the configuration of an optical fiber directional coupler used in the laser branch control of FIG. 63.

FIG. 64 is a schematic view showing the configuration of optical fiber directional coupler 423. Generally, a directional coupler is an optical device that branches a light. Optical fiber directional coupler 423 is configured by removing clads 428 of two optical fibers 426 at coupling section 427 and making cores 429 closer to each other. When light enters from one optical fiber 426, in optical fiber directional coupler 423, the light transmits to the other core 429 near the part where two cores 429 come close to each other by the interference effect of light, and the light can be branched.

Figure 65:
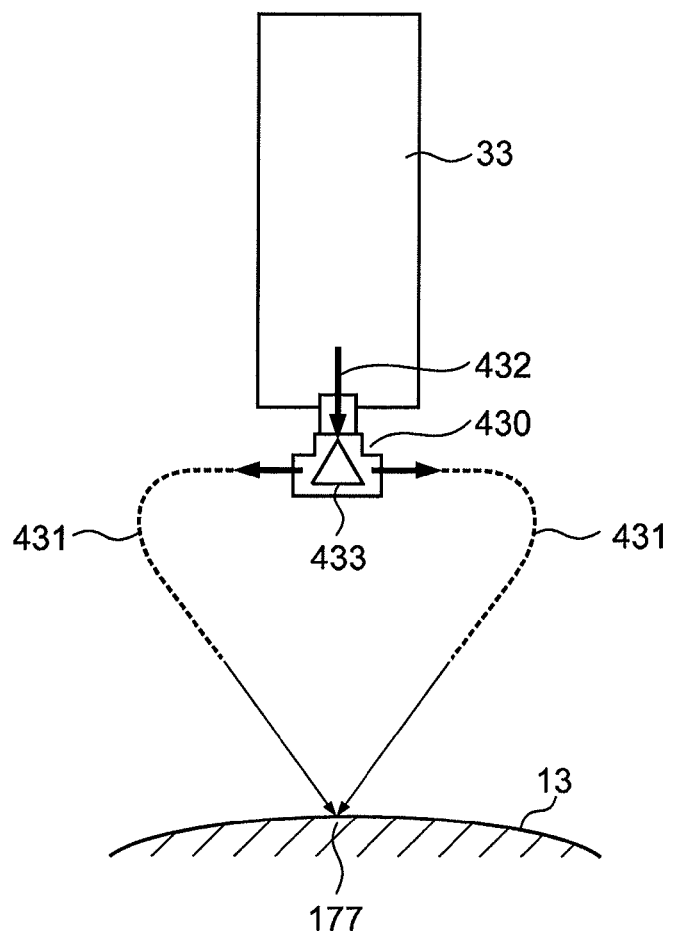
FIG. 65 shows still another example of the laser branch control in the blood test apparatus with the laser perforation apparatus of the present invention.

FIG. 65 shows a case where branch joint section 430 and fiber cable 431 are used as a means for branching laser light using an optical fiber. Here, laser light 432 emitted from laser emitting apparatus 33 is divided into two branches via branch joint section (T-branch) 430. Branch joint section 430, for example, incorporates triangular total reflection mirror 433 and branches laser light 432 in an inverted T shape. The branched laser lights puncture the same position 177 in skin 13 to be irradiated via fiber cable 431.

Generally, when skin 13 is irradiated with laser light, the irradiated part absorbs the light and its temperature increases rapidly. This increase in the temperature evaporates blood 16 and lifts skin 13 in a balloon shape. When skin 13 is further lifted, skin 13 is destroyed and blood 16 flows out. After blood 16 flows out, the bottom surface punctured with laser light is carbonized, and a carbonized odor is produced. The carbonized odor may be deodorized with a deodorizer.

This laser emitting apparatus 33 is designed so that laser light punctures skin 13 of the patient approximately 0.5 mm deep.

In this case, the type the laser light by laser emitting apparatus 33 may be Er:YAG or CO2 gas, the wavelength range may be 2.7 to 3.5 μm or 6.5 to 10.5 μm, the pulse width may be 50 to 400 μs, preferably 200 μs, and the output may be 300 mJ to 3000 mJ. Further, the diameter of a shot may be 0.1 mm to 0.5 mm, and the depth of a shot may be 0.3 to 0.7 mm. Further, the charge voltage falls in a range of 200 to 700 V, preferably 500 V. This high voltage is obtained by charging electrical charge in a capacitor using a battery and discharging this electrical charge at a burst.

The Emission Angle in Laser Emission

Figure 43:
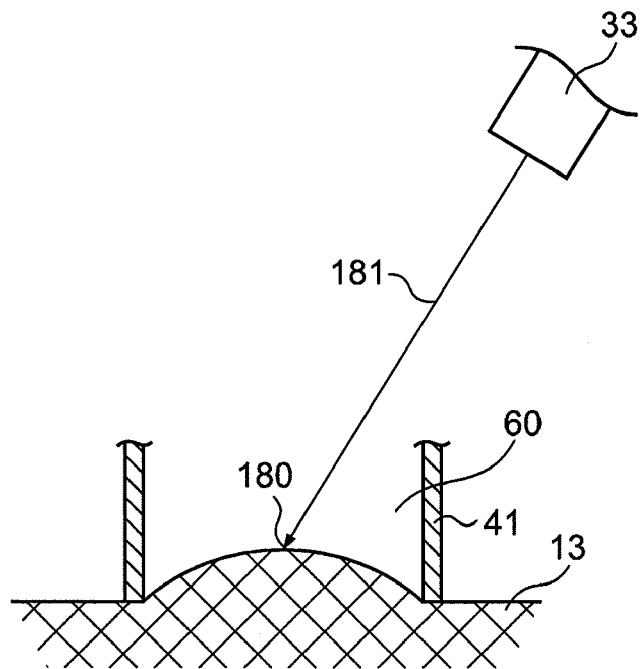
FIG. 43 shows how laser light is emitted from an oblique direction and punctures skin with the blood test apparatus of the present invention.

One laser light may be emitted from an oblique direction with respect to skin 13 and puncture skin 13. In FIG. 43, a negative pressure is created in negative pressure chamber 60 of blood sensor unit 44 by negative pressure means 34, and skin 13 is lifted. The incident angle of laser light 181 is less than 90 degrees with respect to the direction of the tangent to top 180 of the lifted skin 13. In this way, when the incident angle of laser light is less than 90 degrees with respect to the direction of the tangent to top of the lifted skin compared to a case where laser light is emitted from a vertical direction, laser light 181 is emitted from an oblique direction with respect to the surface where blood capillaries are crowded. Therefore, although the emission intensity per unit area of laser light 181 decreases, laser light 181 is more likely to damage the blood capillaries. Therefore, blood collection efficiency improves. Accordingly, even when the depth of puncturing is shallow, blood 16 can be collected enough, and the pain of the patient is alleviated.

Figure 44:
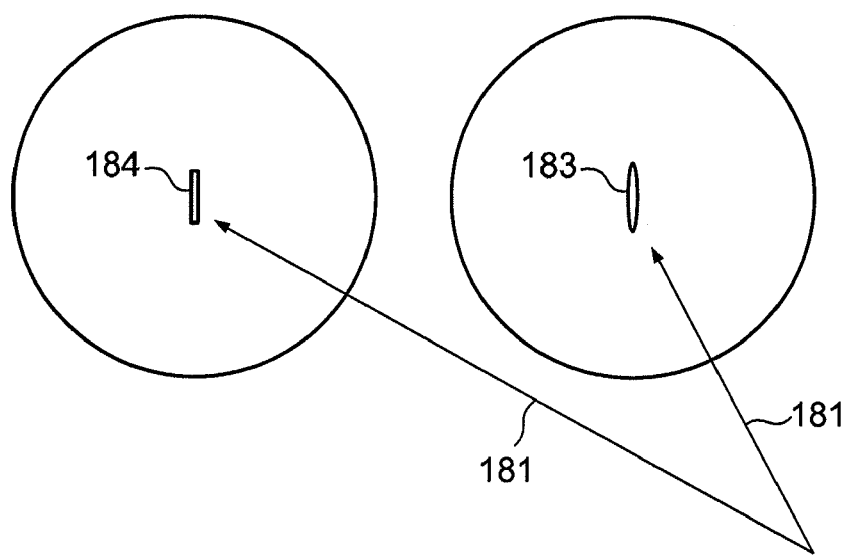
FIG. 44 shows variations in the shape of emission of the laser light.

Further, the shape of emission of laser light 181 does not have to be round, and, as shown in FIG. 44, may be ellipse 183 or rectangle 184. When the shape of emission is made ellipse 183 or rectangle 184, laser light 181 is more likely to damage the crowded blood capillaries, and blood collection efficiency improves. Therefore, blood 16 can be collected enough with puncturing only a shallow depth, and so the pain of the patient can be alleviated.

Figure 45:
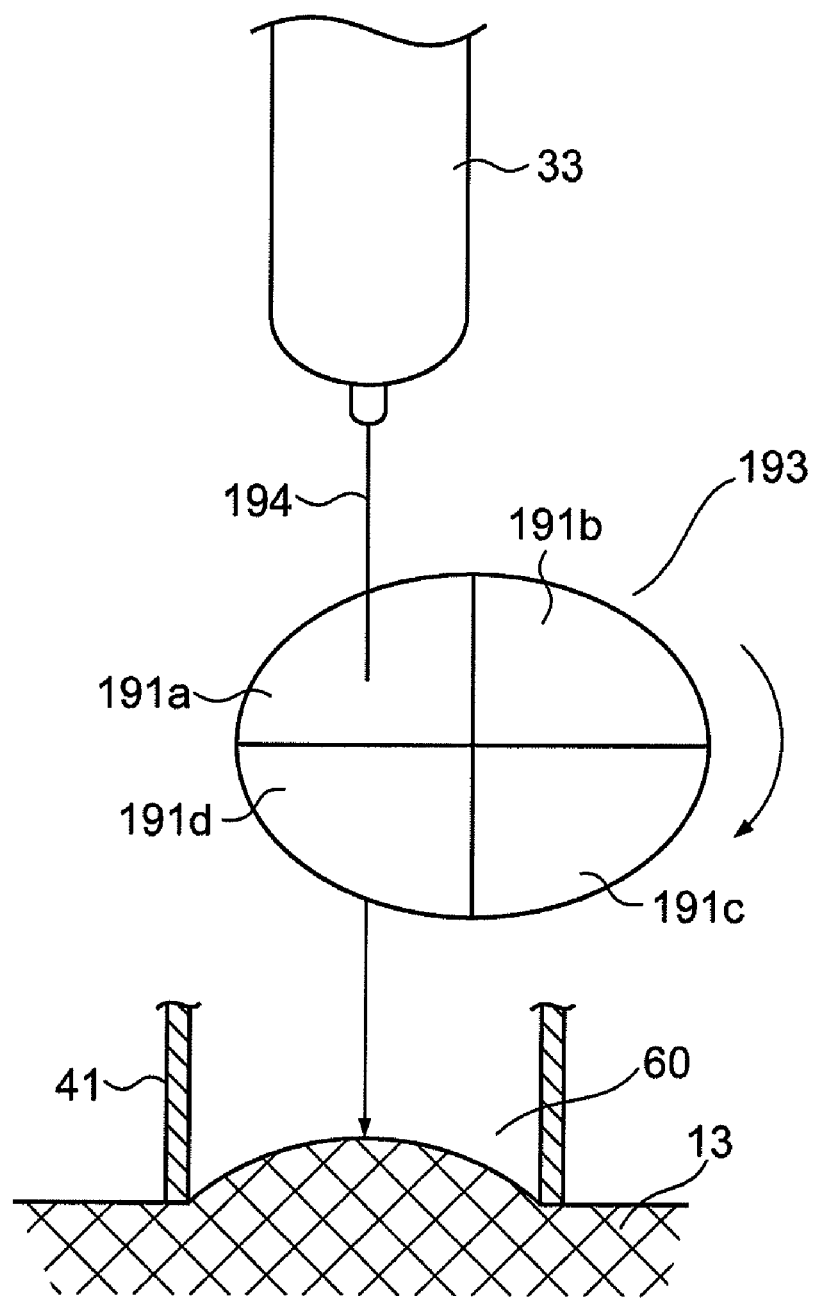
FIG. 45 is a schematic view showing another example of laser output control in the blood test apparatus of the present invention.

In blood test apparatuses 31 and 31a of the present invention, the laser output intensity can be made variable even with one laser emitting apparatus 33. As shown in FIG. 45, a plurality of types of filters that transmit different amounts of light, for example, plate 193 that is applied with neutral density (ND) filters 191a to 191d, may be provided between laser emitting apparatus 33 and skin 13. Plate 193 is arranged in the emission path of laser light 194. By rotating plate 193, the amount of laser light 194 emitted on skin 13 is controlled. By controlling the amount of laser light, the depth of puncturing can be controlled.

By this means, in addition to the conventional method which has been performed to control laser intensity, of controlling the applied voltage in a case of a flashlamp and controlling the current in a case of semiconductor laser, the output of laser puncturing can be adjusted using an ND filter.

Therefore, more precise laser output control is possible. Further, in another application, when laser output intensity is determined by the voltage applied to the flashlamp, making the voltage variable may cause deterioration of the stability of the voltage value and fluctuation of laser output. To solve this problem, by a fixed voltage and using ND filters 191a to 191d that transmit different amount of light even when the output of laser light 194 decreases (changes), it is possible to maintain the output of the laser light constant. Therefore, it is possible to provide stable laser output.

Pulse Control (Time Division) in Laser Emission

Figure 46:
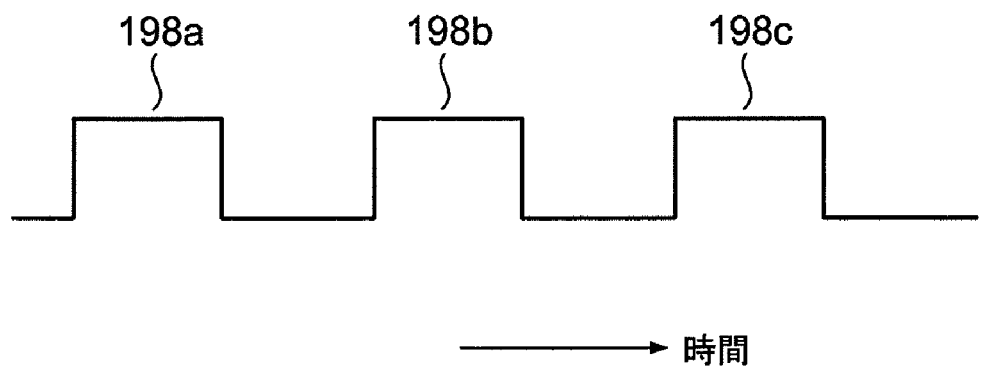
FIG. 46 shows an example of laser pulse control in the blood test apparatus of the present invention.
Figure 47:
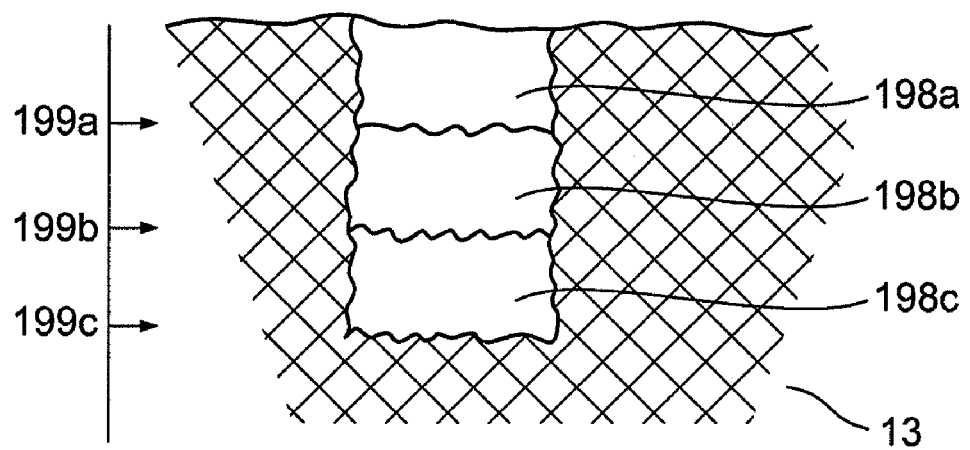
FIG. 47 is a cross-sectional view showing a puncturing state by the laser pulse control in FIG. 46.

To alleviate the pain upon puncturing, the skin may be punctured a plurality of times up to a certain depth. Compared to the method of puncturing the skin once using a large pulse with approximately 320 V as a charge voltage, as shown in FIG. 46, laser light is divided into three pulses 198a, 198b and 198c, and the skin is punctured a plurality of times using these small pulses with approximately 210 V at intervals (i.e., intermission periods) of 200 μs to 1 msec. By this means, as shown in FIG. 47, skin 13 can be punctured in three stages of level 199a, 199b and 199c that match pulses 198a, 198b and 198c, respectively. In this case, a capacitor is charged in intermission periods of 200 μs to 1 msec and a high voltage is obtained.

According to the control of this puncturing method, the depth skin 13 is punctured with one pulse is shallow, so that it is possible to alleviate the pain and puncture the skin to a predetermined depth. In this case, it is important to make the intervals between pulses 198a, 198b and 198c short, between 200 μs and 1 msec, and the next puncturing is preferably performed before blood 16 leaks.

Further, to alleviate the pain upon puncturing, as another method for puncturing the skin a plurality of times up to a predetermined depth, a method of making laser light variable on a continuous basis and performing fractionated emission, will be described. The part to be punctured with the present invention is, for example, the skin of the finger cushion. The skin is formed, in order from the surface, with the epidermis that has the stratum corneum outside and the dermis where pain points and blood capillaries exist. Therefore, by providing energy that removes only the epidermis by the first emission or by a plurality of emissions and then puncturing the dermis with little energy, the pain is alleviated.

Figure 48C:
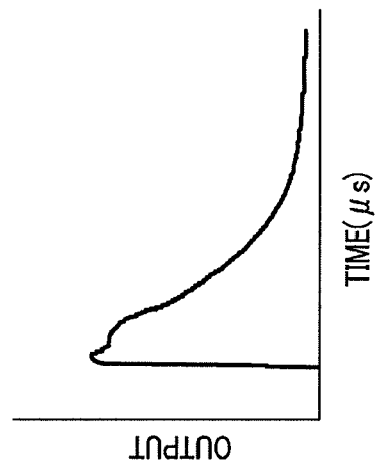
FIG. 48C shows time fluctuation of a laser output.
Figure 48B:
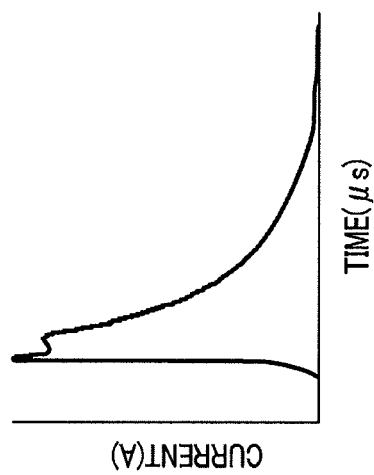
FIG. 48B shows time fluctuation of the current inputted to a flashlamp over time.
Figure 48A:
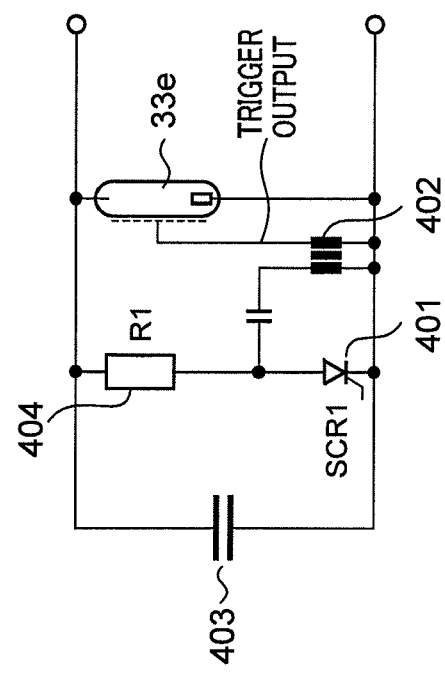
FIG. 48A shows a circuit diagram.

For example, when laser rod (laser crystal) 33d which is formed with Er:YAG doped with erbium and which is φ2.5 mm and 52 mm long, is used, a large pulse of approximately 450 V is used as the charge voltage to flashlamp (excitation light source) 33e in one puncturing. FIG. 48A shows the circuit for causing the operation described above, FIG. 48B shows the current inputted to flashlamp 33e, and FIG. 48C shows the output of the laser light. In the circuit diagram of FIG. 48A, when thyristor (SCR 1) 401 is turned on, a boosted voltage of several kV, is outputted from trigger coil 402, the xenon gas filling flashlamp 33e is ionized, main discharge of electrolytic capacitor 403 is started, and flashlamp 33e emits light. By this emission of light from flashlamp 33e, laser rod 33d is excited, and laser light is emitted. The reference numeral "404" is resistance (R1). In the above-described case, the skin is punctured in one time.

Figure 49C:
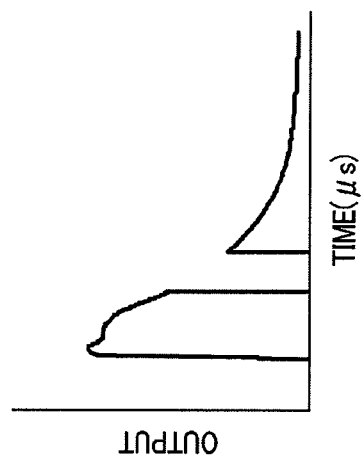
FIG. 49C shows time fluctuation of the laser output.
Figure 49B:
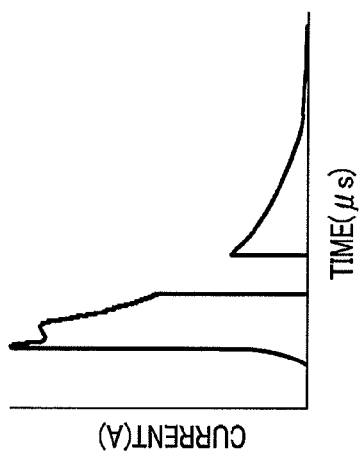
FIG. 49B shows time fluctuation of the current inputted to the flashlamp over time.
Figure 49A:
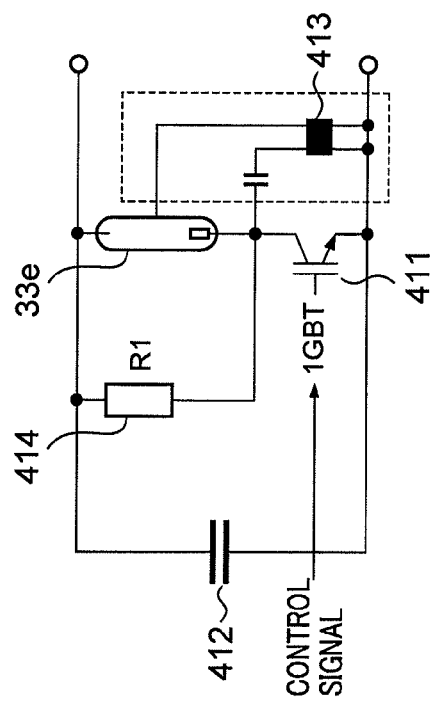
FIG. 49A shows a circuit diagram.

Next, a case will be described where laser light is emitted at several separate times by charging the electrolytic capacitor once. FIG. 49A, FIG. 49B and FIG. 49C show the circuit diagram, the current inputted to flashlamp 33e and the output of laser light at this time, respectively.

Referring to the circuit diagram of FIG. 49A, in order to make flashlamp 33e emits light divided in several times, when a "high" signal is inputted to transistor (IGBT) 411 with a large current and high switching speed, the negative terminal of flashlamp 33e is grounded when transistor (IGBT) 411 is turned on, a voltage from electrolytic capacitor 412 is applied to flashlamp 33e, and, at the same time, a boosted voltage of several kV is outputted from trigger coil 413. By this means, the xenon gas filling flashlamp 33e is ionized, main discharge of electrolytic capacitor 412 is started, and flashlamp 33e emits light. Next, when a "low" signal is inputted to transistor (IGBT) 411, transistor (IGBT) 411 is turned off, and the voltage stops being applied to flashlamp 33e. By this means, flashlamp 33e stops emitting light and stops outputting laser light. By repeating this operation, it is possible to divide laser output into several times. Here, a case has been described where laser light is outputted in two outputs. The reference numeral "414" is resistance (R1).

As is clear from FIG. 49C, laser light can be emitted with high power at first and then emitted with low power. When laser rod 33d of Er:YAG with φ2.5 mm and 52 mm long described in the present example is used, the minimum voltage of flashlamp 33e for emitting laser light is 370 V, and so it is necessary to set the first voltage higher than 370 V and to shorten the emission time of flashlamp 33e in order to reduce total energy. The second voltage applied to flashlamp 33e is set a low voltage of 370 V. By this means, it is possible to puncture skin 13 in two stages, levels 199a and 199b (see FIG. 47). According to the control of this puncturing method, the epidermis of skin 13 is removed first and then the dermis is punctured with little energy, and so laser light does not reach the deep part underneath the dermis, so that it is possible to alleviate the pain and puncture the skin to a predetermined depth. The epidermis is punctured so that blood 16 does not leak.

Power Supply Control

The blood test apparatus of the present invention has a laser emitting apparatus that consumes a large amount of power, and so the management of the power supply is important. In a case of a portable device that uses a battery as the power supply, the capacity is limited, and so the management of the power supply is particularly important. Further, when the apparatus influences safety of life, for example, measures the blood sugar level, cases must be avoided where measurement cannot be performed due to power exhaustion, and it is important that at least a blood test (for example, measurement of the blood sugar level) can be conducted.

The blood test apparatus of the present invention preferably has a power supply control circuit that controls a power supply for driving the laser emitting apparatus included in the apparatus and a power supply for driving the electrical circuit section. Further, the power supply control circuit preferably controls the power supply for driving the laser emitting apparatus and the power supply for driving the electrical circuit section separately. "Controlling separately" means determining whether to supply power for driving the laser emitting apparatus and power for driving the electrical circuit section according to the remaining power supply (particularly, battery) level and the voltage, and determining from which power supply, power is supplied.

The power supply in the blood test apparatus of the present invention preferably has a battery power supply, so that the blood test apparatus can be a portable device. There may be one battery power supply or two or more battery power supplies. A battery may be a secondary battery or a primary battery, or a combination of both batteries. Examples of the secondary battery include a lithium-ion battery, lithium polymer battery and nickel hydride battery. Examples of the primary battery include a lithium battery, manganese cell, alkali cell and oxyride dry-cell battery.

Further, the power supply of the blood test apparatus of the present invention may have a connection terminal for an emergency power supply in addition to a battery power supply to connect to other power supplies in order to use the blood test apparatus when the battery of the battery power supply runs down. Examples of the emergency power supply include a dry cell which is easily available, a USB terminal which is used in, for example, personal computers, a fuel cell and a hand dynamo. These power supplies can be connected in a simple manner.

Further, the power supply of the blood test apparatus of the present invention may have an external power supply in addition to a battery power supply. When the apparatus is connected to an external power supply, preferably, the external power supply is used preferentially, and electrical power supply from a battery is stopped or the battery is charged.

The blood test apparatus may have a battery level measuring circuit for measuring the remaining battery level of a battery power supply. Further, the blood test apparatus preferably has a comparing section that compares the remaining battery level measured by the battery level measuring circuit with a predetermined voltage value (electrical level), so as to figure out the remaining battery level and to determine whether it is possible to perform laser puncturing or a test.

As described above, the comparing section stores predetermined electrical levels. The first of the predetermined electrical levels is the electrical level required for the predetermined number of times of tests (including the laser puncturing and measurement). This value is referred to as the first battery level threshold. When the remaining battery level is lower than the first battery level threshold, a warning (battery level warning) is preferably issued to encourage the user to change the battery. The first battery level threshold may be set as appropriate according to designed circuits and is basically a fixed value.

The second of the predetermined electrical levels is the electrical level required for one test (including the puncturing and measurement). This value is referred to as the second battery level threshold. When the remaining battery level is equal to or higher than the second battery level threshold, the apparatus determines that at least one test can be performed, and conducts a test. As described above, when the remaining battery level is lower than the first battery level threshold, a battery level warning is preferably issued. On the other hand, when the measured battery level is lower than the second battery level threshold, a normal test cannot be performed, and so, preferably, laser puncturing is not allowed, and the user is informed that a test cannot be performed (i.e., a message of unavailability is shown). However, there is a case where, although laser puncturing is not possible, measurement process which consumes small power can be performed. Therefore, it is possible to perform measurement after performing puncturing using means other than laser light.

The second battery level threshold is preferably set based on the battery power consumption level consumed in the previous test. To be more specific, the second battery level threshold is preferably a sum of the battery power consumption level and the electrical level required to drive the electrical circuit for measurement. The battery power consumption level changes according to a change of laser output setting of the laser emitting apparatus, and so the latest data of the battery power consumption consumed in the test is stored. In this way, the second battery level threshold is variable.

The third of the predetermined electrical levels is a sum of the electrical level required to charge the laser emitting apparatus once and the electrical level required to drive the electrical circuit for measurement. This value is referred to as the third battery level threshold. When the power supply for charging the laser emitting apparatus and the power supply for driving the electrical circuit are different, the third battery level threshold is used as a criterion for determining whether an emergency power supply for driving the electrical circuit is used to charge the laser emitting apparatus. The electrical level required to charge the laser emitting apparatus once is determined according to the capacity of the capacitor that is charged for laser excitation, the charge current and the internal resistance of the battery.

Setting of a Charge Current Value According to the Remaining Battery Level

Figure 61A:
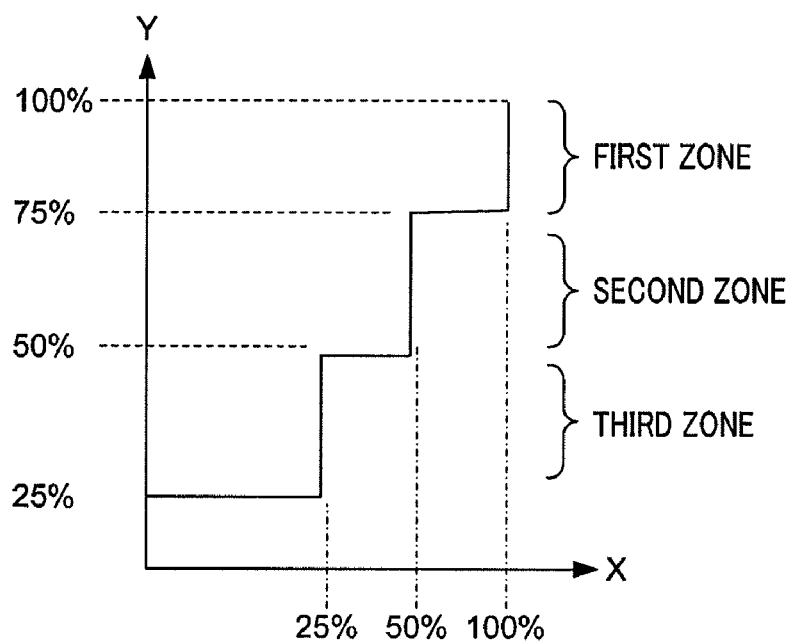
FIG. 61A is a graph illustrating a method of setting a charge level for charging the laser emitting apparatus stepwise based on the battery level.
Figure 61B:
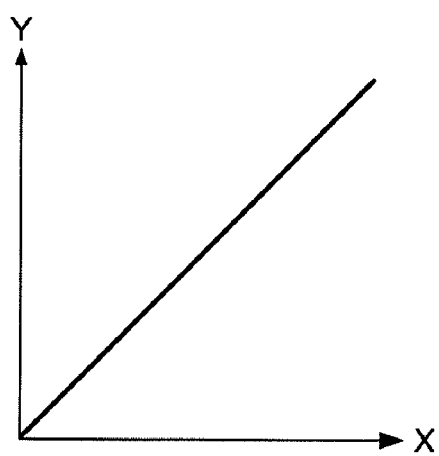
FIG. 61B is a graph illustrating a method of setting the charge level for charging the laser emitting apparatus continuously based on the battery level.
Figure 61C:
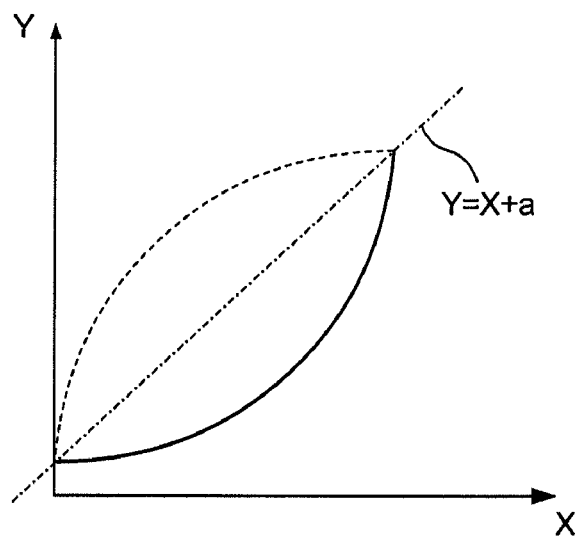
FIG. 61C is a graph illustrating a method of setting a charge level for charging the laser emitting apparatus according to a variable curve based on the battery level.

Further, the charge level for charging the laser emitting apparatus may be set based on the remaining battery level measured in the battery level measuring circuit. FIG. 61A to FIG. 61C show examples of setting the charge level based on the remaining battery level. FIG. 61A shows a method of changing the charge current stepwise according to the proportion of the remaining battery level (Y axis). For example, when the remaining battery level is 75 to 100% (first zone), the charge current is set to a maximum value (100%); when the remaining battery level is 50 to 75% (second zone), the charge current value is set to 50% of the maximum value; and when the remaining battery level is 25 to 50% (third zone), the charge current value is set to 25% of the maximum value. FIG. 61B shows a method of changing the charge current (X axis) continuously proportional to the remaining battery level (Y axis). FIG. 61C shows a method of changing the charge current (X axis) continuously based on the change curve of the proportion of the remaining battery level (Y axis) so that the curve shows a variable curve that is a reverse of the change curve. FIG. 61C shows the control performed in accordance with a curve symmetric about the proportional line of "Y=X+a (a: offset)."

The blood test apparatus of the present invention preferably has a battery voltage measuring circuit for measuring the battery voltage of the battery power supply. Further, the blood test apparatus preferably has a comparing section that compares the battery voltage measured by the battery voltage measuring circuit with a predetermined voltage value.

Cases occur where, even if the electrical level required for a test (puncturing and measurement) remains in the battery, when the laser emitting apparatus is charged for laser puncturing, the battery voltage becomes lower than the voltage required to drive the electrical circuit section for measurement. Therefore, cases occur where, although there is enough remaining battery level for measurement, measurement cannot be performed. Therefore, the battery voltage measuring circuit checks whether the battery can output a sufficient voltage.

As described above, the comparing section stores predetermined voltage values. The first of the predetermined voltage values is preferably a certain level higher than the minimum voltage required to drive the electrical circuit section for measurement. This voltage value is referred to as the first voltage threshold. The first voltage threshold is set so that, even if a battery voltage decreases by charging the laser emitting apparatus, the battery voltage is not lower than the minimum required voltage. How much the battery voltage decreases by the charging depends on the property of the battery, and so the first voltage threshold is set as appropriate according to the property of the battery.

When the comparing section determines that the battery voltage measured by the battery voltage measuring circuit before the laser emitting apparatus is charged, is lower than the first voltage threshold, the laser emitting apparatus is preferably charged with a lower current than the normal current, because the battery voltage is less likely to decrease when the laser emitting apparatus is charged with a lower current.

Figure 62:
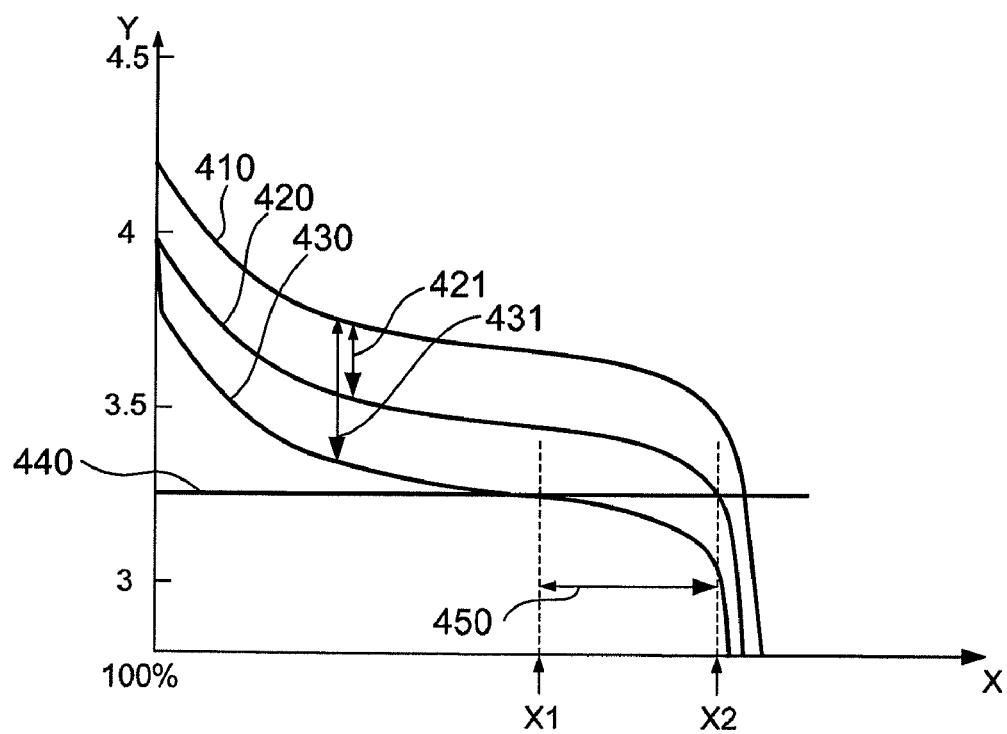
FIG. 62 shows the relationship between the battery voltage (Y axis) and the battery level (X axis) when the charge level is changed.

FIG. 62 shows the relationship between the battery voltage (Y axis) and the remaining battery level (X axis) when the charge level is changed. Curve 410 shows the relationship between the battery voltage (Y axis) and the remaining battery level (X axis), when the charge current is 0 (no load); curve 420 shows the relationship between the battery voltage (Y axis) and the remaining battery level (X axis) when the charge current is I; and curve 430 shows the relationship between the battery voltage (Y axis) and the remaining battery level (X axis) when the charge current is I' (>I). Curve 420 and curve 430 show that the battery voltages are lower than curve 410. This is caused by the resistance (421 and 431) inside the battery. When the voltage level required to drive the electrical circuit for measurement is set 440, in a case where the charge current is I (curve 420), the battery can drive the electrical circuit until the remaining battery level is X2. On the other hand, when the charge current is I' (>I) (curve 430), the battery can no longer drive the electrical circuit once the remaining battery level is X1. In this way, when the charge current is lowered, a decrease of the battery voltage is controlled. Significant decrease of the battery voltage is not preferable, because battery energy which cannot be used increases as shown by 450.

The second of the voltage values determined in advance in the comparing section is equal to or higher than the first voltage threshold and has primarily a sufficient margin. This voltage value is referred to as the second voltage threshold. For example, the second voltage threshold is approximately 0.5 to 1 V higher than first voltage threshold.

When the comparing section determines that the battery voltage measured by the battery voltage measuring circuit before the laser emitting apparatus is charged, is higher than the second voltage threshold, the laser emitting apparatus is preferably charged with a higher charge current.

The blood test apparatus of the present invention has a display section (see FIG. 1) that displays the test result of a blood test. The above-described messages for battery level warning and unavailability are preferably displayed on the display section.

A First Example of a Power Supply Controlling Section

Figure 50:
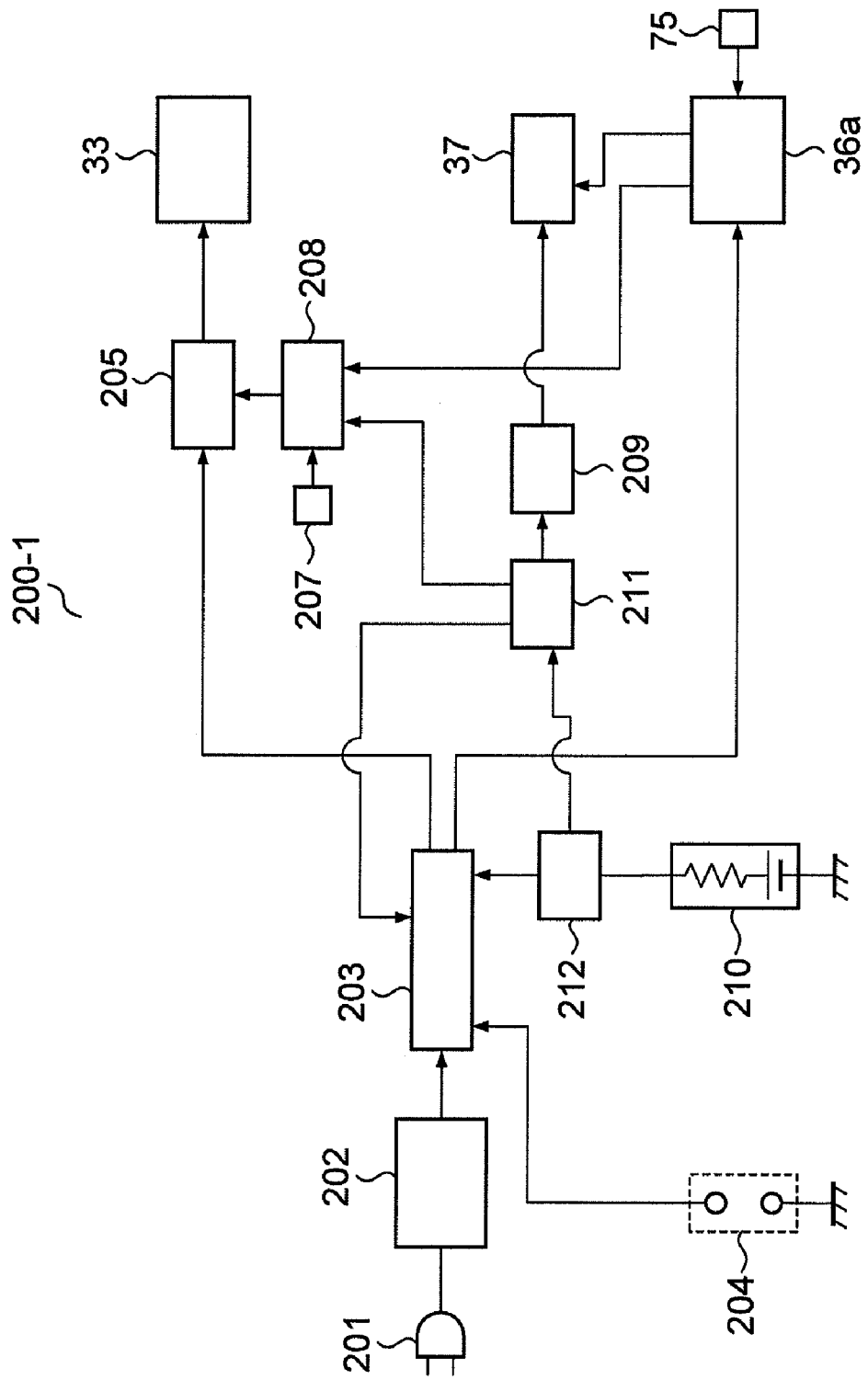
FIG. 50 is a block diagram showing a first example of a power supply controlling section of the blood test apparatus of the present invention.

FIG. 50 shows a first example of power supply controlling section 200-1 of the blood test apparatus. In FIG. 50, outlet 201 connected to a household AC power supply (used as an example of an external power supply) is connected to AC adapter 202. The output of AC adapter 202 can be connected to one input of power supply controlling circuit 203 removably, using a connector. Battery 210 is connected to battery level and battery voltage measuring circuit 212. The first output of circuit 212 is connected to power supply controlling circuit 203, and the second output of circuit 212 is connected to comparing section 211. Connection terminal 204 for an emergency power supply is connected to power supply control circuit 203.

When power supply control circuit 203 is connected to AC adapter 202, power supply control circuit 203 controls so that the power supply of AC adapter 202 is preferentially used and battery 210 is not used. When the voltage outputted from AC adapter 202 is detected and this voltage is outputted, supply from battery 35 is stopped forcibly or battery 210 is charged.

The first output of power supply control circuit 203 is connected to electrical circuit section 36*a*. The second output of power supply control circuit 203 is connected to the input of boost circuit 205, and the output of boost circuit 205 is connected to laser emitting apparatus 33.

The first output of comparing section 211 is connected to power supply control circuit 203. The second output of comparing section 211 is connected to boost controlling section 208, and the output of boost controlling section 208 is connected to boost circuit 205. The third output of comparing section 211 is connected to display controlling section 209, and the output of display controlling section 209 is connected to display section 37.

Puncture button 75 is connected to the input of electrical circuit section 36*a*, and the signal caused by pressing puncture button 75 is connected to the input of boost controlling section 208 via electrical circuit section 36*a*. Emergency button 207 is connected to the other input of boost controlling section 208. The output of electrical circuit section 36*a* is connected to display section 37.

Figure 51:
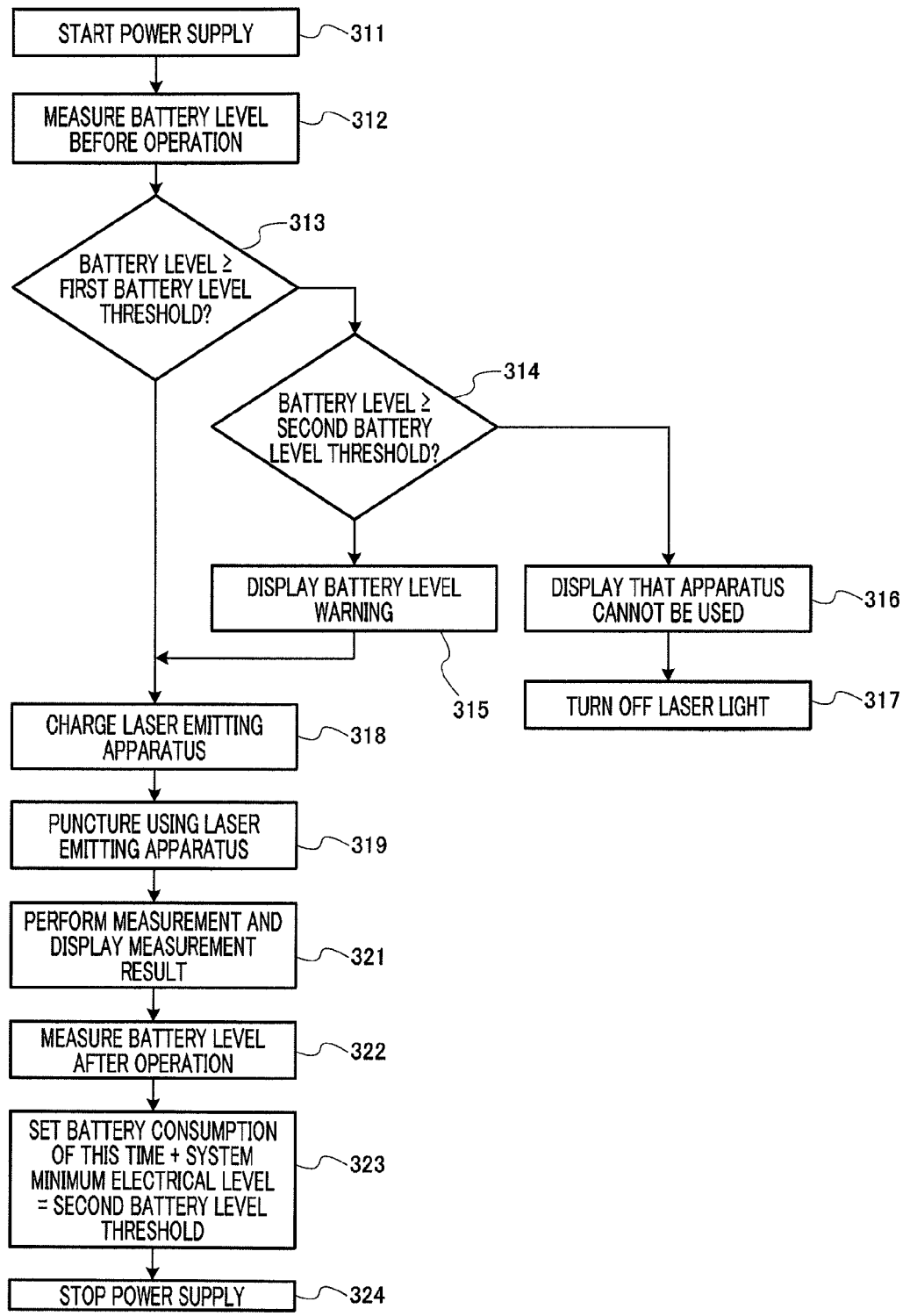
FIG. 51 is a flowchart showing a first example of control steps in the power supply controlling section of FIG. 50.

A first example of the operation of power supply controlling section 200-1 shown in FIG. 50 will be described with reference to FIG. 51. In step 311, the power supply is started. Next, in step 312, the remaining battery level is measured. In step 313, the measured battery level is compared with the first battery level threshold, and, in step 314, the remaining battery level is compared with the second battery level threshold. The first battery level threshold refers to the electrical level required for a predetermined number of times of tests (including the laser puncturing and measurement), and the second battery level threshold refers to the electrical level required for one test (including the puncturing and measurement).

When the remaining battery level is determined to be equal to or higher than the first battery level threshold in step 313, the flow shifts to step 318, and the laser emitting apparatus is charged. When the remaining battery level is determined to be lower than the first battery level threshold in step 313 and determined to be equal to or higher than the second battery level threshold in step 314, a battery level warning is displayed in step 315 to encourage the user to change the battery, and, onto step 318, the laser emitting apparatus is charged. When the remaining battery level is determined to be lower than the first battery level threshold in step 313 and determined to be lower than the second battery level threshold in step 314, a message of unavailability is displayed on the display section in step 316 to inform the user that a normal test cannot be performed, and power supply to the laser emitting apparatus is not allowed in step 317.

When the laser emitting apparatus is charged with a predetermined level, laser light is emitted in step 319 and the skin is punctured. The component in blood flowing out from the skin punctured in step 321 is measured, the obtained measurement result is displayed, and then the blood test is finished.

After the test, the remaining battery level is measured in step 322. In step 323, the battery consumption level of this time is calculated, wherein the battery consumption level is the difference between the remaining battery level measured in step 312 and the remaining battery level measured in step 322. Further, in step 323, the second battery level threshold is reset, wherein the second battery level threshold is the sum of the battery consumption level of this time and the minimum electrical level required to drive the electrical circuit section. In step 324, the power supply is stopped.

Figure 52:
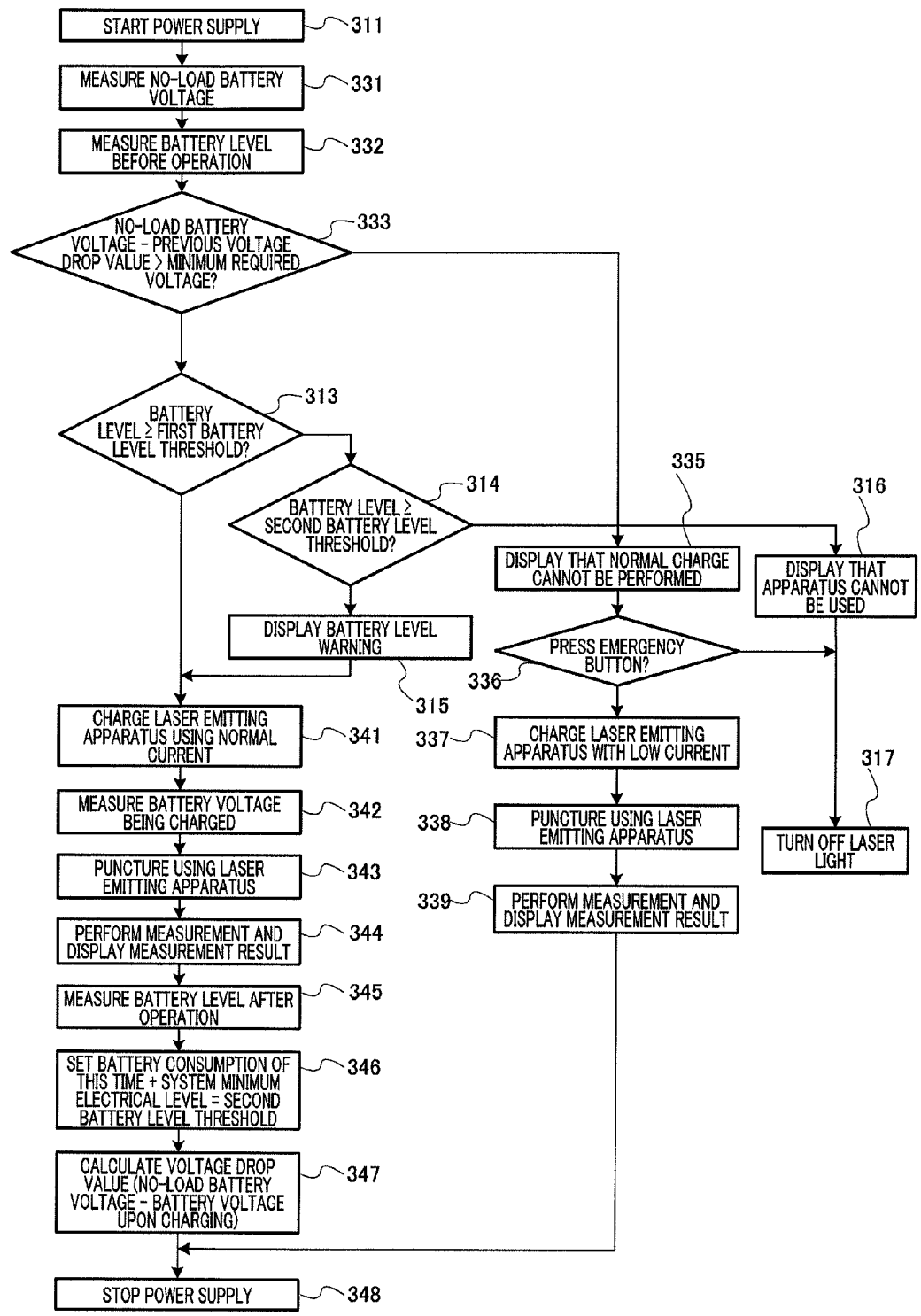
FIG. 52 is a flowchart showing a second example of the control steps in the power supply controlling section of FIG. 50.

A second example of the operation of power supply controlling section 200-1 shown in FIG. 50 will be described with reference to FIG. 52. In step 311, the power supply is started. In step 331, the battery voltage is measured, and, in step 332, the remaining battery level is measured.

In step 333, the difference between the voltage measured in step 331 and the voltage drop value calculated in step 347 (described later) in the previous test, is calculated. Further, in step 333, this difference is compared with the minimum voltage required to drive the electrical circuit section. In step 313, the remaining battery level measured in step 332 is compared with the first battery level threshold, and, in step 314, the remaining battery level measured in step 332 is compared with the second battery level threshold. As described above, the first battery level threshold refers to the electrical level required for the predetermined number of times of tests (including the laser puncturing and measurement), and the second battery level threshold refers to the electrical level required for one test (including the puncturing and measurement).

When the difference is determined to be equal to or higher than the minimum required voltage in step 333 and the remaining battery level is determined to be equal to or higher than the first battery level threshold in step 313, step 341 is started, and the laser emitting apparatus is charged with a normal current. When the difference is determined to be equal to or higher than the minimum required voltage in step 333 and the remaining battery level is determined to be lower than the first battery level threshold in step 313, a battery level warning is displayed in step 315 to encourage the user to change the battery, the flow shifts to step 341, and the laser emitting apparatus is charged with a normal current. When the difference is determined to be equal to or higher than the minimum required voltage in step 333 and the remaining battery level is determined to be lower than the first battery level threshold in step 313 and determined to be lower than the second battery level threshold in step 314, a message that the apparatus cannot be used is displayed in step 316 to inform the user that a normal test cannot be performed, and power supply to the laser emitting apparatus is not allowed in step 317.

On the other hand, if the difference is determined to be lower than the minimum required voltage in step 333, step 335 is started, and a message that normal charge cannot be performed is displayed to inform the user that the laser emitting apparatus cannot be charged normally (for example, the charging duration becomes long), and the user is requested to press an emergency button when a test is performed, in step 336.

When the emergency button is not pressed in step 336, step 317 is started, and power supply to the laser emitting apparatus is not allowed. When the emergency button is pressed in step 336, the laser emitting apparatus is charged with a lower current than usual in step 337. A current value for charging is controlled by boost controlling section 208. In step 338, the laser emitting apparatus emits laser light and punctures the skin, and, in step 339, measures the component in blood flowing out from the skin punctured in step 339 and displays the measurement result. After the test, the power supply is stopped in step 348.

On the other hand, when the laser emitting apparatus is charged with a normal current in step 341, the voltage of the battery charging the laser emitting apparatus is measured in step 342. In step 343, the charged laser emitting apparatus emits laser light and punctures the skin. In step 344, the component in blood flowing out from the punctured skin is measured, and the measurement result is displayed. In step 345, the remaining battery level after the measurement is measured.

In step 346, the battery consumption level of this time is calculated, wherein the battery consumption level of this time is the difference between the remaining battery level measured in step 332 and the remaining battery level measured in step 345. Further, in step 346, the second battery level threshold is reset, wherein the second battery level threshold is the sum of the battery consumption level of this time and the minimum electrical level required to drive the electrical circuit section for measurement. Further, in step 347, the voltage drop value is calculated, wherein the voltage drop value is the difference between the voltage measured in step 331 and the voltage measured in step 342. The voltage drop value is used in step 333 (described above) in the next test. Then, the power supply is stopped in step 348.

Figure 53:
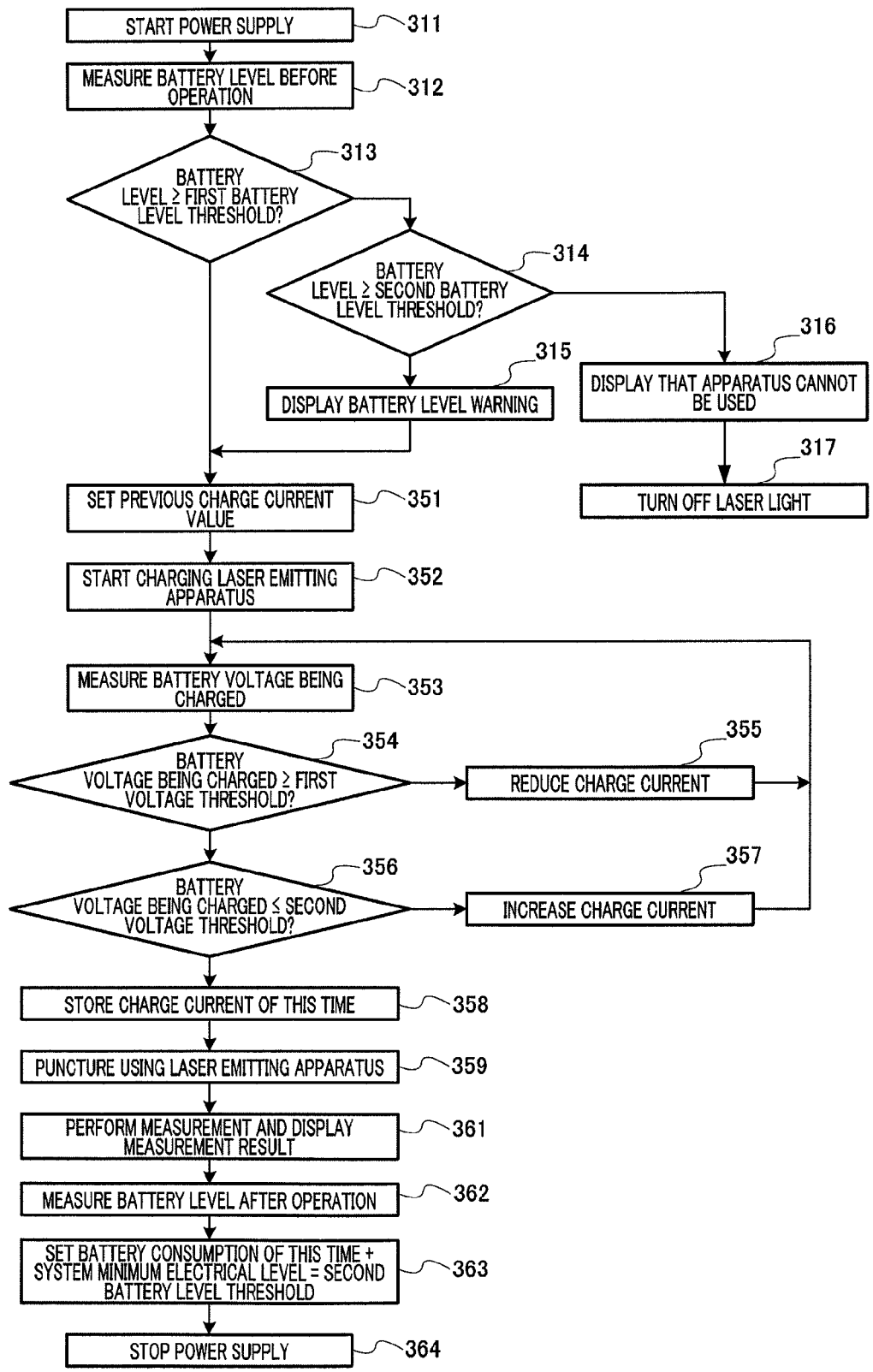
FIG. 53 is a flowchart showing a third example of the control steps in the power supply controlling section of FIG. 50.

A third example of the operation of power supply controlling section 200-1 shown in FIG. 50 will be described with reference to FIG. 53. In step 311, power supply is started. Next, in step 312, the remaining battery level is measured. In step 313, the measured battery level is compared with the first battery level threshold, and, in step 314, the measured battery level is compared with the second battery level threshold. As described above, the first battery level threshold refers to the electrical level required for the predetermined number of times of tests (including the laser puncturing and measurement), and the second battery level threshold refers to the electrical level required for one test (including the puncturing and measurement).

When the remaining battery level is determined to be equal to or higher than the first battery level threshold in step 313, step 351 is started, and the charge current value (see step 358 described later) for charging the laser emitting apparatus in the previous test is set as the charge current value in the present test. When the remaining battery level is determined to be lower than the first battery level threshold in step 313 and determined to be equal to or higher than the second battery level threshold in step 314, a battery level warning is displayed in step 315 to encourage the user to change the battery, step 351 is started, and the charge current value (see step 358) for charging the laser emitting apparatus in the previous test is set as the charge current value in the present test. When the remaining battery level is determined to be lower than the first battery level threshold in step 313 and determined to be lower than the second battery level threshold in step 314, a message of unavailability is displayed to inform the user that a test cannot be performed in step 316, and power supply to the laser emitting apparatus is not allowed in step 317.

In step 352, the laser emitting apparatus is charged with the charge current value set in step 351. When the battery is changed or the type of the power supply is changed, the laser emitting apparatus is charged with a predetermined charge current value. In step 353, the voltage of the battery charging the laser emitting apparatus is measured. In step 354, the voltage of the battery charging the laser emitting apparatus is compared with the first voltage threshold. In step 356, the voltage of the battery charging the laser emitting apparatus is compared with the second voltage threshold. As described above, the first voltage threshold is a certain level higher than the minimum voltage required to drive the electrical circuit section for measurement, and the second voltage threshold primarily has a sufficient margin. This voltage value is referred to as the second voltage threshold. For example, the second voltage threshold is approximately 0.5 to 1 V higher than first voltage threshold.

When the voltage of the battery charging the laser emitting apparatus is equal to or higher than the first voltage threshold in step 354 and determined to be equal to or lower than the second voltage threshold in step 356, the charge current value at this time is stored as the charge current value in the next test (used in step 351 of the next test) in step 358. When the voltage of the battery charging the laser emitting apparatus is determined to be lower than the first voltage threshold in step 354, the charge current value is lowered in step 355. On the other hand, when the voltage of the battery charging the laser emitting apparatus is determined to exceed the second voltage threshold in step 356, the charge current is increased in step 357.

In step 359, the laser emitting apparatus emits laser light and punctures the skin. In step 361, the component of blood flowing out from the punctured skin is measured, and the measurement result is displayed. In step 362, the remaining battery level after the test is measured. In step 363, the battery consumption level of this time is calculated, wherein the battery consumption level of this time is the difference between the remaining battery level measured in step 312 and the remaining battery level measured in step 362. Further, in step 363, second battery level threshold is reset, wherein second battery level threshold the sum of the battery consumption level of this time and the minimum electrical level required to drive the electrical circuit section for measurement. In step 364, the power supply is stopped.

Figure 54:
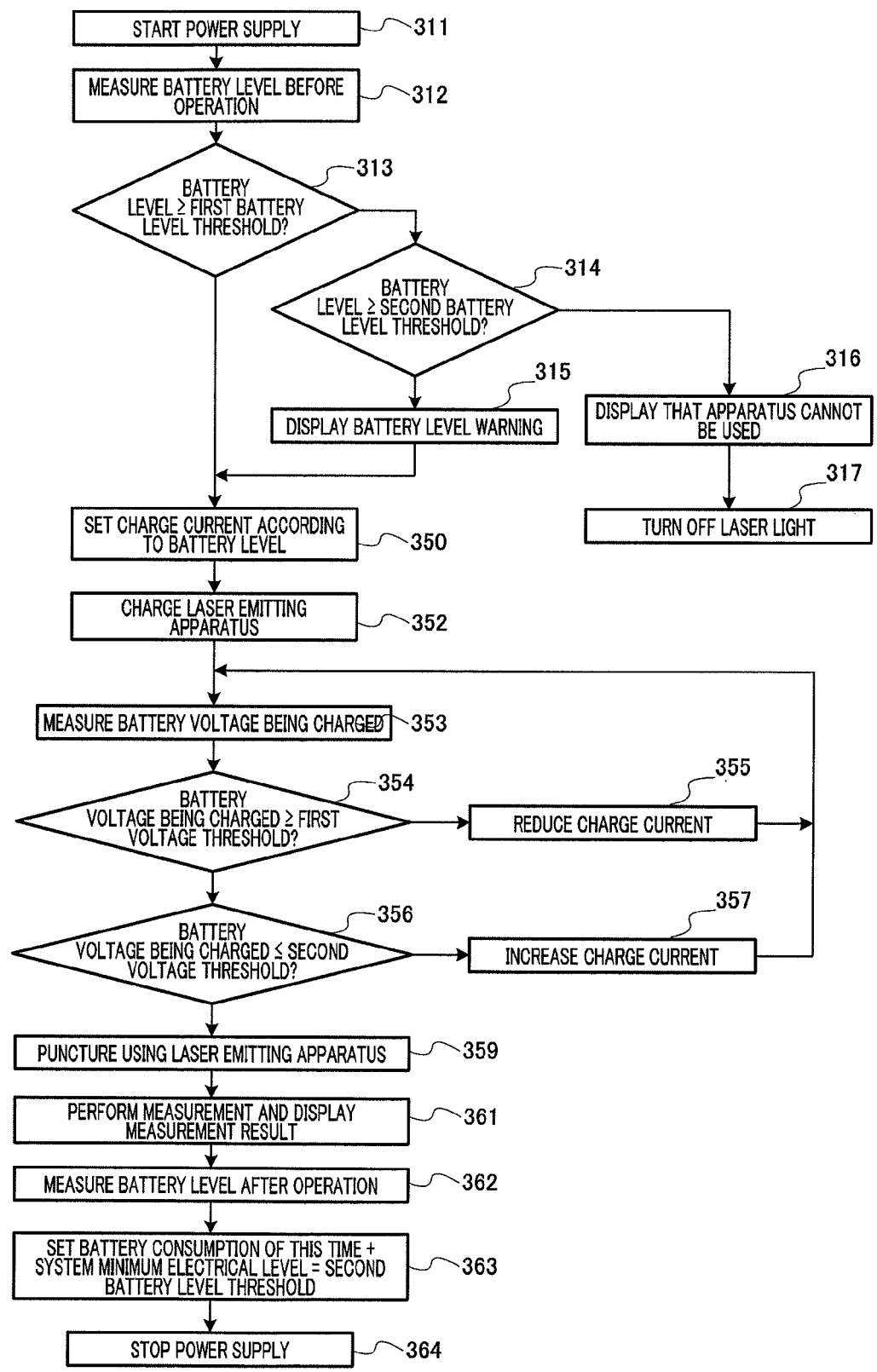
FIG. 54 is a flowchart showing a fourth example of the control steps in the power supply controlling section of FIG. 50.

A fourth example of the operation of power supply controlling section 200-1 shown in FIG. 50 will be described with reference to FIG. 54. The flow shown in FIG. 54 is similar to the flow shown in FIG. 53, but flow shown in FIG. 54 is different in the method of setting the charge current value for charging the laser emitting apparatus. That is, in the flow shown in FIG. 54, the charge current value is set in step 350 based on the remaining battery level. The specific setting method is as described above, and, basically, when the proportion of the remaining battery level is higher, the apparatus is charged with a higher current value. The other steps are the same as those in the flow shown in FIG. 53.

Figure 55:
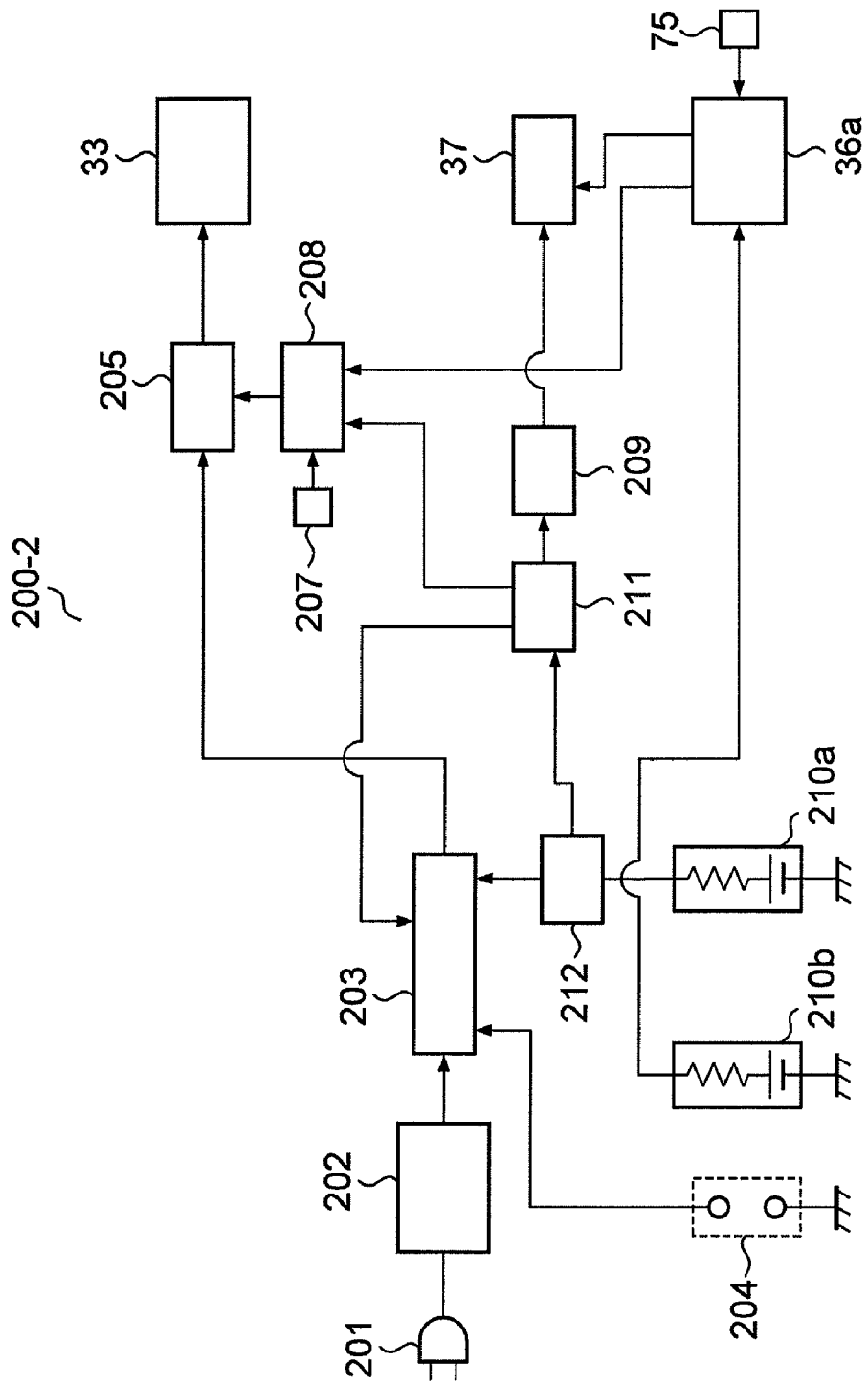
FIG. 55 is a block diagram showing a second example of the power supply controlling section of the blood test apparatus of the present invention.

A second example of the power supply controlling section will be described. FIG. 55 shows a second example of power supply controlling section 200-2 of the blood test apparatus. In FIG. 55, outlet 201 connected to a household AC power (used as an example of the external power supply) is connected to AC adapter 202. The output of AC adapter 202 can be connected to one input of power supply controlling circuit 203 removably, using a connector. Battery 210a is connected to battery level and battery voltage measuring circuit 212. The first output of circuit 212 is connected to power supply controlling circuit 203, and the second output of circuit 212 is connected to comparing section 211. Battery 210b is connected to electrical circuit section 36a. Connection terminal 204 for an emergency power supply is connected to power supply control circuit 203.

When power supply control circuit 203 is connected to AC adapter 202, power supply control circuit 203 controls so that the power supply of AC adapter 202 is preferentially used and battery 210a is not used. When the voltage outputted from AC adapter 202 is detected, and this voltage is outputted, the supply from battery 35 is stopped forcibly or charges battery 210a.

The output of power supply control circuit 203 is connected to boost circuit 205, and the output of boost circuit 205 is connected to laser emitting apparatus 33.

The first output of comparing section 211 is connected to power supply control circuit 203. The second output of comparing section 211 is connected to boost controlling section 208, and the output of boost controlling section 208 is connected to boost circuit 205. The third output of comparing section 211 is connected to display controlling section 209, and the output of display controlling section 209 is connected to display section 37.

Puncture button 75 is connected to the input of electrical circuit section 36a, and the signal caused by pressing puncture button 75 is connected to the input of boost controlling section 208 via electrical circuit section 36a. Emergency button 207 is connected to the other input of boost controlling section 208. The other output of electrical circuit section 36a is connected to display section 37.

Figure 56:
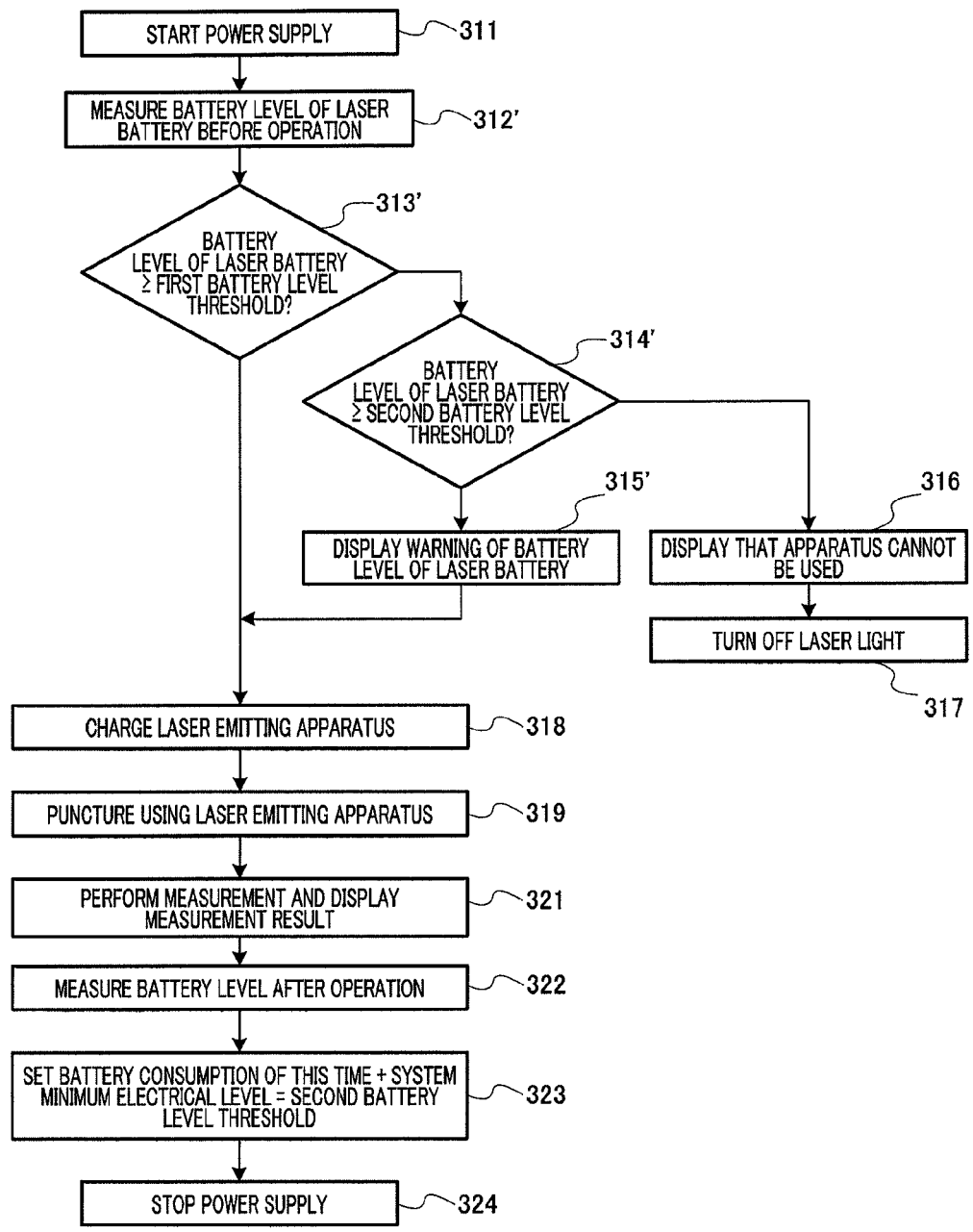
FIG. 56 is a flowchart showing a first example of control steps in the power supply controlling section of FIG. 55.

A first example of the operation of power supply controlling section 200-2 shown in FIG. 55 will be described with reference to FIG. 56. The flow shown in FIG. 56 is similar to the flow shown in FIG. 51. However, power supply controlling section 200-2 has two batteries (210a and 210b), and only battery 210a (laser battery) is used to charge the laser emitting apparatus. Therefore, the remaining battery level of the laser battery is measured in step 312', the remaining battery level measured in step 312' is compared with the first battery level threshold in step 313', and the remaining battery level measured in step 312' is compared with the second battery level threshold in step 314'. The other steps are the same as in the flow shown in FIG. 51.

Figure 57:
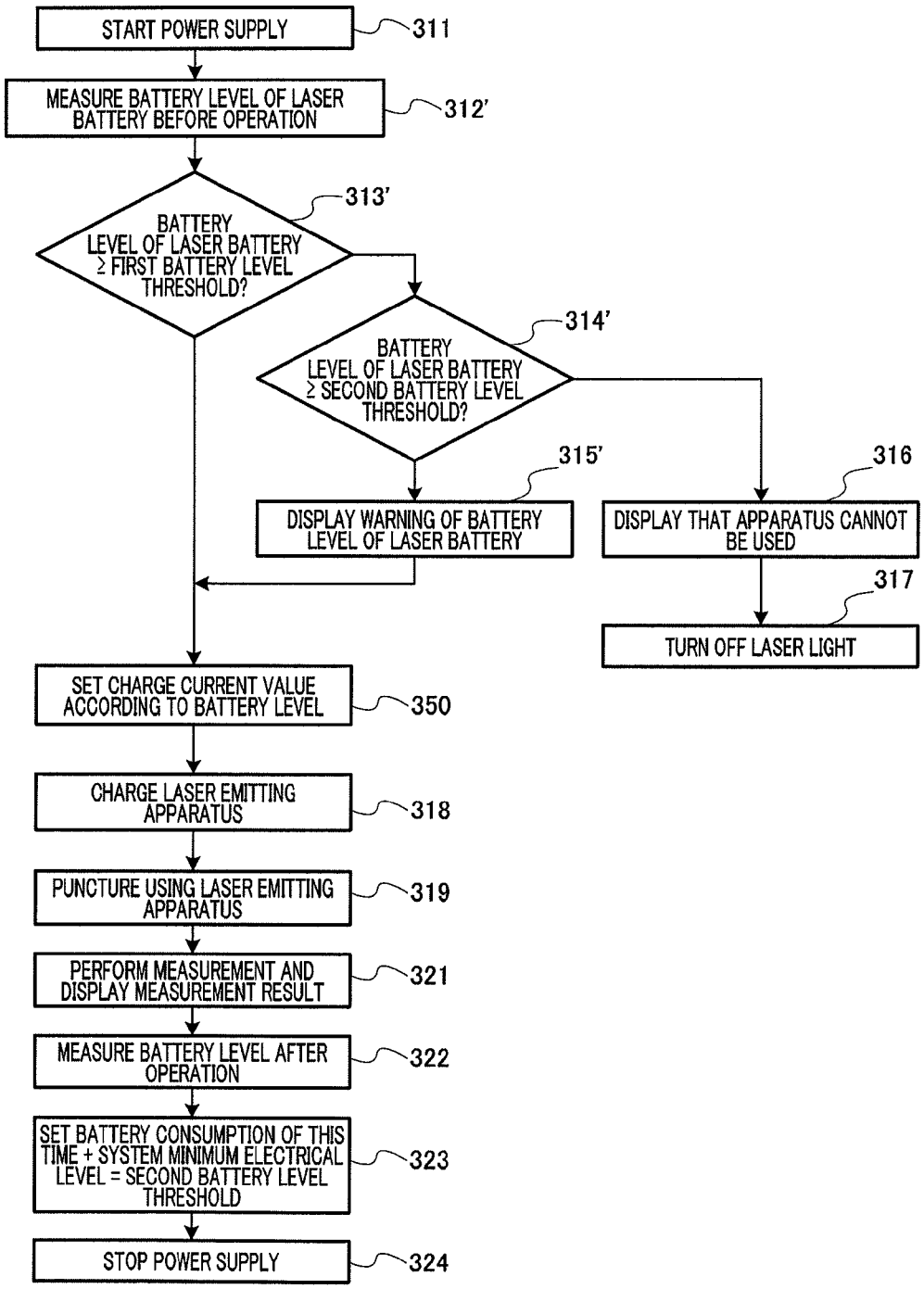
FIG. 57 is a flowchart showing a second example of the control steps in the power supply controlling section of FIG. 55.

A second example of the operation of power supply controlling section 200-1 shown in FIG. 55 will be described with reference to FIG. 57. Although the flow shown in FIG. 57 is similar to the flow shown in FIG. 56, the flow is different in the method of setting the charge current value for charging the laser emitting apparatus. That is, in the flow shown in FIG. 57, the charge current value is set in step 350 based on the remaining battery level. The specific setting method is as described above, and, basically, when the proportion of the remaining battery level is higher, the apparatus is charged with a higher current value. The other steps are the same as those in the flow shown in FIG. 56.

Figure 58:
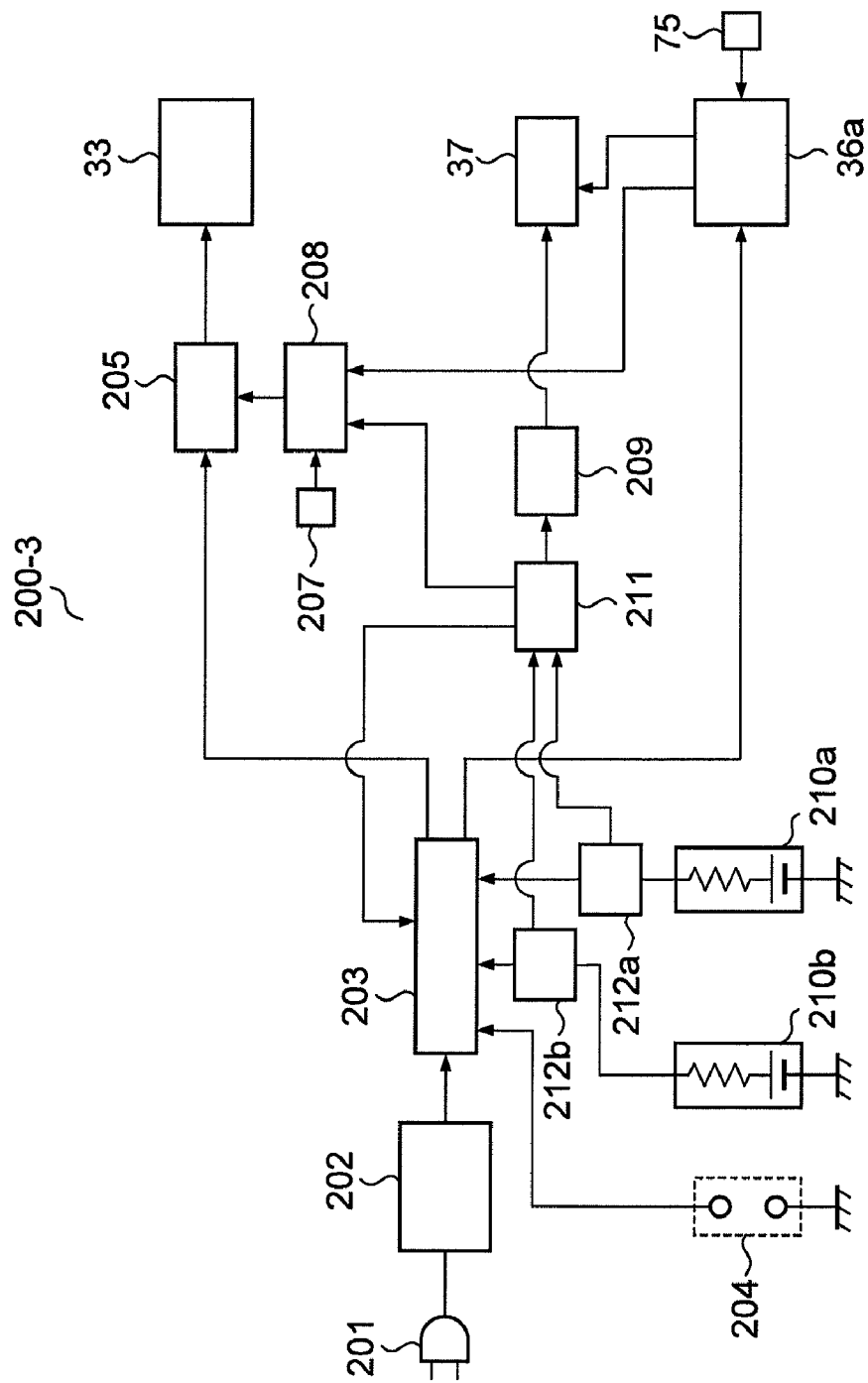
FIG. 58 is a block diagram showing a third example of the power supply controlling section of the blood test apparatus of the present invention.

A third example of the power supply controlling section will be described. FIG. 58 shows a third example of power supply controlling section 200-3 of the blood test apparatus. In FIG. 58, outlet 201 connected to a household AC power (used as an example of the external power supply) is connected to AC adapter 202. The output of AC adapter 202 can be connected to one input of power supply controlling circuit 203 removably, using a connector. Battery 210a is connected to battery level and battery voltage measuring circuit 212a. The first output of circuit 212 is connected to power supply controlling circuit 203, and the second output of circuit 212 is connected to comparing section 211. Battery 210b is connected to battery level and battery voltage measuring circuit 212b. The first output of circuit 212b is connected to power supply controlling circuit 203, and the second output of circuit 212b is connected to comparing section 211. Connection terminal 204 for an emergency power supply is connected to power supply control circuit 203.

Since both of battery 212a and battery 212b are connected to power supply controlling section 203, both of battery 212a and battery 212b charge laser emitting apparatus 33 and drive electrical circuit section 36a. Normally, battery 212a charges the laser emitting apparatus, and battery 212b drives electrical circuit section 36a. However, when the remaining battery level of battery 212a is low and the laser emitting apparatus cannot be charged and the remaining battery level of battery 212b is sufficient, battery 212b is used as a means for emergency to charge the laser emitting apparatus.

When power supply control circuit 203 is connected to AC adapter 202, power supply control circuit 203 controls so that the power supply of AC adapter 202 is preferentially used and battery 210a and battery 210b are not used. When the voltage outputted from AC adapter 202 is detected and this voltage is outputted, supply from battery 210a and battery 210b is stopped forcibly or battery 210a and battery 210b are charged.

The first output of power supply control circuit 203 is connected to electrical circuit section 36a. The second output of power supply control circuit 203 is connected to the input of boost circuit 205, and the output of boost circuit 205 is connected to laser emitting apparatus 33.

The first output of comparing section 211 is connected to power supply control circuit 203. The second output of comparing section 211 is connected to boost controlling section 208, and the output of boost controlling section 208 is connected to boost circuit 205. The third output of comparing section 211 is connected to display controlling section 209, and the output of display controlling section 209 is connected to display section 37.

Puncture button 75 is connected to the input of electrical circuit section 36a, and the signal caused by pressing puncture button 75 is connected to the input of boost controlling section 208 via electrical circuit section 36a. Emergency button 207 is connected to the other input of boost controlling section 208. The output of electrical circuit section 36a is connected to display section 37.

Figure 59:
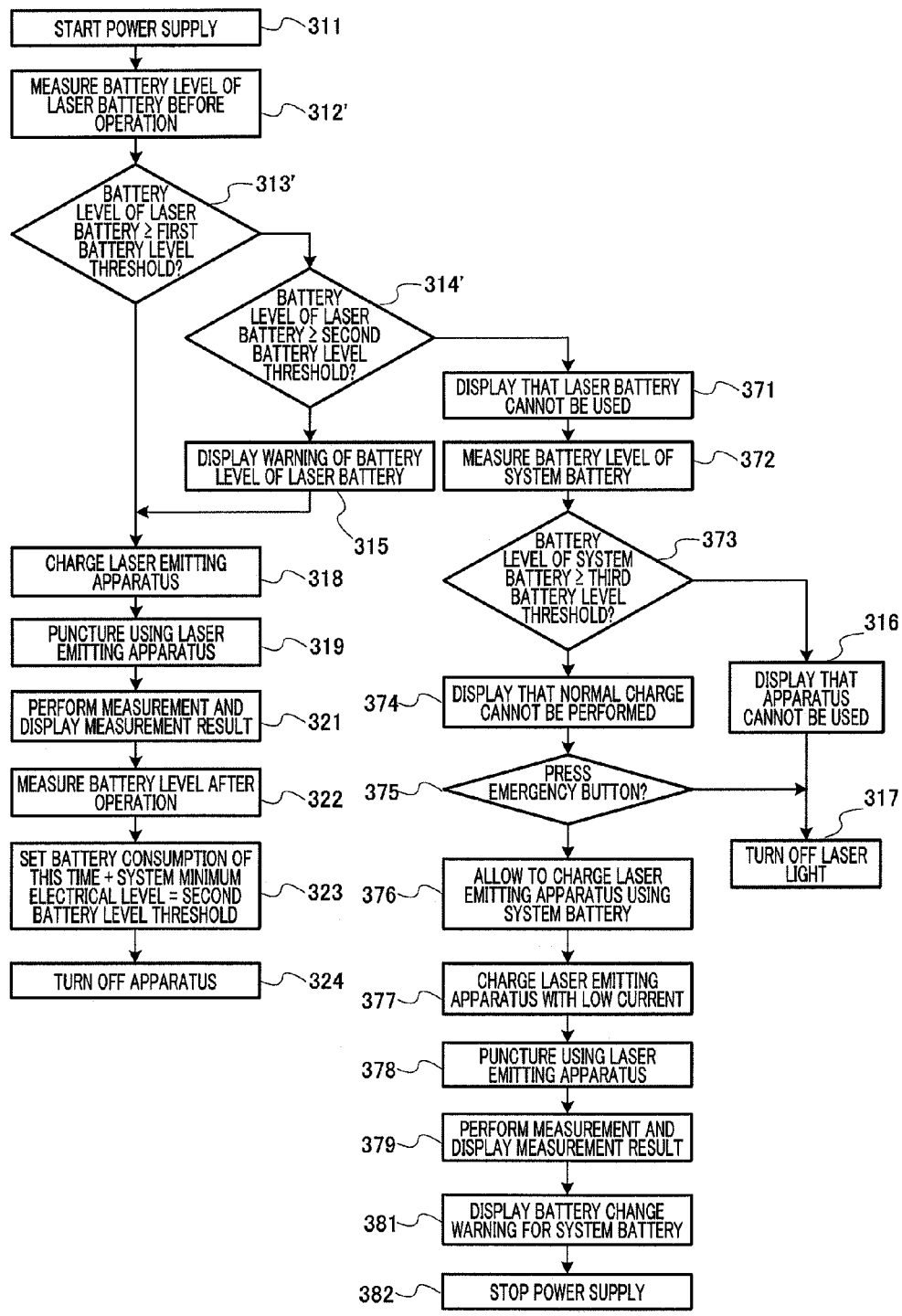
FIG. 59 is a flowchart showing a first example of control steps in the power supply controlling section of FIG. 58.

A first example of the operation of power supply controlling section 200-3 shown in FIG. 58 will be described with reference to FIG. 59. The flow shown in FIG. 59 is similar to the flow shown in FIG. 56. However, power supply controlling section 200-3 has two batteries (210a and 210b), and both batteries are connected to power supply control circuit 203. Basically, battery 210a (laser battery) is used to charge the laser emitting apparatus, and battery 210b (system battery) is used to drive electrical circuit section 36a. However, there is a case where, in an emergency, for example, when the remaining battery level of battery 210a is low, battery 210b charges the laser emitting apparatus.

In the same way as in the flow shown in FIG. 56, the remaining battery level of the laser battery is compared with the second battery level threshold in step 314', and, when the remaining battery level of the laser battery is determined to be lower than the second battery level threshold, a message for informing the user that the laser battery cannot be used is displayed in step 371.

In step 372, the remaining battery level of the system battery is measured. In step 373, the remaining battery level measured in step 372 is compared with the third battery level threshold. The third battery level threshold may be a sum of the electrical level to be charged so as to enable the laser emitting apparatus to emit laser light and the minimum electrical level of the system.

When the remaining battery level of the system battery is determined to be lower than the third battery level threshold, a message that the apparatus cannot be used is displayed in step 316 to inform the user that the test cannot be performed. Further, in step 317, power supply to the laser emitting apparatus is not allowed. On the other hand, when the remaining battery level of the system battery is determined to be equal to or higher than the third battery level threshold in step 373, in step 374, a message that normal charge cannot be performed is displayed to inform the user that the laser emitting apparatus cannot be charged normally (for example, the charging duration becomes long), and, if the user still desires to perform a test, the user is requested to press the emergency button.

When the emergency button is not pressed in step 375, step 317 is started, and power supply to the laser emitting apparatus is not allowed. On the other hand, when the emergency button is pressed in step 375, the charging of the laser emitting apparatus using the system battery is allowed in step 376, and the laser emitting apparatus is charged in step 377. Charging in step 377 is preferably performed with a lower current than usual to avoid a voltage drop of the system battery. A current value for charging is controlled by boost controlling section 208.

In step 378, the laser emitting apparatus emits laser light and punctures the skin. In step 379, the component of blood flowing out from the punctured skin is measured, and the measurement result is displayed. In step 381, a battery change warning for the system battery is displayed to encourage the user to change the system battery. In step 382, the power supply is stopped.

Figure 60:
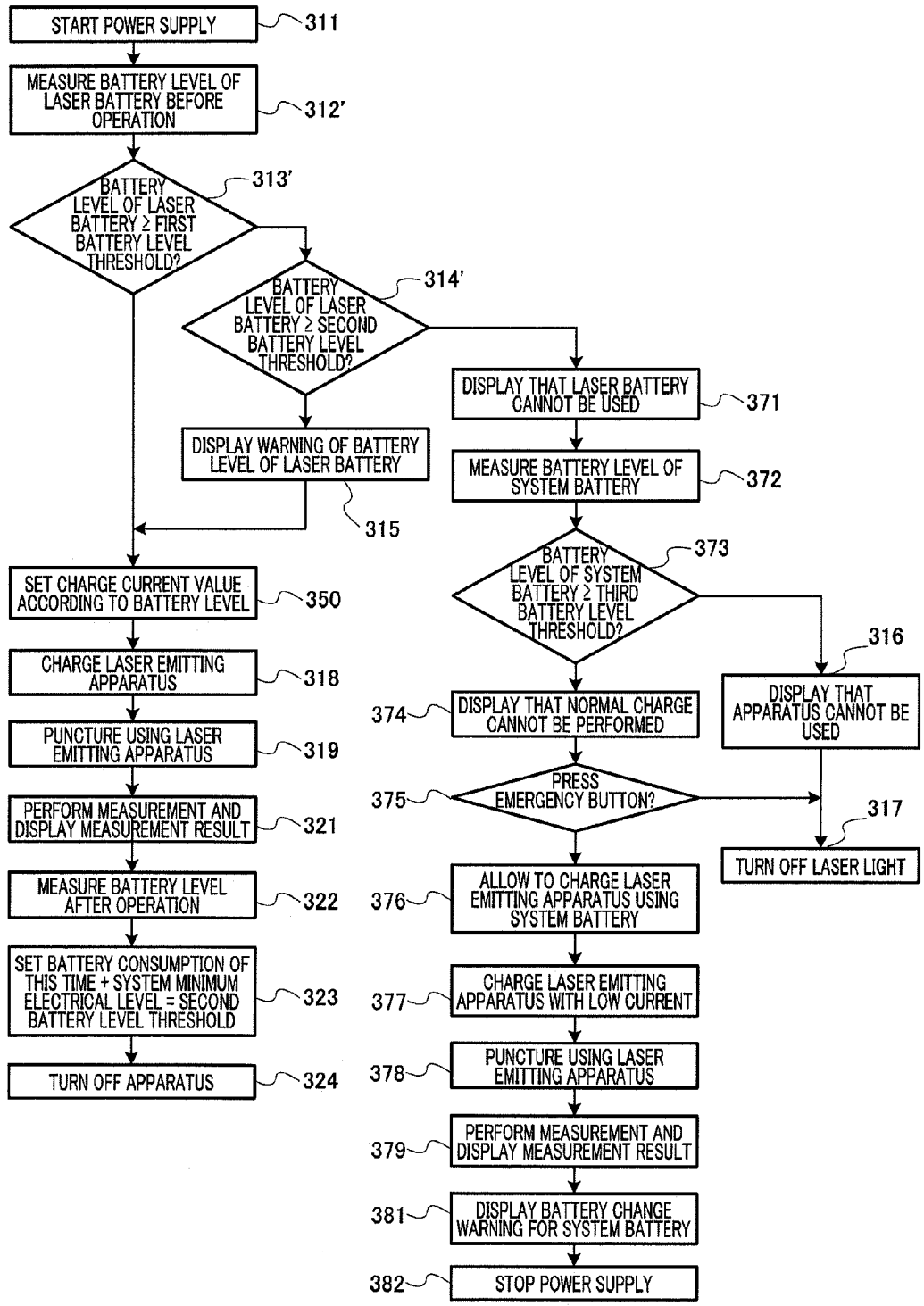
FIG. 60 is a flowchart showing a second example of the control steps in the power supply controlling section of FIG. 58.

A second example of the operation of power supply controlling section 200-3 shown in FIG. 58 will be described with reference to FIG. 60. The flow shown in FIG. 60 is similar to the flow shown in FIG. 59. However the flow is different in the method of setting the charge current value for charging the laser emitting apparatus. That is, in the flow shown in FIG. 60, the charge current value is set in step 350 based on the remaining battery level. The specific setting method is as described above, and, basically, when the proportion of the remaining battery level is higher, the apparatus is charged with a higher current value. The rest of the steps are the same as those in the flow shown in FIG. 59.

INDUSTRIAL APPLICABILITY

The blood test apparatus of the present invention uses laser light as a means for puncturing skin, and so a puncturing needle does not have to be replaced, and a blood sensor can be replaced in a simple manner. Further, despite the fact that a laser emitting apparatus consumes a large amount of power, the power supply is managed adequately, so that cases are less likely to occur where test cannot be performed due to power shortage. Therefore, the present invention is applicable to, for example, portable or household medical equipment particularly used by diabetes patients, as well as blood test apparatuses in the field of medicine.

The disclosures of Japanese Patent Application No. 2006-078416, filed on Mar. 22, 2006, Japanese Patent Application No. 2006-078424, filed on Mar. 22, 2006, including the specifications, drawings and abstracts, are incorporated herein by reference in their entirety.

The invention claimed is:

1. A blood test apparatus comprising:
an apparatus body;
a blood sensor that is attached to the apparatus body and that analyzes blood;
a puncturing section that is provided inside the apparatus body and that punctures skin of a patient through the blood sensor; and
an electrical circuit section that is connected to the blood sensor,
wherein:
the puncturing section comprises a laser emitting apparatus;
the blood test apparatus comprises a power supply control circuit that controls a supply of power from a power supply section including a power supply for driving the electrical circuit section and a power supply for driving the laser emitting apparatus; and
the power supply control circuit is configured:
to measure a remaining level of the power supply section,
to determine whether it is possible to perform both of a laser puncturing by the laser emitting apparatus and an analysis of blood by the electrical circuit section, based on the remaining level, and
if it determines that it is impossible to perform both of the laser puncturing and the analysis of blood, to not allow the laser puncturing but to allow the analysis of blood.

2. The blood test apparatus according to claim 1, wherein the power supply section comprises one or more battery power supplies.

3. The blood test apparatus according to claim 2, wherein the power supply section comprises a primary battery or a secondary battery.

4. The blood test apparatus according to claim 1, wherein the power supply section comprises a battery power supply and a connection terminal for an emergency power supply.

5. The blood test apparatus according to claim 1, wherein the power supply control circuit can control separately the power supply for driving the laser emitting apparatus and the power supply for the electrical circuit section, the electrical circuit section including a measuring circuit.

6. The blood test apparatus according to claim 2, further comprising:
a battery level measuring circuit that measures a remaining battery level of at least one of the one or more battery power supplies; and
a comparing section that compares a value of the measured battery level and a predetermined value of a battery level, wherein
the power supply control circuit controls the supply of power based on an output result of the comparing section.

7. The blood test apparatus according to claim 2, further comprising:
a battery voltage measuring circuit that measures a battery voltage of at least one of the one or more battery power supplies; and
a comparing section that compares a value of the measured battery voltage and a predetermined value of a battery voltage, wherein
the power supply control circuit controls the supply of power based on an output result of the comparing section.

8. The blood test apparatus according to claim 2, wherein:
the power supply section comprises two or more battery power supplies; and
the blood test apparatus further comprises a battery level measuring circuit that measures a remaining battery level of each of the two or more battery power supplies, or a battery voltage measuring circuit that measures a battery voltage of each of the two or more battery power supplies.

9. The blood test apparatus according to claim 8, further comprising a comparing section that compares the value of the remaining battery level measured in the battery level measuring circuit and a predetermined value of a battery level, or that compares the battery voltage measured in the battery voltage measuring circuit and a predetermined value of a battery voltage, wherein
the power supply control circuit controls the supply of power based on an output result of the comparing section.

10. The blood test apparatus according to claim 6, further comprising a display section that displays a test result of a blood test, wherein,
when the value of the measured battery level is determined to be equal to or less than the predetermined value of the battery level in the comparing section, the display section displays a result of the determination and
the power supply control circuit stops the supply of power to the laser emitting apparatus.

11. The blood test apparatus according to claim 7, further comprising
a display section that displays a test result of a blood test, wherein,
when the value of the measured battery voltage is determined to be equal to or less than the predetermined value of the battery voltage in the comparing section, the display section displays a result of the determination; and
the power supply control circuit stops the supply of power to the laser emitting apparatus.

12. The blood test apparatus according to claim 11, further comprising an input section for supplying power to the laser emitting apparatus even when the value of the measured battery voltage is determined to be equal to or less than the predetermined value of the battery voltage in the comparing section.

13. The blood test apparatus according to claim 1, further comprising a holder that holds the blood sensor, wherein
the blood sensor is integrated with the holder to form a blood sensor unit, and the blood sensor unit can be attached to and removed from the apparatus body.

14. The blood test apparatus according to claim 13, wherein:
the blood sensor unit further comprises a skin sensor; and
a laser light is not emitted from the laser emitting apparatus unless the skin sensor detects a contact with the skin.

15. The blood test apparatus according to claim 1, further comprising a negative pressure section inside the apparatus body,
wherein the negative pressure section creates a negative pressure near the blood sensor.

16. The blood test apparatus according to claim 15, further comprising a negative pressure control circuit that controls the negative pressure section, wherein
the power supply control circuit controls a supply of power to the negative pressure control circuit.

17. The blood test apparatus according to claim 1, wherein:
the power supply section comprises a battery power supply built in the apparatus body, and an external power supply; and
the power supply control circuit controls switching between the battery power supply and the external power supply to enable parallel use of battery power supply and external power supply, and, when the external power supply is connected, the external power supply is preferentially used.

18. The blood test apparatus according to claim 17, wherein, when the external power supply is connected, the power supply control circuit does not allow the battery power supply to output.

19. The blood test apparatus according to claim 17, wherein, when the external power supply is connected, the power supply control circuit causes the battery power supply to charge and does not allow the battery power supply to output.

* * * * *